United States Patent
Herr et al.

(10) Patent No.: US 9,244,075 B2
(45) Date of Patent: *Jan. 26, 2016

(54) COMPOSITIONS AND METHODS FOR DETECTING, DIAGNOSING, AND TREATING CANCER

(75) Inventors: John C. Herr, Charlottesville, VA (US); Euseblo S. Pires, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/813,680

(22) PCT Filed: Aug. 8, 2011

(86) PCT No.: PCT/US2011/046905
§ 371 (c)(1),
(2), (4) Date: Mar. 11, 2013

(87) PCT Pub. No.: WO2012/019184
PCT Pub. Date: Feb. 9, 2012

(65) Prior Publication Data
US 2013/0164215 A1    Jun. 27, 2013

Related U.S. Application Data

(60) Provisional application No. 61/371,215, filed on Aug. 6, 2010, provisional application No. 61/423,302, filed on Dec. 15, 2010, provisional application No. 61/499,448, filed on Jun. 21, 2011.

(51) Int. Cl.
| | |
|---|---|
| *A61K 39/00* | (2006.01) |
| *G01N 33/574* | (2006.01) |
| *A61K 39/395* | (2006.01) |
| *G01N 33/68* | (2006.01) |
| *A61K 38/17* | (2006.01) |
| *C12Q 1/68* | (2006.01) |

(52) U.S. Cl.
CPC ...... *G01N 33/57442* (2013.01); *A61K 38/1709* (2013.01); *A61K 39/3955* (2013.01); *C12Q 1/6886* (2013.01); *G01N 33/574* (2013.01); *G01N 33/57449* (2013.01); *G01N 33/689* (2013.01); *G01N 33/6884* (2013.01); *G01N 33/6893* (2013.01); *C12Q 2600/106* (2013.01); *C12Q 2600/136* (2013.01); *C12Q 2600/178* (2013.01)

(58) Field of Classification Search
CPC .......... A61K 47/48561; A61K 2039/505; A61K 51/1027; A61K 39/3955; C12Q 1/6886; G01N 33/574
See application file for complete search history.

(56) References Cited

U.S. PATENT DOCUMENTS

| | | |
|---|---|---|
| 2005/0214760 A1 | 9/2005 | Chan et al. |
| 2009/0068202 A1* | 3/2009 | Chen et al. .................. 424/173.1 |
| 2009/0214552 A1 | 8/2009 | Mandal et al. |
| 2010/0086948 A1 | 4/2010 | Gold et al. |
| 2010/0183617 A1* | 7/2010 | Herr et al. .................. 424/139.1 |

FOREIGN PATENT DOCUMENTS

| | | |
|---|---|---|
| EP | 2601530 A2 | 6/2013 |
| JP | 2008536803 A | 9/2008 |
| JP | 2013539018 A | 10/2013 |
| WO | WO-2005108415 A2 | 11/2005 |
| WO | WO-2006091535 A2 | 8/2006 |
| WO | WO-2010054187 A2 | 5/2010 |
| WO | WO-2012019184 A2 | 2/2012 |

OTHER PUBLICATIONS

Stancovski et al. (PNAS, 88:8691-8695, 1991).*
Jiang et al. (J. Biol. Chem., 280:4656-4662, 2005).*
"Australian Application Serial No. 2011285509, First Examiner Report mailed Nov. 5, 2013", 3 pgs.
"Australian Application Serial No. 2011285509, Response filed Jul. 19, 2014 to Office Action mailed Nov. 5, 2013", 29 pgs.
"European Application Serial No. 11815415.2, Office Action mailed Mar. 27, 2013", 2 pgs.
"European Application Serial No. 11815415.2, Response filed Jan. 31, 2014 to Office Action mailed Aug. 2, 2013", 9 pgs.
"European Application Serial No. 11815415.2, Response filed Apr. 11, 2013 to Office Action mailed Mar. 27, 2013", 15 pgs.
"European Application Serial No. 11815415.2, Supplementary European Search Report mailed Jul. 16, 2013", 7 pgs.
"International Application Serial No. PCT/US2011/046905, International Preliminary Report on Patentability mailed Feb. 21, 2013", 6 pgs.

(Continued)

*Primary Examiner* — Brad Duffy
*Assistant Examiner* — Nelson B Moseley, II
(74) *Attorney, Agent, or Firm* — Schwegman Lundberg & Woessner, P.A.

(57) ABSTRACT

The present invention provides compositions and methods useful for diagnosing, treating, and preventing cancer, particularly ovarian cancer and uterine cancer, based on the discovery that the oocyte specific protein, SAS1R (Sperm Acrosomal SLLP1 Receptor), which is a sperm protein receptor, is also expressed in various cancers, including ovarian cancer and uterine cancer. Six SAS1R variants have been previously identified, and they are encompassed by the invention. The present invention further provides antibodies useful for targeting SAS1R expressing cells and for killing such cells.

7 Claims, 38 Drawing Sheets

(56) References Cited

OTHER PUBLICATIONS

"International Application Serial No. PCT/US2011/046905, International Search Report mailed Apr. 9, 2012", 5 pgs.

"International Application Serial No. PCT/US2011/046905, Written Opinion mailed Apr. 9, 2012", 4 pgs.

Kurth, B. E, et al., "Immunogenicity of a multi-component recombinant human acrosomal protein vaccine in female Macaca fascicularis.", J Reprod Immunol., 77(2), (Apr. 2008), 126-41.

Quesada, V., et al., "Identification and characterization of human and mouse ovastacin: a novel metalloproteinase similar to hatching enzymes from arthropods, birds, amphibians, and fish", J Biol Chem., 279(25), (Jun. 18, 2004), 26627-34.

Tong, Z. B, et al., "A mouse gene encoding an oocyte antigen associated with autoimmune premature ovarian failure", Endocrinology, 140(8), (Aug. 1999), 3720-6.

"European Application Serial No. 11815415.2, Office Action mailed Jan. 22, 2015", 7 pgs.

Eusebio, Pires, et al., "SAS1B, a Cancer-Oocyte Antigen in Uterine and Ovarian Tumors", Presidential Inauguration Research Poster Competition, [Online]. Retrieved from the Internet: <http://www.virginia.edu/inauguration/posters/2.84.Biosciences. Pires. Herr. pdf>, (Mar. 16, 2011).

"Australian Application Serial No. 2011285509, Response filed Oct. 7, 2014 to Office Action mailed Aug. 15, 2014", 19 pgs.

"Australian Application Serial No. 2011285509, Subsequent Examiners Report mailed Aug. 15, 2014", 3 pgs.

"European Application Serial No. 11815415.2, Response filed May 19, 2015 to Office Action mailed Jan. 22, 2015", 11 pgs.

"Japanese Application Serial No. 2013-523383, Office Action mailed Jun. 30, 2015", not in English, 6 pgs.

* cited by examiner

Mouse SAS1R Expression Profile from EST Data base

| Breakdown by Body Sites | Mm.31313 | | | |
|---|---|---|---|---|
| adipose tissue | 0 / 1575 | embryonic tissue | 0 | 0 / 677964 |
| adrenal gland | 0 / 2365 | epididymis | 0 | 0 / 3001 |
| bladder | 0 / 15131 | extraembryonic tissue | 0 | 0 / 74236 |
| blood | 0 / 17220 | eye | 0 | 0 / 187876 |
| bone | 0 / 33643 | fertilized ovum | 327 | 9 / 27451 |
| bone marrow | 0 / 139674 | heart | 0 | 0 / 53737 |
| brain | 0 / 474157 | inner ear | 0 | 0 / 38356 |
| connective tissue | 0 / 19957 | intestine | 0 | 0 / 85878 |
| dorsal root ganglion | 0 / 11308 | joint | 0 | 0 / 17204 |
| prostate | 0 / 30005 | kidney | 0 | 0 / 124078 |
| salivary gland | 0 / 19482 | liver | 0 | 0 / 110508 |
| skin | 0 / 118716 | lung | 0 | 0 / 99614 |
| spinal cord | 0 / 23878 | lymph node | 0 | 0 / 15223 |
| spleen | 0 / 95027 | mammary gland | 0 | 0 / 306356 |
| stomach | 0 / 30559 | molar | 0 | 0 / 3630 |
| sympathetic ganglion | 0 / 9646 | muscle | 0 | 0 / 27498 |
| testis | 0 / 118168 | nasopharynx | 0 | 0 / 8102 |
| thymus | 0 / 121624 | olfactory mucosa | 0 | 0 / 3355 |
| thyroid | 0 / 8891 | ovary | 729 | 40 / 54848 |
| tongue | 0 / 10285 | oviduct | 0 | 0 / 3646 |
| turbinate | 0 / 1388 | pancreas | 0 | 0 / 106590 |
| uterus | 0 / 6934 | oocyte | 1385 | 27 / 19488 |
| vagina | 0 / 5961 | unfertilized ovum | 638 | 13 / 20366 |
| vesicular gland | 0 / 2192 | zygote | 317 | 9 / 28382 |
| | | cleavage | 0 | 0 / 27730 |
| | | morula | 0 | 0 / 38122 |
| | | blastocyst | 0 | 0 / 69938 |
| | | egg cylinder | 0 | 0 / 12257 |
| | | gastrula | 0 | 0 / 28673 |
| | | organogenesis | 0 | 0 / 128591 |
| | | fetus | 0 | 0 / 670244 |
| | | neonate | 0 | 0 / 107177 |
| | | juvenile | 0 | 0 / 293396 |
| | | adult | 0 | 0 / 1026072 |

FIG. 1

Human SAS1R Expression Profile from EST Data base

| Breakdown by Body Sites | Hs.447993 | | | |
|---|---|---|---|---|
| adipose tissue | 0 / 13154 | pharynx | 0 / 41485 |
| adrenal gland | 0 / 33321 | pituitary gland | 0 / 16732 |
| ascites | 0 / 40069 | placenta | 0 / 284095 |
| bladder | 0 / 30130 | prostate | 0 / 190881 |
| blood | 0 / 124100 | salivary gland | 0 / 20288 |
| bone | 0 / 71794 | skin | 0 / 211608 |
| bone marrow | 0 / 49189 | spleen | 0 / 54069 |
| brain | 0 / 1104500 | stomach | 0 / 97178 |
| cervix | 0 / 48496 | testis | 0 / 331397 |
| connective tissue | 0 / 149637 | thymus | 0 / 81238 |
| connective tissue | 0 / 149627 | thyroid | 0 / 47945 |
| ear | 0 / 16342 | tonsil | 0 / 17041 |
| embryonic tissue | 0 / 215827 | trachea | 0 / 52435 |
| esophagus | 0 / 20208 | umbilical cord | 0 / 13767 |
| eye | 0 / 211736 | uterus | 1 / 233964 |
| heart | 0 / 90352 | vascular | 0 / 51942 |
| intestine | 0 / 235438 | ovary | 0 / 102648 |
| kidney | 0 / 212589 | pancreas | 0 / 215299 |
| larynx | 0 / 24451 | parathyroid | 0 / 20642 |
| liver | 0 / 208377 | pharynx | 0 / 41485 |
| lung | 0 / 338114 | | |
| lymph | 0 / 44398 | | |
| lymph node | 0 / 91885 | | |
| mammary gland | 0 / 154325 | | |
| mouth | 0 / 67204 | | |
| muscle | 0 / 108185 | | |
| nerve | 0 / 15811 | | |

Human SAS1R ESTs in GENBANK are found in uterine cancer.

FIG. 3

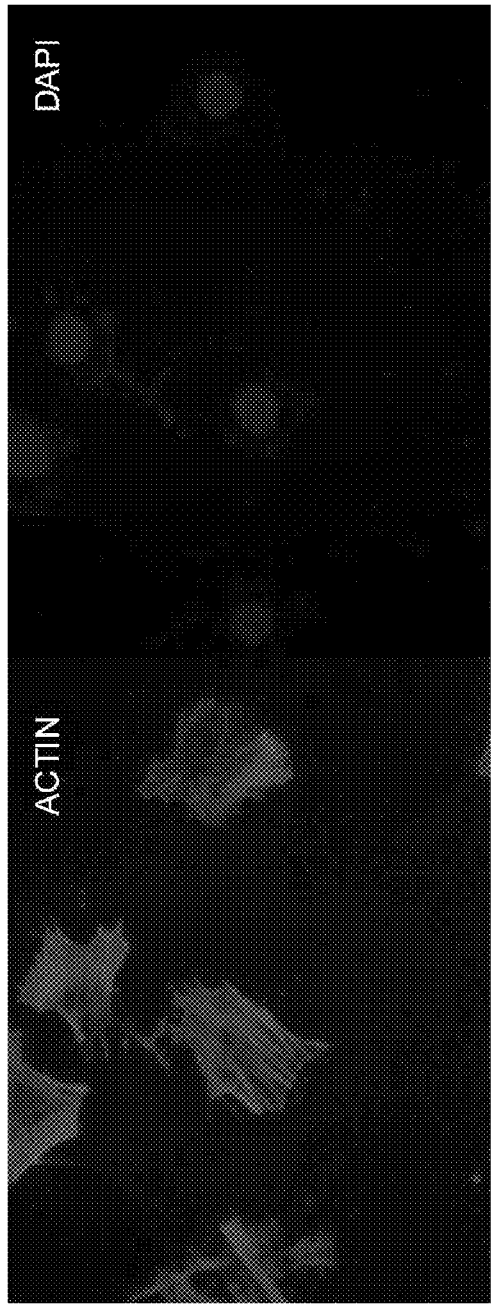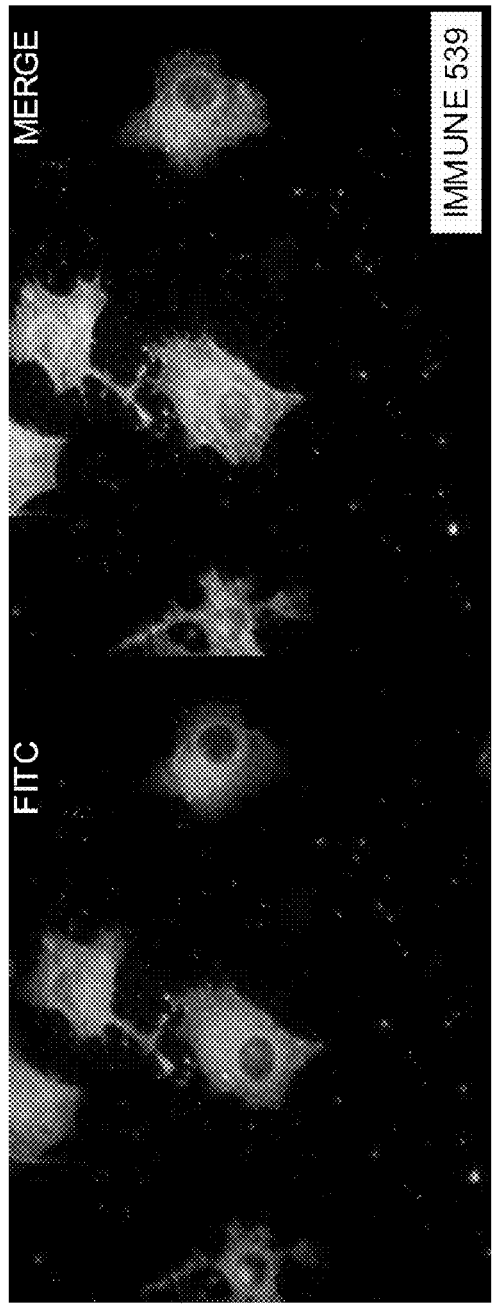

SAS1R is also expressed in human uterine tumors but not in normal uterine tissue C-term specific primers amplifying a 310 bp product was used to check for SAS1B transcripts in uterine tumors. 7/7 Grade 1 Uterine tumors demonstrated the present of SAS1B transcripts. 1/4 Grade 3 tumors showed the SAS1B transcripts. Normal uterine sample (NU) did not show any SAS1B transcripts.

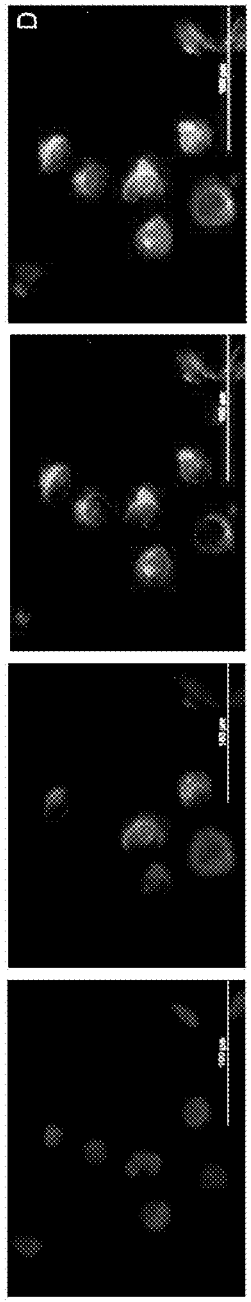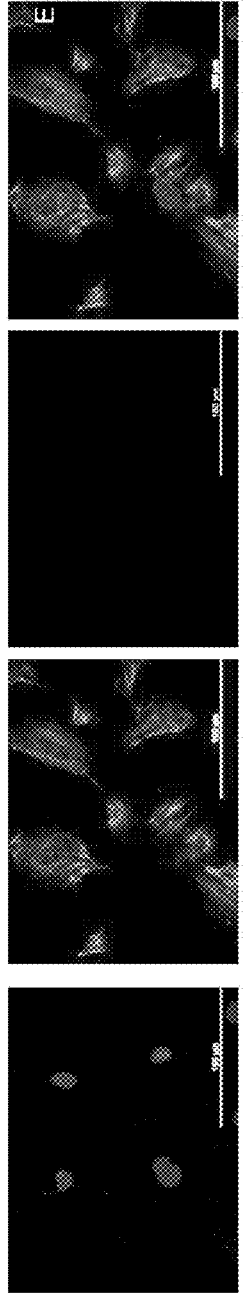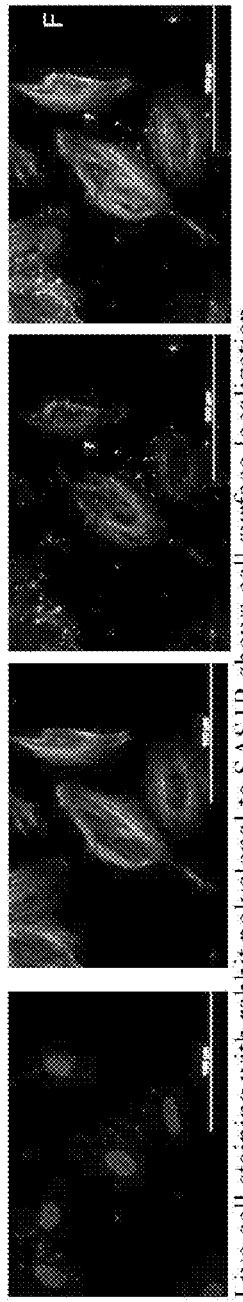

Live cell staining with rabbit polyclonal to SAS1R shows cell surface localization. Panels A,C and E have been stained with preimmune sera. Panels B, D and F are stained with Immune sera to SAS1R. Cell nucleus was counterstained with DAPI. Phalloidin (red stain) was used to localize cytoskeletal actin protein. No immunostaining is seen when cell lines MMMT 539 (Panel A), MMMT 308 (Panel C) and control endometrial cell line MAD10 (Panel E) were stained with pre-immune sera. However, a distinct cell surface localization was observed with MMMT 539 (Panel B) and MMMT 308 (Panel D) with the post immune sera. No immunostaining was observed with control endometrial cell line MAD10 (Panel F) with the post immune sera.

SEQUENCE LISTING

<160> NUMBER OF SEQ ID NOS: 33

<210> SEQ ID NO 1
<211> LENGTH: 1320
<212> TYPE: DNA
<213> ORGANISM: mus musculus

<400> SEQUENCE: 1

| | | | | | |
|---|---|---|---|---|---|
| atggcctctc | tgaagaggtt | tcagacgctc | gtgcccctgg | atcacaaaca | aggtacctta | 60 |
| tttgaaatta | ttggagagcc | caagttgccc | aagtggttcc | atgtcgaatg | cctggaagat | 120 |
| ccaaaaagac | tgtacgtgga | acctcggcta | ctggaaatca | tgtttggtaa | ggatggagag | 180 |
| cacatcccac | atcttgaatc | tatgttgcac | accctgatac | atgtgaacgt | gtggggccct | 240 |
| gaaaggcgag | ctgagatttg | gatattcgga | ccgccgcctt | tccgaaggga | cgttgaccgg | 300 |
| atgctcactg | atctggctca | ctattgccgc | atgaaactga | tggaaataga | ggctctggag | 360 |
| gctggagttg | agcgtcgtcg | tatggcggcc | cataaggctg | ccacccagcc | tgctcccgtg | 420 |
| aaggtccgcg | aggctgcccc | tcggcccgct | tccgtgaagg | tccctgagac | ggccacccag | 480 |
| cctgctcccg | tgaaggtccg | cgaggctgcc | cctcagcccg | ctccggtgca | ggaggtccgc | 540 |
| gaggctgccc | ctcagcaggc | ttccgtgcag | gaggaggtcc | gcgaggctgc | caccgagcag | 600 |
| gctcccgtgc | aggaggtccg | cgaggctgcc | accgagcagc | tcccgtgca | ggaggtcagc | 660 |
| gaggctgcca | ccgagcaggc | tcccgtgcag | gaggtcaacg | aggctgccac | cgagcaggct | 720 |
| tccgtgcagg | cggtccgcga | ggctgccacc | cggccggctc | ccgggaaggt | ccgcaaggcg | 780 |
| gccacccagc | cggctccggt | gcaggtttgc | caggaggcca | cccagttggc | tcccgtgaag | 840 |
| gtccgcgagg | cggccacccca | gccggcttcc | gggaaggtcc | gcgaggcggc | cacccagttg | 900 |
| gctcctgtga | aggtccgcaa | ggcagccacc | cagttggctc | ctgtgaaggt | ccacgaggcg | 960 |
| gccacccagc | cggctccggg | gaaggtcagc | gatgctgcca | cgcagtcggc | ttcggtgcag | 1020 |
| gttcgtgagg | ctgccacgca | gctgtctccc | gtggaggcca | ctgatactag | ccagttggct | 1080 |
| caggtgaagg | ctgatgaagc | ctttgcccag | cacacttcag | ggaggcccca | ccaggttgcc | 1140 |
| aatgggcagt | ctcccattga | agtctgtgag | actgccaccg | ggcagcattc | tctagatgtc | 1200 |
| tctagggcct | tgtcccagaa | gtgtcctgag | gttttttgagt | gggagaccca | gagttgtttg | 1260 |
| gatggcagct | atgtcatagt | tcagcctcca | agggatgcct | gggaatcatt | tatcatatta | 1320 |

<210> SEQ ID NO 2
<211> LENGTH: 440
<212> TYPE: PRT
<213> ORGANISM: mus musculus

<400> SEQUENCE: 2

Met Ala Ser Leu Lys Arg Phe Gln Thr Leu Val Pro Leu Asp His Lys
1               5                   10                  15

Gln Gly Thr Leu Phe Glu Ile Ile Gly Glu Pro Lys Leu Pro Lys Trp
            20                  25                  30

Phe His Val Glu Cys Leu Glu Asp Pro Lys Arg Leu Tyr Val Glu Pro
        35                  40                  45

Arg Leu Leu Glu Ile Met Phe Gly Lys Asp Gly Glu His Ile Pro His
    50                  55                  60

Leu Glu Ser Met Leu His Thr Leu Ile His Val Asn Val Trp Gly Pro
65                  70                  75                  80

Glu Arg Arg Ala Glu Ile Trp Ile Phe Gly Pro Pro Pro Phe Arg Arg
                85                  90                  95

Asp Val Asp Arg Met Leu Thr Asp Leu Ala His Tyr Cys Arg Met Lys
            100                 105                 110

Leu Met Glu Ile Glu Ala Leu Glu Ala Gly Val Glu Arg Arg Met
        115                 120                 125

Ala Ala His Lys Ala Ala Thr Gln Pro Ala Pro Val Lys Val Arg Glu
    130                 135                 140

Ala Ala Pro Arg Pro Ala Ser Val Lys Val Pro Glu Thr Ala Thr Gln
145                 150                 155                 160

Pro Ala Pro Val Lys Val Arg Glu Ala Ala Pro Gln Pro Ala Pro Val
                165                 170                 175

Gln Glu Val Arg Glu Ala Ala Pro Gln Gln Ala Ser Val Gln Glu Glu
            180                 185                 190

Val Arg Glu Ala Ala Thr Glu Gln Ala Pro Val Gln Glu Val Arg Glu
        195                 200                 205

Ala Ala Thr Glu Gln Ala Pro Val Gln Glu Val Ser Glu Ala Ala Thr
    210                 215                 220

Glu Gln Ala Pro Val Gln Glu Val Asn Glu Ala Ala Thr Glu Gln Ala
225                 230                 235                 240

Ser Val Gln Ala Val Arg Glu Ala Ala Thr Arg Pro Ala Pro Gly Lys
                245                 250                 255

Val Arg Lys Ala Ala Thr Gln Pro Ala Pro Val Gln Val Cys Gln Glu
            260                 265                 270

Ala Thr Gln Leu Ala Pro Val Lys Val Arg Glu Ala Ala Thr Gln Pro
        275                 280                 285

Ala Ser Gly Lys Val Arg Glu Ala Ala Thr Gln Leu Ala Pro Val Lys
    290                 295                 300

Val Arg Lys Ala Ala Thr Gln Leu Ala Pro Val Lys Val His Glu Ala
305                 310                 315                 320

Ala Thr Gln Pro Ala Pro Gly Lys Val Ser Asp Ala Ala Thr Gln Ser
                325                 330                 335

Ala Ser Val Gln Val Arg Glu Ala Ala Thr Gln Leu Ser Pro Val Glu
            340                 345                 350

Ala Thr Asp Thr Ser Gln Leu Ala Gln Val Lys Ala Asp Glu Ala Phe
        355                 360                 365

Ala Gln His Thr Ser Gly Glu Ala His Gln Val Ala Asn Gly Gln Ser
    370                 375                 380

Pro Ile Glu Val Cys Glu Thr Ala Thr Gly Gln His Ser Leu Asp Val
385                 390                 395                 400

Ser Arg Ala Leu Ser Gln Lys Cys Pro Glu Val Phe Glu Trp Glu Thr
                405                 410                 415

Gln Ser Cys Leu Asp Gly Ser Tyr Val Ile Val Gln Pro Pro Arg Asp
            420                 425                 430

Ala Trp Glu Ser Phe Ile Ile Leu
        435                 440

<210> SEQ ID NO 3
<211> LENGTH: 1248
<212> TYPE: DNA
<213> ORGANISM: mus musculus

<400> SEQUENCE: 3
atggcctctc tgaagaggtt tcagacgctc gtgcccctgg atcacaaaca aggtacctta     60
tttgaaatta ttggagagcc caagttgccc aagtggttcc atgtcgaatg cctggaagat    120

```
ccaaaaagac tgtacgtgga acctcggcta ctggaaatca tgtttggtaa ggatggagag    180
cacatcccac atcttgaatc tatgttgcac accctgatac atgtgaacgt gtggggccct    240
gaaaggcgag ctgagatttg atattcgga ccgccgcctt ccgaaggga cgttgaccgg      300
atgctcactg atctggctca ctattgccgc atgaaactga tggaaataga ggctctggag    360
gctggagttg agcgtcgtcg tatggcggcc cataaggctg ccacccagcc tgctcccgtg    420
aaggtccgcg aggctgcccc tcagcccgct ccggtgcagg aggtccgcga ggctgcccct    480
cagcaggctt ccgtgcagga ggaggtccgc gaggctgcca ccgagcaggc tcccgtgcag    540
gaggtccgcg aggctgccac cgagcaggct cccgtgcagg aggtcagcga ggctgccacc    600
gagcaggctc ccgtgcagga ggtcaacgag gctgccaccg agcaggcttc cgtgcaggcg    660
gtccgcgagg ctgccacccg gccggctccc gggaaggtcc gcaaggcggc acccagccg     720
gctccggtgc aggtttgcca ggaggccacc cagttggctc ccgtgaaggt ccgcgaggcg    780
gccacccagc cggcttccgg gaaggtccgc gaggcggcca cccagttggc tcctgtgaag    840
gtccgcaagg cagccaccca gttggctcct gtgaaggtcc acgaggcggc acccagccg     900
gctccgggga aggtcagcga tgctgccacg cagtcggctt cggtgcaggt tcgtgaggct    960
gccacgcagc tgtctcccgt ggaggccact gatactagcc agttggctca ggtgaaggct   1020
gatgaagcct ttgcccagca cacttcaggg gaggcccacc aggttgccaa tgggcagtct   1080
cccattgaag tctgtgagac tgccaccggg cagcattctc tagatgtctc tagggccttg   1140
tcccagaagt gtcctgaggt ttttgagtgg agacccaga gttgtttgga tggcagctat   1200
gtcatagttc agcctccaag ggatgcctgg gaatcattta tcatatta                1248
```

<210> SEQ ID NO 4
<211> LENGTH: 416
<212> TYPE: PRT
<213> ORGANISM: mus musculus

<400> SEQUENCE: 4

Met Ala Ser Leu Lys Arg Phe Gln Thr Leu Val Pro Leu Asp His Lys
1               5                   10                  15

Gln Gly Thr Leu Phe Glu Ile Ile Gly Glu Pro Lys Leu Pro Lys Trp
            20                  25                  30

Phe His Val Glu Cys Leu Glu Asp Pro Lys Arg Leu Tyr Val Glu Pro
        35                  40                  45

Arg Leu Leu Glu Ile Met Phe Gly Lys Asp Gly Glu His Ile Pro His
    50                  55                  60

Leu Glu Ser Met Leu His Thr Leu Ile His Val Asn Val Trp Gly Pro
65                  70                  75                  80

Glu Arg Arg Ala Glu Ile Trp Ile Phe Gly Pro Pro Phe Arg Arg
                85                  90                  95

Asp Val Asp Arg Met Leu Thr Asp Leu Ala His Tyr Cys Arg Met Lys
            100                 105                 110

Leu Met Glu Ile Glu Ala Leu Glu Ala Gly Val Glu Arg Arg Arg Met
        115                 120                 125

Ala Ala His Lys Ala Ala Thr Gln Pro Ala Pro Val Lys Val Arg Glu
    130                 135                 140

Ala Ala Pro Gln Pro Ala Pro Val Gln Glu Val Arg Glu Ala Ala Pro
145                 150                 155                 160

Gln Gln Ala Ser Val Gln Glu Glu Val Arg Glu Ala Ala Thr Glu Gln
                165                 170                 175

```
Ala Pro Val Gln Glu Val Arg Glu Ala Ala Thr Glu Gln Ala Pro Val
            180                 185                 190

Gln Glu Val Ser Glu Ala Ala Thr Glu Gln Ala Pro Val Gln Glu Val
        195                 200                 205

Asn Glu Ala Ala Thr Glu Gln Ala Ser Val Gln Ala Val Arg Glu Ala
    210                 215                 220

Ala Thr Arg Pro Ala Pro Gly Lys Val Arg Lys Ala Ala Thr Gln Pro
225                 230                 235                 240

Ala Pro Val Gln Val Cys Gln Glu Ala Thr Gln Leu Ala Pro Val Lys
                245                 250                 255

Val Arg Glu Ala Ala Thr Gln Pro Ala Ser Gly Lys Val Arg Glu Ala
            260                 265                 270

Ala Thr Gln Leu Ala Pro Val Lys Val Arg Lys Ala Ala Thr Gln Leu
        275                 280                 285

Ala Pro Val Lys Val His Glu Ala Ala Thr Gln Pro Ala Pro Gly Lys
    290                 295                 300

Val Ser Asp Ala Ala Thr Gln Ser Ala Ser Val Gln Val Arg Glu Ala
305                 310                 315                 320

Ala Thr Gln Leu Ser Pro Val Glu Ala Thr Asp Thr Ser Gln Leu Ala
                325                 330                 335

Gln Val Lys Ala Asp Glu Ala Phe Ala Gln His Thr Ser Gly Glu Ala
            340                 345                 350

His Gln Val Ala Asn Gly Gln Ser Pro Ile Glu Val Cys Glu Thr Ala
        355                 360                 365

Thr Gly Gln His Ser Leu Asp Val Ser Arg Ala Leu Ser Gln Lys Cys
    370                 375                 380

Pro Glu Val Phe Glu Trp Glu Thr Gln Ser Cys Leu Asp Gly Ser Tyr
385                 390                 395                 400

Val Ile Val Gln Pro Pro Arg Asp Ala Trp Glu Ser Phe Ile Ile Leu
                405                 410                 415

<210> SEQ ID NO 5
<211> LENGTH: 1242
<212> TYPE: DNA
<213> ORGANISM: mus musculus

<400> SEQUENCE: 5
atgggagcac cctcagcatc cagatgttct ggagtctgca gtaccagtgt tccagaaggc     60
ttcactcctg agggaagccc ggtatttcag dacaaggaca tccccgcaat taaccaaggg    120
ctcatctcag aggagacccc agaaagcagc ttcctggtag aaggggacat tatccggcca    180 agcccctttcc gattgttgtc agtgaccaat aataaatggc caagggcgt tggtggcttt    240 gtggagatcc cctcctgct ttccagaaag tatgatgaac tcagccgccg ggtcattatg    300
gatgcctttg ctgagtttga acgtttcaca tgcatccggt tgttgcctta ccatggtcag    360
agagactttt tttccattct tcctatggcg gggtgtttct ctggtgtggg acgcagtgga    420
gggatgcagg tggtgtcctt ggcacccact tgtctccgga agggccgagg cattgtccta    480
catgagctca tgcacgtact tggcttctgg catgagcatt cacgggcaga tcgggaccgc    540
tacatccaag tcaactggaa cgagatcctc ccgggctttg aaatcaactt catcaagtca    600
cggagtacca atatgttagt tccctatgac tactcatctg tgatgcatta tgggagattt    660
gccttcagct ggcgtgggca gcccaccatc ataccactct ggacctccag tgttcacatt    720
ggccagcgat ggaacctgag tacctcagat atcacccggg tctgcaggct gtataactgc    780
```

```
agccggagtg tccctgactc ccacgggaga gggtttgagg cccagagtga tggaagcagc    840
ctcacccctg cctctatatc acgtctacaa agacttctcg aggcactgtc agaggaatct    900
ggaagctctg cccctagtgg ctccaggact ggaggccaga gtattgccgg gcttggtaac    960
agccagcaag gatgggagca tcctcctcag agcacattca gtgtgggagc cttggcaaga   1020
ccacctcaga tgctagccga tgcttcaaaa tcggggcctg agcaggtgc agacagcttg    1080 tctctagagc agttccagct agcccaggcc cccactgtac ctcttgctct atttccagaa   1140
gccagagaca agccagcacc tatccaagat gcctttgaga ggctagctcc acttccagga   1200
ggctgtgcac ctggaagtca cattagagag gtgcccagag ac                      1242
```

<210> SEQ ID NO 6
<211> LENGTH: 414
<212> TYPE: PRT
<213> ORGANISM: mus musculus

<400> SEQUENCE: 6

```
Met Gly Ala Pro Ser Ala Ser Arg Cys Ser Gly Val Cys Ser Thr Ser
1               5                   10                  15

Val Pro Glu Gly Phe Thr Pro Glu Gly Ser Pro Val Phe Gln Asp Lys
            20                  25                  30

Asp Ile Pro Ala Ile Asn Gln Gly Leu Ile Ser Glu Thr Pro Glu
        35                  40                  45

Ser Ser Phe Leu Val Glu Gly Asp Ile Ile Arg Pro Ser Pro Phe Arg
    50                  55                  60

Leu Leu Ser Val Thr Asn Asn Lys Trp Pro Lys Gly Val Gly Gly Phe
65                  70                  75                  80

Val Glu Ile Pro Phe Leu Leu Ser Arg Lys Tyr Asp Glu Leu Ser Arg
                85                  90                  95

Arg Val Ile Met Asp Ala Phe Ala Glu Phe Glu Arg Phe Thr Cys Ile
            100                 105                 110

Arg Phe Val Ala Tyr His Gly Gln Arg Asp Phe Val Ser Ile Leu Pro
        115                 120                 125

Met Ala Gly Cys Phe Ser Gly Val Gly Arg Ser Gly Gly Met Gln Val
    130                 135                 140

Val Ser Leu Ala Pro Thr Cys Leu Arg Lys Gly Arg Gly Ile Val Leu
145                 150                 155                 160

His Glu Leu Met His Val Leu Gly Phe Trp His Glu His Ser Arg Ala
                165                 170                 175

Asp Arg Asp Arg Tyr Ile Gln Val Asn Trp Asn Glu Ile Leu Pro Gly
            180                 185                 190

Phe Glu Ile Asn Phe Ile Lys Ser Arg Ser Thr Asn Met Leu Val Pro
        195                 200                 205

Tyr Asp Tyr Ser Ser Val Met His Tyr Gly Arg Phe Ala Phe Ser Trp
    210                 215                 220

Arg Gly Gln Pro Thr Ile Ile Pro Leu Trp Thr Ser Ser Val His Ile
225                 230                 235                 240

Gly Gln Arg Trp Asn Leu Ser Thr Ser Asp Ile Thr Arg Val Cys Arg
                245                 250                 255

Leu Tyr Asn Cys Ser Arg Ser Val Pro Asp Ser His Gly Arg Gly Phe
            260                 265                 270

Glu Ala Gln Ser Asp Gly Ser Ser Leu Thr Pro Ala Ser Ile Ser Arg
        275                 280                 285

Leu Gln Arg Leu Leu Glu Ala Leu Ser Glu Glu Ser Gly Ser Ser Ala
```

```
                290                 295                 300
Pro Ser Gly Ser Arg Thr Gly Gly Gln Ser Ile Ala Gly Leu Gly Asn
305                 310                 315                 320

Ser Gln Gln Gly Trp Glu His Pro Pro Gln Ser Thr Phe Ser Val Gly
                325                 330                 335

Ala Leu Ala Arg Pro Pro Gln Met Leu Ala Asp Ala Ser Lys Ser Gly
                340                 345                 350

Pro Gly Ala Gly Ala Asp Ser Leu Ser Leu Glu Gln Phe Gln Leu Ala
            355                 360                 365

Gln Ala Pro Thr Val Pro Leu Ala Leu Phe Pro Glu Ala Arg Asp Lys
        370                 375                 380

Pro Ala Pro Ile Gln Asp Ala Phe Glu Arg Leu Ala Pro Leu Pro Gly
385                 390                 395                 400

Gly Cys Ala Pro Gly Ser His Ile Arg Glu Val Pro Arg Asp
                405                 410
```

<210> SEQ ID NO 7
<211> LENGTH: 1176
<212> TYPE: DNA
<213> ORGANISM: mus musculus

<400> SEQUENCE: 7

| | | | | | |
|---|---|---|---|---|---|
| atgggagcac | cctcagcatc | cagatgttct | ggagtctgca | gtaccagtgt | tccagaaggc | 60 |
| ttcactcctg | agggaagccc | ggtatttcag | gacaaggaca | tccccgcaat | taaccaaggg | 120 |
| ctcatctcag | aggagacccc | agaaagcagc | ttcctggtag | aagggacat | tatccggcca | 180 |
| ggggtcagcc | acggtgtgtc | tttcccagat | gaactcagcc | gccgggtcat | tatggatgcc | 240 |
| tttgctgagt | ttgaacgttt | cacatgcatc | cggtttgttg | cctaccatgg | tcagagagac | 300 |
| tttgtttcca | ttcttcctat | ggcggggtgt | ttctctggtg | tgggacgcag | tggagggatg | 360 |
| caggtggtgt | ccttggcacc | cacttgtctc | cggaagggcc | gaggcattgt | cctacatgag | 420 |
| ctcatgcacg | tacttggctt | ctggcatgag | cattcacggg | cagatcggga | ccgctacatc | 480 |
| caagtcaact | ggaacgagat | cctcccgggc | tttgaaatca | acttcatcaa | gtcacggagt | 540 |
| accaatatgt | tagttcccta | tgactactca | tctgtgatgc | attatgggag | atttgccttc | 600 |
| agctggcgtg | ggcagcccac | catcatacca | ctctggacct | ccagtgttca | cattggccag | 660 |
| cgatggaacc | tgagtacctc | agatatcacc | cgggtctgca | ggctgtataa | ctgcagccgg | 720 |
| agtgtccctg | actccacgg | gagagggttt | gaggcccaga | gtgatggaag | cagcctcacc | 780 |
| cctgcctcta | tatcacgtct | acaaagactt | ctcgaggcac | tgtcagagga | atctggaagc | 840 |
| tctgcccta | gtggctccag | gactggaggc | cagagtattg | ccgggcttgg | taacagccag | 900 |
| caaggatggg | agcatcctcc | tcagagcaca | ttcagtgtgg | agccttggc | aagaccacct | 960 |
| cagatgctag | ccgatgcttc | aaaatcgggg | cctggagcag | gtgcagacag | cttgtctcta | 1020 |
| gagcagttcc | agctagccca | ggccccacct | gtacctcttg | ctctatttcc | agaagccaga | 1080 |
| gacaagccag | cacctatcca | agatgccttt | gagaggctag | ctccacttcc | aggaggctgt | 1140 |
| gcacctggaa | gtcacattag | agaggtgccc | agagac | | | 1176 |

<210> SEQ ID NO 8
<211> LENGTH: 392
<212> TYPE: PRT
<213> ORGANISM: mus musculus

<400> SEQUENCE: 8

```
Met Gly Ala Pro Ser Ala Ser Arg Cys Ser Gly Val Cys Ser Thr Ser
1               5                   10                  15

Val Pro Glu Gly Phe Thr Pro Glu Gly Ser Pro Val Phe Gln Asp Lys
            20                  25                  30

Asp Ile Pro Ala Ile Asn Gln Gly Leu Ile Ser Glu Glu Thr Pro Glu
        35                  40                  45

Ser Ser Phe Leu Val Glu Gly Asp Ile Ile Arg Pro Gly Val Ser His
50                  55                  60

Gly Val Ser Phe Pro Asp Glu Leu Ser Arg Arg Val Ile Met Asp Ala
65                  70                  75                  80

Phe Ala Glu Phe Glu Arg Phe Thr Cys Ile Arg Phe Val Ala Tyr His
                85                  90                  95

Gly Gln Arg Asp Phe Val Ser Ile Leu Pro Met Ala Gly Cys Phe Ser
            100                 105                 110

Gly Val Gly Arg Ser Gly Gly Met Gln Val Val Ser Leu Ala Pro Thr
            115                 120                 125

Cys Leu Arg Lys Gly Arg Gly Ile Val Leu His Glu Leu Met His Val
            130                 135                 140

Leu Gly Phe Trp His Glu His Ser Arg Ala Asp Arg Asp Arg Tyr Ile
145                 150                 155                 160

Gln Val Asn Trp Asn Glu Ile Leu Pro Gly Phe Glu Ile Asn Phe Ile
                165                 170                 175

Lys Ser Arg Ser Thr Asn Met Leu Val Pro Tyr Asp Tyr Ser Ser Val
            180                 185                 190

Met His Tyr Gly Arg Phe Ala Phe Ser Trp Arg Gly Gln Pro Thr Ile
            195                 200                 205

Ile Pro Leu Trp Thr Ser Ser Val His Ile Gly Gln Arg Trp Asn Leu
210                 215                 220

Ser Thr Ser Asp Ile Thr Arg Val Cys Arg Leu Tyr Asn Cys Ser Arg
225                 230                 235                 240

Ser Val Pro Asp Ser His Gly Arg Gly Phe Glu Ala Gln Ser Asp Gly
            245                 250                 255

Ser Ser Leu Thr Pro Ala Ser Ile Ser Arg Leu Gln Arg Leu Leu Glu
            260                 265                 270

Ala Leu Ser Glu Glu Ser Gly Ser Ser Ala Pro Ser Gly Ser Arg Thr
            275                 280                 285

Gly Gly Gln Ser Ile Ala Gly Leu Gly Asn Ser Gln Gln Gly Trp Glu
            290                 295                 300

His Pro Pro Gln Ser Thr Phe Ser Val Gly Ala Leu Ala Arg Pro Pro
305                 310                 315                 320

Gln Met Leu Ala Asp Ala Ser Lys Pro Gly Pro Gly Ala Gly Ala Asp
            325                 330                 335

Ser Leu Ser Leu Glu Gln Phe Gln Leu Ala Gln Ala Pro Thr Val Pro
            340                 345                 350

Leu Ala Leu Phe Pro Glu Ala Arg Asp Lys Pro Ala Pro Ile Gln Asp
            355                 360                 365

Ala Phe Glu Arg Leu Ala Pro Leu Pro Gly Gly Cys Ala Pro Gly Ser
            370                 375                 380

His Ile Arg Glu Val Pro Arg Asp
385                 390

<210> SEQ ID NO 9
<211> LENGTH: 1140
<212> TYPE: DNA
```

<213> ORGANISM: mus musculus

<400> SEQUENCE: 9

```
atgggagcac cctcagcatc cagatgttct ggagtctgca gtaccagtgt tccagaaggc      60
ttcactcctg agggaagccc ggtatttcag gacaaggaca tccccgcaat taaccaaggg     120
ctcatctcag aggagacccc agaaagcagc ttcctgcttt ccagaaagta tgatgaactc     180
agccgccggg tcattatgga tgcctttgct gagtttgaac gtttcacatg catccggttt     240
gttgcctacc atggtcagag agactttgtt tccattcttc ctatggcggg tgtttctct     300
ggtgtgggac gcagtggagg gatgcaggtg gtgtccttgg cacccacttg tctccggaag     360
ggccgaggca ttgtcctaca tgagctcatg cacgtacttg gcttctggca tgagcattca     420
cgggcagatc gggaccgcta catccaagtc aactggaacg agatcctccc gggctttgaa     480
atcaacttca tcaagtcacg gagtaccaat atgttagttc cctatgacta ctcatctgtg     540
atgcattatg ggagatttgc cttcagctgg cgtgggcagc ccaccatcat accactctgg     600
acctccagtg ttcacattgg ccagcgatgg aacctgagta cctcagatat cacccgggtc     660
tgcaggctgt ataactgcag ccggagtgtc cctgactccc acgggagagg gtttgaggcc     720
cagagtgatg gaagcagcct caccctgcc tctatatcac gtctacaaag acttctcgag     780
gcactgtcag aggaatctgg aagctctgcc cctagtggct ccaggactgg aggccagagt     840
attgccgggc ttggtaacag ccagcaagga tgggagcatc tcctcagag cacattcagt     900
gtgggagcct tggcaagacc acctcagatg ctagccgatg cttcaaaatc ggggcctgga     960
gcaggtgcag acagcttgtc tctagagcag ttccagctag cccaggcccc cactgtacct    1020
cttgctctat ttccagaagc cagagacaag ccagcaccta tccaagatgc ctttgagagg    1080
ctagctccac ttccaggagg ctgtgcacct ggaagtcaca ttagagaggt gcccagagac    1140
```

<210> SEQ ID NO 10
<211> LENGTH: 380
<212> TYPE: PRT
<213> ORGANISM: Mus musculus

<400> SEQUENCE: 10

```
Met Gly Ala Pro Ser Ala Ser Arg Cys Ser Gly Val Cys Ser Thr Ser
1               5                   10                  15

Val Pro Glu Gly Phe Thr Pro Glu Gly Ser Pro Val Phe Gln Asp Lys
            20                  25                  30

Asp Ile Pro Ala Ile Asn Gln Gly Leu Ile Ser Glu Glu Thr Pro Glu
        35                  40                  45

Ser Ser Phe Leu Leu Ser Arg Lys Tyr Asp Glu Leu Ser Arg Arg Val
    50                  55                  60

Ile Met Asp Ala Phe Ala Glu Phe Glu Arg Phe Thr Cys Ile Arg Phe
65                  70                  75                  80

Val Ala Tyr His Gly Gln Arg Asp Phe Val Ser Ile Leu Pro Met Ala
                85                  90                  95

Gly Cys Phe Ser Gly Val Gly Arg Ser Gly Gly Met Gln Val Val Ser
            100                 105                 110

Leu Ala Pro Thr Cys Leu Arg Lys Gly Arg Gly Ile Val Leu His Glu
        115                 120                 125

Leu Met His Val Leu Gly Phe Trp His Glu His Ser Arg Ala Asp Arg
    130                 135                 140

Asp Arg Tyr Ile Gln Val Asn Trp Asn Glu Ile Leu Pro Gly Phe Glu
145                 150                 155                 160
```

```
Ile Asn Phe Ile Lys Ser Arg Ser Thr Asn Met Leu Val Pro Tyr Asp
            165                 170                 175
Tyr Ser Ser Val Met His Tyr Gly Arg Phe Ala Phe Ser Trp Arg Gly
            180                 185                 190
Gln Pro Thr Ile Ile Pro Leu Trp Thr Ser Ser Val His Ile Gly Gln
            195                 200                 205
Arg Trp Asn Leu Ser Thr Ser Asp Ile Thr Arg Val Cys Arg Leu Tyr
            210                 215                 220
Asn Cys Ser Arg Ser Val Pro Asp Ser His Gly Arg Gly Phe Glu Ala
225                 230                 235                 240
Gln Ser Asp Gly Ser Ser Leu Thr Pro Ala Ser Ile Ser Arg Leu Gln
            245                 250                 255
Arg Leu Leu Glu Ala Leu Ser Glu Gly Ser Gly Ser Ser Ala Pro Ser
            260                 265                 270
Gly Ser Arg Thr Gly Gly Gln Ser Ile Ala Gly Leu Gly Asn Ser Gln
            275                 280                 285
Gln Gly Trp Glu His Pro Pro Gln Ser Thr Phe Ser Val Gly Ala Leu
            290                 295                 300
Ala Arg Pro Pro Gln Met Leu Ala Asp Ala Ser Lys Ser Gly Pro Gly
305                 310                 315                 320
Ala Gly Ala Asp Ser Leu Ser Leu Glu Gln Phe Gln Leu Ala Gln Ala
            325                 330                 335
Pro Thr Val Pro Leu Ala Leu Phe Pro Glu Ala Arg Asp Lys Pro Ala
            340                 345                 350
Pro Ile Gln Asp Ala Phe Glu Arg Leu Ala Pro Leu Pro Gly Gly Cys
            355                 360                 365
Ala Pro Gly Ser His Ile Arg Glu Val Pro Arg Asp
            370                 375                 380

<210> SEQ ID NO 11
<211> LENGTH: 384
<212> TYPE: DNA
<213> ORGANISM: mus musculus

<400> SEQUENCE: 11
aaggtcttca gtcgctgtga gctggccaaa gagatgcatg acttcggtct ggatggctac      60
cggggttata acctggctga ctgggtctgc cttgcttact acacaagtgg cttcaacaca     120
aatgctgtgg atcatgaagc tgatggaagc accaacaatg catcttcca gatcagcagc     180 cggaggtggt gcagaaccct cgcctcgaat ggccccaatc tttgcaggat atactgcact     240
gatttgttga acaatgatct caaagattct atcgtctgtg ccatgaagat agttcaagaa     300
cccctgggtc tgggctattg ggaagcctgg aggcaccact gccagggcag ggacctcagt     360
gactgggtgg atggctgtga cttc                                            384

<210> SEQ ID NO 12
<211> LENGTH: 128
<212> TYPE: PRT
<213> ORGANISM: mus musculus

<400> SEQUENCE: 12

Lys Val Phe Ser Arg Cys Glu Leu Ala Lys Glu Met His Asp Phe Gly
1               5                   10                  15
Leu Asp Gly Tyr Arg Gly Tyr Asn Leu Ala Asp Trp Val Cys Leu Ala
            20                  25                  30
```

```
Tyr Tyr Thr Ser Gly Phe Asn Thr Asn Ala Val Asp His Glu Ala Asp
         35                  40                  45

Gly Ser Thr Asn Asn Gly Ile Phe Gln Ile Ser Ser Arg Arg Trp Cys
 50                  55                  60

Arg Thr Leu Ala Ser Asn Gly Pro Asn Leu Cys Arg Ile Tyr Cys Thr
 65                  70                  75                  80

Asp Leu Leu Asn Asn Asp Leu Lys Asp Ser Ile Val Cys Ala Met Lys
                 85                  90                  95

Ile Val Gln Glu Pro Leu Gly Leu Gly Tyr Trp Glu Ala Trp Arg His
                100                 105                 110

His Cys Gln Gly Arg Asp Leu Ser Asp Trp Val Asp Gly Cys Asp Phe
            115                 120                 125

<210> SEQ ID NO 13
<211> LENGTH: 820
<212> TYPE: DNA
<213> ORGANISM: mus musculus

<400> SEQUENCE: 13
gccctggcaa ggttgtgggg gacatcttga gctgaagcag ggttttgagc cactgctgct    60
gctgccattg tcaccatggt ctcagctctg cggggagcac ccctgatcag ggtgcactca   120
agccctgttt cttctccttc tgtgagtgga ccacggaggc tggtgagctg cctgtcatcc   180
caaagctcag ctctgagcca gagtggtggt ggctccacct ctgccgccgg catagaagcc   240
aggagcaggg ctctcagaag gcggtggtgc ccagctggga tcatgttgtt ggccctggtc   300
tgtctgctca gctgcctgct acctccagt gaggccaagc tctacggtcg ttgtgaactg   360
gccagagtgc tacatgactt cgggctggac ggataccggg gatacagcct ggctgactgg   420
gtctgccttg cttatttcac aagcggtttc aacgcagctg cttttggacta cgaggctgat   480 gggagcacca caacgggat cttccagatc aacagccgga ggtggtgcag caacctcacc   540
ccgaacgtcc ccaacgtgtg ccggatgtac tgctcagatt tgttgaatcc taatctcaag   600
gataccgtta tctgtgccat gaagataacc caagagcctc agggtctggg ttactgggag   660
gcctggaggc atcactgcca gggaaaagac ctcactgaat gggtggatgg ctgtgacttc   720
taggatggac ggaaccatgc acagcaggct gggaaatgtg gtttggttcc tgacctaggc   780
ttgggaagac aagccagcga ataaaggatg gttgaacgtt                         820

<210> SEQ ID NO 14
<211> LENGTH: 215
<212> TYPE: PRT
<213> ORGANISM: homo sapien

<400> SEQUENCE: 14

Met Val Ser Ala Leu Arg Gly Ala Pro Leu Ile Arg Val His Ser Ser
  1               5                  10                  15

Pro Val Ser Ser Pro Ser Val Ser Gly Pro Arg Arg Leu Val Ser Cys
                 20                  25                  30

Leu Ser Ser Gln Ser Ser Ala Leu Ser Gln Ser Gly Gly Gly Ser Thr
             35                  40                  45

Ser Ala Ala Gly Ile Glu Ala Arg Ser Arg Ala Leu Arg Arg Arg Trp
 50                  55                  60

Cys Pro Ala Gly Ile Met Leu Leu Ala Leu Val Cys Leu Leu Ser Cys
 65                  70                  75                  80

Leu Leu Pro Ser Ser Glu Ala Lys Leu Tyr Gly Arg Cys Glu Leu Ala
                 85                  90                  95
```

```
Arg Val Leu His Asp Phe Gly Leu Asp Gly Tyr Arg Gly Tyr Ser Leu
            100                 105                 110

Ala Asp Trp Val Cys Leu Ala Tyr Phe Thr Ser Gly Phe Asn Ala Ala
        115                 120                 125

Ala Leu Asp Tyr Glu Ala Asp Gly Ser Thr Asn Asn Gly Ile Phe Gln
    130                 135                 140

Ile Asn Ser Arg Arg Trp Cys Ser Asn Leu Thr Pro Asn Val Pro Asn
145                 150                 155                 160

Val Cys Arg Met Tyr Cys Ser Asp Leu Leu Asn Pro Asn Leu Lys Asp
                165                 170                 175

Thr Val Ile Cys Ala Met Lys Ile Thr Gln Glu Pro Gln Gly Leu Gly
            180                 185                 190

Tyr Trp Glu Ala Trp Arg His His Cys Gln Gly Lys Asp Leu Thr Glu
        195                 200                 205

Trp Val Asp Gly Cys Asp Phe
    210                 215

<210> SEQ ID NO 15
<211> LENGTH: 417
<212> TYPE: DNA
<213> ORGANISM: mus musculus

<400> SEQUENCE: 15
aagatttatg aacgctgtga gctggcaaag aagctggagg aggctggcct cgatggcttc      60
aaaggctata ctgttggaga ctggctgtgt gtggcacact atgagagtgg ctttgacacc     120
tcttttgtgg accacaatcc agatggcagc agtgaatatg gcattttcca gctgaactct     180
gcctggtggt gtaacaatgg catcacaccc actcagaacc tctgcaacat cgattgtaat     240
gacctgctca accgccatat tctggatgat atcatatgtg ccaagagggt tgcatcctca     300
cataagagta tgaaggcctg ggattcctgg acccagcact gtgccggtca tgatttatca     360
gaatggctaa aggggtgttc tgtgcgtctg aaaactgact caagctataa taactgg        417

<210> SEQ ID NO 16
<211> LENGTH: 139
<212> TYPE: PRT
<213> ORGANISM: mus musculus

<400> SEQUENCE: 16

Lys Ile Tyr Glu Arg Cys Glu Leu Ala Lys Lys Leu Glu Glu Ala Gly
1               5                   10                  15

Leu Asp Gly Phe Lys Gly Tyr Thr Val Gly Asp Trp Leu Cys Val Ala
            20                  25                  30

His Tyr Glu Ser Gly Phe Asp Thr Ser Phe Val Asp His Asn Pro Asp
        35                  40                  45

Gly Ser Ser Glu Tyr Gly Ile Phe Gln Leu Asn Ser Ala Trp Trp Cys
    50                  55                  60

Asn Asn Gly Ile Thr Pro Thr Gln Asn Leu Cys Asn Ile Asp Cys Asn
65                  70                  75                  80

Asp Leu Leu Asn Arg His Ile Leu Asp Asp Ile Ile Cys Ala Lys Arg
                85                  90                  95

Val Ala Ser Ser His Lys Ser Met Lys Ala Trp Asp Ser Trp Thr Gln
            100                 105                 110

His Cys Ala Gly His Asp Leu Ser Glu Trp Leu Lys Gly Cys Ser Val
        115                 120                 125
```

Arg Leu Lys Thr Asp Ser Ser Tyr Asn Asn Trp
    130                 135

<210> SEQ ID NO 17
<211> LENGTH: 588
<212> TYPE: DNA
<213> ORGANISM: homo sapien

<400> SEQUENCE: 17

```
ctgggagggc ttacaggtgc cataatgaag gcctggggca ctgtggtagt gaccttggcc      60
acgctgatgg ttgtcactgt ggatgccaag atctatgaac gctgcgagct ggcggcaaga     120
ctggagagag cagggctgaa cggctacaag ggctacggcg ttggagactg gctgtgcatg     180
gctcattatg agagtggctt tgacaccgcc ttcgtggacc acaatcctga tggcagcagt     240
gaatatggca ttttccaact gaattctgcc tggtggtgtg acaatggcat tacacccacc     300
aagaacctct gccacatgga ttgtcatgac ctgctcaatc gccatattct ggatgacatc     360
aggtgtgcca agcagattgt gtcctcacag aatgggcttt ctgcctggac ttcttggagg     420
ctacactgtt ctggccatga tttatctgaa tggctcaagg ggtgtgatat gcatgtgaaa     480
attgatccaa aaattcatcc atgactcaga ttcgaagaga cagattttat cttcctttca     540
tttctttctc ttgtgcattt aataaaggat ggtatctata aacaatgc                  588
```

<210> SEQ ID NO 18
<211> LENGTH: 159
<212> TYPE: PRT
<213> ORGANISM: homo sapien

<400> SEQUENCE: 18

Met Lys Ala Trp Gly Thr Val Val Thr Leu Ala Thr Leu Met Val
1               5                   10                  15

Val Thr Val Asp Ala Lys Ile Tyr Glu Arg Cys Glu Leu Ala Ala Arg
            20                  25                  30

Leu Glu Arg Ala Gly Leu Asn Gly Tyr Lys Gly Tyr Gly Val Gly Asp
        35                  40                  45

Trp Leu Cys Met Ala His Tyr Glu Ser Gly Phe Asp Thr Ala Phe Val
50                  55                  60

Asp His Asn Pro Asp Gly Ser Ser Glu Tyr Gly Ile Phe Gln Leu Asn
65                  70                  75                  80

Ser Ala Trp Trp Cys Asp Asn Gly Ile Thr Pro Thr Lys Asn Leu Cys
                85                  90                  95

His Met Asp Cys His Asp Leu Leu Asn Arg His Ile Leu Asp Asp Ile
            100                 105                 110

Arg Cys Ala Lys Gln Ile Val Ser Ser Gln Asn Gly Leu Ser Ala Trp
        115                 120                 125

Thr Ser Trp Arg Leu His Cys Ser Gly His Asp Leu Ser Glu Trp Leu
    130                 135                 140

Lys Gly Cys Asp Met His Val Lys Ile Asp Pro Lys Ile His Pro
145                 150                 155

<210> SEQ ID NO 19
<211> LENGTH: 435
<212> TYPE: PRT
<213> ORGANISM: mus musculus

<400> SEQUENCE: 19

Met Gly Ile Met Gly Ser Leu Trp Pro Trp Ile Leu Thr Met Leu Ser
1               5                   10                  15

```
Leu Leu Gly Leu Ser Met Gly Ala Pro Ser Ala Ser Arg Cys Ser Gly
            20                  25                  30

Val Cys Ser Thr Ser Val Pro Glu Gly Phe Thr Pro Glu Gly Ser Pro
        35                  40                  45

Val Phe Gln Asp Lys Asp Ile Pro Ala Ile Asn Gln Gly Leu Ile Ser
 50                  55                  60

Glu Glu Thr Pro Glu Ser Ser Phe Leu Val Glu Gly Asp Ile Ile Arg
 65                  70                  75                  80

Pro Ser Pro Phe Arg Leu Leu Ser Val Thr Asn Asn Lys Trp Pro Lys
                85                  90                  95

Gly Val Gly Gly Phe Val Glu Ile Pro Phe Leu Leu Ser Arg Lys Tyr
                100                 105                 110

Asp Glu Leu Ser Arg Arg Val Ile Met Asp Ala Phe Ala Glu Phe Glu
            115                 120                 125

Arg Phe Thr Cys Ile Arg Phe Val Ala Tyr His Gly Gln Arg Asp Phe
        130                 135                 140

Val Ser Ile Leu Pro Met Ala Gly Cys Phe Ser Gly Val Gly Arg Ser
145                 150                 155                 160

Gly Gly Met Gln Val Val Ser Leu Ala Pro Thr Cys Leu Arg Lys Gly
                165                 170                 175

Arg Gly Ile Val Leu His Glu Leu Met His Val Leu Gly Phe Trp His
            180                 185                 190

Glu His Ser Arg Ala Asp Arg Asp Arg Tyr Ile Gln Val Asn Trp Asn
        195                 200                 205

Glu Ile Leu Pro Gly Phe Glu Ile Asn Phe Ile Lys Ser Arg Ser Thr
210                 215                 220

Asn Met Leu Val Pro Tyr Asp Tyr Ser Ser Val Met His Tyr Gly Arg
225                 230                 235                 240

Phe Ala Phe Ser Trp Arg Gly Gln Pro Thr Ile Ile Pro Leu Trp Thr
                245                 250                 255

Ser Ser Val His Ile Gly Gln Arg Trp Asn Leu Ser Thr Ser Asp Ile
            260                 265                 270

Thr Arg Val Cys Arg Leu Tyr Asn Cys Ser Arg Ser Val Pro Asp Ser
        275                 280                 285

His Gly Arg Gly Phe Glu Ala Gln Ser Asp Gly Ser Ser Leu Thr Pro
    290                 295                 300

Ala Ser Ile Ser Arg Leu Gln Arg Leu Leu Glu Ala Leu Ser Glu Glu
305                 310                 315                 320

Ser Gly Ser Ser Ala Pro Ser Gly Ser Arg Thr Gly Gly Gln Ser Ile
                325                 330                 335

Ala Gly Leu Gly Asn Ser Gln Gln Gly Trp Glu His Pro Pro Gln Ser
            340                 345                 350

Thr Phe Ser Val Gly Ala Leu Ala Arg Pro Pro Gln Met Leu Ala Asp
        355                 360                 365

Ala Ser Lys Ser Gly Pro Gly Ala Gly Ala Asp Ser Leu Ser Leu Glu
    370                 375                 380

Gln Phe Gln Leu Ala Gln Ala Pro Thr Val Pro Leu Ala Leu Phe Pro
385                 390                 395                 400

Glu Ala Arg Asp Lys Pro Ala Pro Ile Gln Asp Ala Phe Glu Arg Leu
                405                 410                 415

Ala Pro Leu Pro Gly Gly Cys Ala Pro Gly Ser His Ile Arg Glu Val
            420                 425                 430
```

```
Pro Arg Asp
        435

<210> SEQ ID NO 20
<211> LENGTH: 401
<212> TYPE: PRT
<213> ORGANISM: mus musculus

<400> SEQUENCE: 20

Met Gly Ile Met Gly Ser Leu Trp Pro Trp Ile Leu Thr Met Leu Ser
1               5                   10                  15

Leu Leu Gly Leu Ser Met Gly Ala Pro Ser Ala Ser Arg Cys Ser Gly
            20                  25                  30

Val Cys Ser Thr Ser Val Pro Glu Gly Phe Thr Pro Glu Gly Ser Pro
        35                  40                  45

Val Phe Gln Asp Lys Asp Ile Pro Ala Ile Asn Gln Gly Leu Ile Ser
    50                  55                  60

Glu Glu Thr Pro Glu Ser Ser Phe Leu Leu Ser Arg Lys Tyr Asp Glu
65                  70                  75                  80

Leu Ser Arg Arg Val Ile Met Asp Ala Phe Ala Glu Phe Glu Arg Phe
                85                  90                  95

Thr Cys Ile Arg Phe Val Ala Tyr His Gly Gln Arg Asp Phe Val Ser
            100                 105                 110

Ile Leu Pro Met Ala Gly Cys Phe Ser Gly Val Gly Arg Ser Gly Gly
        115                 120                 125

Met Gln Val Val Ser Leu Ala Pro Thr Cys Leu Arg Lys Gly Arg Gly
    130                 135                 140

Ile Val Leu His Glu Leu Met His Val Leu Gly Phe Trp His Glu His
145                 150                 155                 160

Ser Arg Ala Asp Arg Asp Arg Tyr Ile Gln Val Asn Trp Asn Glu Ile
                165                 170                 175

Leu Pro Gly Phe Glu Ile Asn Phe Ile Lys Ser Arg Ser Thr Asn Met
            180                 185                 190

Leu Val Pro Tyr Asp Tyr Ser Ser Val Met His Tyr Gly Arg Phe Ala
        195                 200                 205

Phe Ser Trp Arg Gly Gln Pro Thr Ile Ile Pro Leu Trp Thr Ser Ser
    210                 215                 220

Val His Ile Gly Gln Arg Trp Asn Leu Ser Thr Ser Asp Ile Thr Arg
225                 230                 235                 240

Val Cys Arg Leu Tyr Asn Cys Ser Arg Ser Val Pro Asp Ser His Gly
                245                 250                 255

Arg Gly Phe Glu Ala Gln Ser Asp Gly Ser Ser Leu Thr Pro Ala Ser
            260                 265                 270

Ile Ser Arg Leu Gln Arg Leu Leu Glu Ala Leu Ser Glu Glu Ser Gly
        275                 280                 285

Ser Ser Ala Pro Ser Gly Ser Arg Thr Gly Gly Gln Ser Ile Ala Gly
    290                 295                 300

Leu Gly Asn Ser Gln Gln Gly Trp Glu His Pro Gln Ser Thr Phe
305                 310                 315                 320

Ser Val Gly Ala Leu Ala Arg Pro Pro Gln Met Leu Ala Asp Ala Ser
                325                 330                 335

Lys Ser Gly Pro Gly Ala Gly Ala Asp Ser Leu Ser Leu Glu Gln Phe
            340                 345                 350

Gln Leu Ala Gln Ala Pro Thr Val Pro Leu Ala Leu Phe Pro Glu Ala
        355                 360                 365
```

Arg Asp Lys Pro Ala Pro Ile Gln Asp Ala Phe Glu Arg Leu Ala Pro
            370                 375                 380

Leu Pro Gly Gly Cys Ala Pro Gly Ser His Ile Arg Glu Val Pro Arg
385                 390                 395                 400

Asp

<210> SEQ ID NO 21
<211> LENGTH: 413
<212> TYPE: PRT
<213> ORGANISM: mus musculus

<400> SEQUENCE: 21

Met Gly Ile Met Gly Ser Leu Trp Pro Trp Ile Leu Thr Met Leu Ser
1               5                   10                  15

Leu Leu Gly Leu Ser Met Gly Ala Pro Ser Ala Ser Arg Cys Ser Gly
            20                  25                  30

Val Cys Ser Thr Ser Val Pro Glu Gly Phe Thr Pro Glu Gly Ser Pro
        35                  40                  45

Val Phe Gln Asp Lys Asp Ile Pro Ala Ile Asn Gln Gly Leu Ile Ser
    50                  55                  60

Glu Glu Thr Pro Glu Ser Ser Phe Leu Val Glu Gly Asp Ile Ile Arg
65                  70                  75                  80

Pro Gly Val Ser His Gly Val Ser Phe Pro Asn Glu Leu Ser Arg Arg
                85                  90                  95

Val Ile Met Asp Ala Phe Ala Glu Phe Glu Arg Phe Thr Cys Ile Arg
            100                 105                 110

Phe Val Ala Tyr His Gly Gln Arg Asp Phe Val Ser Ile Leu Pro Met
        115                 120                 125

Ala Gly Cys Phe Ser Gly Val Gly Arg Ser Gly Gly Met Gln Val Val
    130                 135                 140

Ser Leu Ala Pro Thr Cys Leu Arg Lys Gly Arg Gly Ile Val Leu His
145                 150                 155                 160

Glu Leu Met His Val Leu Gly Phe Trp His Glu His Ser Arg Ala Asp
                165                 170                 175

Arg Asp Arg Tyr Ile Gln Val Asn Trp Asn Glu Ile Leu Pro Gly Phe
            180                 185                 190

Glu Ile Asn Phe Ile Lys Ser Arg Ser Thr Asn Met Leu Val Pro Tyr
        195                 200                 205

Asp Tyr Ser Ser Val Met His Tyr Gly Arg Phe Ala Phe Ser Trp Arg
    210                 215                 220

Gly Gln Pro Thr Ile Ile Pro Leu Trp Thr Ser Ser Val His Ile Gly
225                 230                 235                 240

Gln Arg Trp Asn Leu Ser Thr Ser Asp Ile Thr Arg Val Cys Arg Leu
                245                 250                 255

Tyr Asn Cys Ser Arg Ser Val Pro Asp Ser His Gly Arg Gly Phe Glu
            260                 265                 270

Ala Gln Ser Asp Gly Ser Ser Leu Thr Pro Ala Ser Ile Ser Arg Leu
        275                 280                 285

Gln Arg Leu Leu Glu Ala Leu Ser Glu Glu Ser Gly Ser Ser Ala Pro
    290                 295                 300

Ser Gly Ser Arg Thr Gly Gly Gln Ser Ile Ala Gly Leu Gly Asn Ser
305                 310                 315                 320

Gln Gln Gly Trp Glu His Pro Pro Gln Ser Thr Phe Ser Val Gly Ala
                325                 330                 335

Leu Ala Arg Pro Pro Gln Met Leu Ala Asp Ala Ser Lys Ser Gly Pro
            340                 345                 350

Gly Ala Gly Ala Asp Ser Leu Ser Leu Glu Gln Phe Gln Leu Ala Gln
        355                 360                 365

Ala Pro Thr Val Pro Leu Ala Leu Phe Pro Glu Ala Arg Asp Lys Pro
370                 375                 380

Ala Pro Ile Gln Asp Ala Phe Glu Arg Leu Ala Pro Leu Pro Gly Gly
385                 390                 395                 400

Cys Ala Pro Gly Ser His Ile Arg Glu Val Pro Arg Asp
                405                 410

<210> SEQ ID NO 22
<211> LENGTH: 1296
<212> TYPE: DNA
<213> ORGANISM: homo sapiens

<400> SEQUENCE: 22

| | | | | | |
|---|---|---|---|---|---|
| atggagggtg | taggggtct | ctggccttgg | gtgctgggtc | tgctctcctt | gccaggtgtg | 60 |
| atcctaggag | cgccctggc | ctccagctgc | gcaggagcct | gtggtaccag | cttcccagat | 120 |
| ggcctcaccc | ctgagggaac | ccaggcctcc | ggggacaagg | acattcctgc | aattaaccaa | 180 |
| gggctcatcc | tggaagaaac | cccagagagc | agcttcctca | tcgagggga | catcatccgg | 240 |
| ccgagtccct | tccgactgct | gtcagcaacc | agcaacaaat | ggcccatggg | tggtagtggt | 300 |
| gtcgtggagg | tccccttcct | gctctccagc | aagtacgatg | agcccagccg | ccaggtcatc | 360 |
| ctggaggctc | ttgcggagtt | tgaacgttcc | acgtgcatca | ggtttgtcac | ctatcaggac | 420 |
| cagagagact | tcatttccat | catccccatg | tatgggtgct | ctcgagtgt | ggggcgcagt | 480 |
| ggagggatgc | aggtggtctc | cctggcgccc | acgtgtctcc | agaagggccg | ggcattgtc | 540 |
| cttcatgagc | tcatgcatgt | gctgggcttc | tggcacgagc | acacgcgggc | cgaccgggac | 600 |
| cgctatatcc | gtgtcaactg | gaacgagatc | ctgccaggct | tgaaatcaa | cttcatcaag | 660 |
| tctcagagca | gcaacatgct | gacgccctat | gactactcct | ctgtgatgca | ctatgggagg | 720 |
| ctcgccttca | gccggcgtgg | gctgcccacc | atcacaccac | tttgggcccc | cagtgtccac | 780 |
| atcggccagc | gatggaacct | gagtgcctcg | gacatcaccc | gggtcctcaa | actctacggc | 840 |
| tgcagcccaa | gtggcccag | gccccgtggg | agagggtccc | atgcccacag | cactggtagg | 900 |
| agccccgctc | cggcctccct | atctctgcag | cggcttttgg | aggcactgtc | ggcggaatcc | 960 |
| aggagcccg | accccagtgg | ttccagtgcg | ggaggccagc | ccgttcctgc | agggcctggg | 1020 |
| gagagcccac | atgggtggga | gtcccctgcc | ctgaaaaagc | tcagtgcaga | ggcctcggca | 1080 |
| aggcagcctc | agaccctagc | ttcctcccca | agatcaaggc | ctggagcagg | tgcccccggt | 1140 |
| gttgctcagg | agcagtcctg | gctggccgga | gtgtccacca | gcccacagt | cccatcttca | 1200 |
| gaagcaggaa | tccagccagt | ccctgtccag | ggaagcccag | ctctgccagg | gggctgtgta | 1260 |
| cctagaaatc | atttcaaggg | gatgtccgaa | gattaa | | | 1296 |

<210> SEQ ID NO 23
<211> LENGTH: 431
<212> TYPE: PRT
<213> ORGANISM: homo sapiens

<400> SEQUENCE: 23

Met Glu Gly Val Gly Gly Leu Trp Pro Trp Val Leu Gly Leu Leu Ser
1               5                   10                  15

-continued

```
Leu Pro Gly Val Ile Leu Gly Ala Pro Leu Ala Ser Ser Cys Ala Gly
             20                  25                  30

Ala Cys Gly Thr Ser Phe Pro Asp Gly Leu Thr Pro Glu Gly Thr Gln
         35                  40                  45

Ala Ser Gly Asp Lys Asp Ile Pro Ala Ile Asn Gln Gly Leu Ile Leu
     50                  55                  60

Glu Glu Thr Pro Glu Ser Ser Phe Leu Ile Glu Gly Asp Ile Ile Arg
 65                  70                  75                  80

Pro Ser Pro Phe Arg Leu Leu Ser Ala Thr Ser Asn Lys Trp Pro Met
                 85                  90                  95

Gly Gly Ser Gly Val Val Glu Val Pro Phe Leu Leu Ser Ser Lys Tyr
            100                 105                 110

Asp Glu Pro Ser Arg Gln Val Ile Leu Glu Ala Leu Ala Glu Phe Glu
        115                 120                 125

Arg Ser Thr Cys Ile Arg Phe Val Thr Tyr Gln Asp Gln Arg Asp Phe
    130                 135                 140

Ile Ser Ile Ile Pro Met Tyr Gly Cys Phe Ser Ser Val Gly Arg Ser
145                 150                 155                 160

Gly Gly Met Gln Val Val Ser Leu Ala Pro Thr Cys Leu Gln Lys Gly
                165                 170                 175

Arg Gly Ile Val Leu His Glu Leu Met His Val Leu Gly Phe Trp His
            180                 185                 190

Glu His Thr Arg Ala Asp Arg Asp Arg Tyr Ile Arg Val Asn Trp Asn
        195                 200                 205

Glu Ile Leu Pro Gly Phe Glu Ile Asn Phe Ile Lys Ser Gln Ser Ser
    210                 215                 220

Asn Met Leu Thr Pro Tyr Asp Tyr Ser Ser Val Met His Tyr Gly Arg
225                 230                 235                 240

Leu Ala Phe Ser Arg Arg Gly Leu Pro Thr Ile Thr Pro Leu Trp Ala
                245                 250                 255

Pro Ser Val His Ile Gly Gln Arg Trp Asn Leu Ser Ala Ser Asp Ile
            260                 265                 270

Thr Arg Val Leu Lys Leu Tyr Gly Cys Ser Pro Ser Gly Pro Arg Pro
        275                 280                 285

Arg Gly Arg Gly Ser His Ala His Ser Thr Gly Arg Ser Pro Ala Pro
    290                 295                 300

Ala Ser Leu Ser Leu Gln Arg Leu Leu Glu Ala Leu Ser Ala Glu Ser
305                 310                 315                 320

Arg Ser Pro Asp Pro Ser Gly Ser Ala Gly Gly Gln Pro Val Pro
                325                 330                 335

Ala Gly Pro Gly Glu Ser Pro His Gly Trp Glu Ser Pro Ala Leu Lys
            340                 345                 350

Lys Leu Ser Ala Glu Ala Ser Ala Arg Gln Pro Gln Thr Leu Ala Ser
        355                 360                 365

Ser Pro Arg Ser Arg Pro Gly Ala Gly Ala Pro Gly Val Ala Gln Glu
    370                 375                 380

Gln Ser Trp Leu Ala Gly Val Ser Thr Lys Pro Thr Val Pro Ser Ser
385                 390                 395                 400

Glu Ala Gly Ile Gln Pro Val Pro Val Gln Gly Ser Pro Ala Leu Pro
                405                 410                 415

Gly Gly Cys Val Pro Arg Asn His Phe Lys Gly Met Ser Glu Asp
            420                 425                 430
```

```
<210> SEQ ID NO 24
<211> LENGTH: 11
<212> TYPE: PRT
<213> ORGANISM: mus musculus

<400> SEQUENCE: 24

His Glu Leu Met His Val Leu Gly Phe Trp His
1               5                   10

<210> SEQ ID NO 25
<211> LENGTH: 5
<212> TYPE: PRT
<213> ORGANISM: mus musculus

<400> SEQUENCE: 25

Ser Val Met His Tyr
1               5

<210> SEQ ID NO 26
<211> LENGTH: 11
<212> TYPE: PRT
<213> ORGANISM: mus musculus
<220> FEATURE:
<221> NAME/KEY: MISC_FEATURE
<223> OTHER INFORMATION: The X represents possible amino acid residue
      substitution with other amino acids
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 26

His Glu Xaa Xaa His Xaa Xaa Gly Xaa Xaa His
1               5                   10

<210> SEQ ID NO 27
<211> LENGTH: 5
<212> TYPE: PRT
<213> ORGANISM: mus musculus
<220> FEATURE:
<221> NAME/KEY: UNSURE
<222> LOCATION: (1)..(5)
<223> OTHER INFORMATION: X indicates the site of possible amino acid
      substitution

<400> SEQUENCE: 27

Ser Xaa Met His Tyr
1               5

<210> SEQ ID NO 28
<211> LENGTH: 24
<212> TYPE: DNA
<213> ORGANISM: Homo sapiens

<400> SEQUENCE: 28
gcgcccctgg cctccagctg cgca                                          24

<210> SEQ ID NO 29
<211> LENGTH: 24
<212> TYPE: DNA
<213> ORGANISM: homo sapiens
```

```
<400> SEQUENCE: 29
cacgacacca ctaccaccca tggg                                          24

<210> SEQ ID NO 30
<211> LENGTH: 24
<212> TYPE: DNA
<213> ORGANISM: homo sapiens

<400> SEQUENCE: 30
ggctgcagcc caagtggccc cagg                                          24

<210> SEQ ID NO 31
<211> LENGTH: 24
<212> TYPE: DNA
<213> ORGANISM: homo sapiens

<400> SEQUENCE: 31
agcaacaccg ggggcacctg ctcc                                          24

<210> SEQ ID NO 32
<211> LENGTH: 24
<212> TYPE: DNA
<213> ORGANISM: homo sapiens

<400> SEQUENCE: 32
gaggtcccct tcctgctctc cagc                                          24

<210> SEQ ID NO 33
<211> LENGTH: 24
<212> TYPE: DNA
<213> ORGANISM: homo sapiens

<400> SEQUENCE: 33
ggcatgggac cctctcccac gggg                                          24
```

COMPOSITIONS AND METHODS FOR DETECTING, DIAGNOSING, AND TREATING CANCER

CROSS REFERENCE TO RELATED APPLICATIONS

This application is a national stage of International Application No. PCT/US2011/046905, filed Aug. 8, 2011, which claims priority under 35 U.S.C. §119(e) to U.S. Provisional Application Ser. No. 61/371,215 filed Aug. 6, 2010, U.S. Provisional Application Ser. No. 61/423,302 filed Dec. 15, 2010, and U.S. Provisional Application Ser. No. 61/499,448 filed Jun. 21, 2011, the disclosures of which are incorporated by reference in their entirety herein.

STATEMENT REGARDING FEDERALLY SPONSORED RESEARCH OR DEVELOPMENT

This invention was made in part with United States Government support under Grant Nos. R03HD055129 awarded by the NIH and D43 TW/HD 00654 from the Fogarty International Center. The United States Government has certain rights in the invention.

BACKGROUND

The astacin family of metalloendopeptidases was recognized as a novel family of proteases in the 1990s. The astacins are a subfamily of the metzincin superfamily of metalloproteinases. The first to be characterized was the crayfish enzyme astacin. To date more than 200 members of this family have been identified in species ranging from bacteria to humans. Astacins are involved in developmental morphogenesis, matrix assembly, tissue differentiation, and digestion. Family members include the procollagen C-proteinase (BMP1, bone morphogenetic protein 1), tolloid and mammalian tolloid-like, HMP (Hydra vulgaris metalloproteinase), sea urchin BP10 (blastula protein) and SPAN (Strongylocentrotus purpuratus astacin), the 'hatching' subfamily comprising alveolin, ovastacin, LCE, HCE ('low' and 'high' choriolytic enzymes), nephrosin (from carp head kidney), UVS.2 from frog, and the meprins. In the human and mouse genomes, there are six astacin family genes (two meprins, three BMP1/tolloid-like, one ovastacin), but in *Caenorhabditis elegans* there are 40.

Astacin family members are characterized by a unique 18-amino acid signature sequence, which begins with a five-amino acid zinc-binding motif found in most metalloendopeptidases (See review by Bond and Benyon, 1995). The signature sequence is part of an approximately 200-amino acid sequence, which is the entire mature crayfish astacin and the catalytic or protease domain of all the members of the family. Signal and prosequences are also common features of family member, with the possible exception of QuCAM-1; these NH2-terminal domains have yet to be found for this latter protein. Astacin, which until recently was only studied as a mature protein that begins with the protease domain, is now known to contain a prepro segment of 49 residues. The transient signal peptides direct the proteins into the endoplasmic reticulum during biosynthesis, which is consistent with the finding that all of the proteins of the family studied thus far are secreted or plasma membrane bound. The prosequences vary greatly in size, containing up to 519 amino acids for *Drosophila* tolloid-related-1 (DrT/r-1), and are likely to be important for regulating activity and perhaps expression of the proteases. Regarding the latter point, for example, the large prosequence of DrT/r-1 has been suggested to prevent expression of this gene product in early stages of embryogenesis when cell cycles are very short.

Meprins are zinc-dependent, membrane-bound proteases and members of the "astacin family" of metalloproteinases (Bond and Beynon, 1995, Protein Sci. 4: 1247-1261; Sterchi et al., 2008, Molecular Aspects of Medicine, 29:309-328). The enzymes are multidomain, oligomeric proteins. The expression is highly regulated on the transcriptional and translational level. Typically, the proteins are targeted to apical membranes of polarized epithelial cells (Eldering et al., Eur. J. Biochem. 247: 920-932, 1997). Various growth factors, cytokines, and extracellular matrix proteins are substrates for meprins. Meprins have been identified in leukocytes, cancer cells and intestine and kidney. Both the meprin α and β genes are expressed in various cancer cells. In colorectal tumour tissue meprin α mRNA, immunoreactive protein and enzymatic activity is detected. In contrast to normal colon, however, the meprin α subunit is secreted into the stroma of the tumor where it accumulates and can be detected by immuno-histochemical methods. The mechanism of this aberrant secretion was shown using a colon adenocarcinoma cell line (Caco-2) expressing meprin α endogenously. When cultured on transwell filter supports meprin is equally secreted from the apical and the basolateral membrane domains. On the basolateral side of the epithelial cell layer, meprin α may be activated by plasmin, which is generated from plasminogen by an activation process catalyzed by uPA from intestinal fibroblasts (Rösmann et al., 2002). Meprin expression may play a role in tumor cell invasion and migration and in doing so may be involved in tumor progression (Sterchi et al., 2008; Rosmann et al., 2002, J. Biol. Chem., 277:43:40650-40658).

Quesada et al. (2004, J. Biol. Chem., 279:25:26627-26634) isolated a novel protein from mouse and human and because of its predominant expression in ovarian tissues and apparent similarity to astacins named it "ovastacin". Quesada was looking for candidate metalloproteinases involved in the process of embryo hatching and used the BLAST algorithm to look for novel astacin metalloproteinases. They discovered and sequenced a novel protein in mouse and human and localized the gene in humans to human chromosome 2q11.1. Computer analysis revealed an N-terminal signal peptide, a zinc-dependent metalloprotease domain, and a prodomain possibly involved in maintaining protease latency. However, ovastacin was found to have an additional 150 amino acid C-terminal domain not found in other astacins. Quesada et al. also showed that the protein has metalloprotease activity, and that it was expressed in no normal tissues other than ovary. They suggested that its normal function of ovastacin might be similar to the astacin family "hatching enzymes" of lower species. Additionally, they found that it was expressed in some cancer cells, including lymphoma and leukemia cells lines, but only two of five ovarian carcinomas tested, and that was only detectable using RT-PCR. Other groups have more recently referred to ovastacin as "Astacin Like protein" (ASTL).

At about the same time Quesada discovered "ovastacin", another group isolated it and referred to it at first as Zinc Endopeptidase (ZEP) (Mandal et al., published on Aug. 31, 2006, PCT Pat. Pub. No. WO 2006/091535) and later as Sperm Acrosomal SLLP1 Receptor ("SAS1R"), because it was an oocyte protein that they found interacted with the sperm protein SLLP1 (Mandal et al., 2008, Biol. of Reproduction, 78:69:72; Herr et al., PCT Pat. Pub. No. WO 2010/054187, published May 14, 2010).

Mandal et al., (PCT Pat. Pub. No. WO 2006/091535) showed that ZEP had 2 variants, a sequence indicating a predicted transmembrane domain, a cleavage site, and a zinc binding signature. They pointed out that it was homologous to the hatching enzyme EHE7 of the Japanese eel *Anguilla japonica* and hypothesized that it may be performing a similar function in mouse embryo development. The bioinformatic analysis of Mandal showed that the protein has two glycosylation sites, phosphorylation sites, and myristylation sites. They noted that the sites were suggestive of a membrane protein and that transmembrane topology also predicted a strong transmembrane domain at the N-terminal of the protein. Their data showed that it was egg specific, and that it localized on the egg surface in the microvillar region, but was developmentally regulated. The data also suggested interactions between ZEP and the sperm surface protein SLLP1.

In Mandal et al. (Biology of Reproduction, 78:69-72, 2008), the group began referring to ZEP as SAS1R. They found that SAS1R localized on the microvillar domain of mature live oocytes and was significantly lost after fertilization, being virtually undetectable in blastocysts. They showed that transfection of CHO-K1 cells with a full length SAS1R cDNA construct allowed the protein to be expressed on the surface of non-permeabilized cells, indicating the presence of an active transmembrane domain. They also described protease characteristics and the ability of SAS1R to act as the receptor for the sperm protein SLLP1.

Herr et al. (PCT Pat. Pub. No. WO 2010/054187; published on May 14, 2010) found that: native SAS1R showed binding to recombinant SLLP1 using the surface plasmon resonance technique; bound recombinant SAS1R captured recombinant SLLP1 in a membrane overlay assay (Far Western analyses); SAS1R and SLLP1 revealed molecular binding properties by yeast two hybrid analysis; immunoprecipitation of recombinant SAS1R recovered recombinant SLLP1 and immunoprecipitated recombinant SLLP1 recovered recombinant SAS1R from rabbit reticulocyte extract; recombinant SLLP1 binds to oocyte microvillar domain and co-localizes with native SAS1R; recombinant SAS1R binds to acrosome of sperm and co-localizes with native SLLP1; native SLLP1 from sperm acrosomal matrix localizes with native SAS1R; and native SAS1R and native SLLP1 are co-precipitated from mixtures of non-ionic detergent extracts of oocytes and sperm. Herr et al. also showed that SAS1R is localized on live human eggs retrieved for in vitro fertilization and that administration of exogenous SAS1R to a subject elicits an immune response against SAS1R. They also demonstrated that SAS1R protein first arises in bilaminar secondary follicles during postnatal oogenesis, in pubertal oogenesis, as well as adult oogenesis. The pattern is uniform irrespective of the age of the animal. In adult mouse ovaries, SAS1R staining is restricted to oocytes within secondary follicles and all subsequent stages. Primordial oocytes and primary oocytes do not stain for SAS1R at any developmental stage. They found that the only cell type in the ovary that stained for SAS1R was oocytes and that the presence of SAS1R was developmentally regulate.

The American Cancer Society (ACS) predicts 43,470 new cases of uterine cancer in 2010 and 7,950 deaths in the U.S. There are no screening assays for early detection and monitoring of uterine cancer. A form of uterine cancer known as malignant mixed Mullerian tumors (MMMTs) is of interest because this type of uterine cancer occurs predominantly in post-menopausal women. MMMTs are a particularly aggressive cancer and patients do poorly. MMMTs account for approximately 10% of endometrial malignancies.

Worldwide, ovarian cancer (CaO) is the leading cause of death from gynecological cancer and the fourth most common cause of cancer death in women. In 2010, ACS estimates 20,180 new cases of CaO will be diagnosed in the United States and 15,310 women will die from the disease. High death rates result from the difficulty associated with detecting CaO at an early stage and the lack of effective therapies to treat advanced disease.

Given the lack of definitive diagnostic tests for cancer such as ovarian and uterine cancers, and the poor prognosis for patients with metastatic disease, there is a long felt need in the art for diagnostic tests for these and other cancers.

There is a long felt need in the art to identify and use cancer biomarkers and to find methods to regulate these biomarkers, including targeting the biomarker for treatment and prevention of cancer. The present invention satisfies these needs.

SUMMARY OF THE INVENTION

The present invention provides compositions and methods useful for diagnosing, treating, and preventing cancer, based on the unexpected result disclosed herein that the oocyte protein, SAS1R, is expressed in multiple types of cancers and is expressed at the cell surface, thus making SAS1R the first cancer-oocyte antigen/biomarker discovered. Cancer-oocyte antigens/biomarkers are defined as proteins expressed among normal tissues only in the oocyte and only at specific stages of folliculogenesis. The expression of a cell surface protein, normally restricted to the oocyte, in various tumors offers striking opportunities for a tumor selective therapy when accompanied by a companion diagnostic to identify subjects expressing the cancer-oocyte antigen target. Therefore, SAS1R is a useful biomarker for detecting and diagnosing cancer.

Based on the data disclosed herein, SAS1R meets the key criteria for use as a cancer diagnostic biomarker and as a therapeutic target. Among adult tissues, SAS1R is expressed only in oocytes, and at a precise stage of folliculogenesis, and is disclosed herein to be expressed in several kinds of tumors, and is in fact found at the cell surface. Importantly, SAS1R has been disclosed herein to be a cell surface protein accessible to antibody binding on the exoplasmic face of the plasma membrane of oocytes and tumor cells. Therefore, it is useful as a diagnostic biomarker. Also disclosed herein is the ability to kill cancer cells expressing SAS1R by targeting cell surface SAS1R. Therefore, SAS1R is a target for drug therapy or as a vaccinogen. SAS1R is also an active enzyme, and as such is potentially a target for drugs and other agents to inhibit its activity, and its catalytic pocket may be targeted to deliver cytotoxic drugs that act intracellularly. Because SAS1R's expression is stage specific during folliculogenesis and is not localized in primordial and the majority of primary follicles, therapeutic targeting of SAS1R in females is predicted to spare the population of quiescent oocytes in the ovary that serve as the ovarian reserve. Thus, therapies that target SAS1R in tumors may avoid the induction of infertility in females. Because SAS1R expression is restricted among normal tissues to the oocyte in females, when a man's tumor expresses SAS1R, the protein's presence at the cell surface offers a remarkable opportunity for tumor selective therapy.

In one embodiment, the present invention provides compositions and methods for diagnosing cancer in a subject, comprising detecting the presence of SAS1R in a biological sample from the subject, wherein the presence of SAS1R in the sample indicates that the subject has cancer. In one aspect, the subject is a human.

In one embodiment, the present invention provides compositions and methods useful for detecting and measuring SAS1R cDNA, protein, miRNA, or mRNA.

In one embodiment, detection comprises the steps described herein and further comprises analyzing the results with an analytical device and program. In one aspect, the analytical device comprises a computer. In one aspect, the analytical device comprises a sequence analyzer.

In one embodiment, the level of detected SAS1R cDNA, protein, miRNA, or mRNA is quantified with an analytical device and program. In one aspect, the level of detected SAS1R is compared with the level in a control sample.

In one embodiment, the sample is selected from the group consisting of tumor biopsy, tissue sample, blood, plasma, peritoneal fluid, follicular fluid, ascites, urine, feces, saliva, mucus, phlegm, sputum, tears, cerebrospinal fluid, effusions, lavage, and Pap smears. In one aspect, the sample is blood. In one aspect, the sample is serum. In one aspect, the sample is plasma.

In one embodiment, SAS1R protein, miRNA, or mRNA is detected using a method selected from the group consisting of ELISA, immunoassay, immunofluorescence, immunohistochemistry, immunoprecipitation, northern blot, western blot, dot blot, PCR, and surface plasmon resonance.

In one embodiment, SAS1R protein, or fragments thereof, can be detected at levels as low as 1 pg/ml. In one aspect, SAS1R protein, or fragments thereof, can be detected at levels as low as 10 pg/ml. In one aspect, SAS1R protein, or fragments thereof, can be detected at levels as low as 50 pg/ml. In one aspect, SAS1R protein, or fragments thereof, can be detected at levels as low as 100 pg/ml. In one aspect, SAS1R protein, or fragments thereof, can be detected at levels as low as 500 pg/ml. In one aspect, SAS1R protein, or fragments thereof, can be detected at levels as low as 1 ng/ml. In one aspect, SAS1R protein, or fragments thereof, can be detected at levels as low as 5 ng/ml. In one aspect, SAS1R protein, or fragments thereof, can be detected at levels as low as 10 ng/ml. In one aspect, SAS1R protein, or fragments thereof, can be detected at levels as low as 20 ng/ml.

In one aspect, the SAS1R protein is a cell surface protein. In one aspect, SAS1R protein is detected on the surface of a cell.

In one embodiment, the cancer being diagnosed or detected is selected from the group consisting of carcinoma, sarcoma, uterine cancer, ovarian cancer, lung cancer, adenocarcinoma, adenocarcinoma of the lung, squamous carcinoma, squamous carcinoma of the lung, malignant mixed mullerian tumor, leukemia, lymphoma, and endometrioid carcinoma.

In one embodiment, SAS1R is detected using PCR. In one aspect, the sample is a tumor biopsy. In another aspect, the sample comprises tumor cells. In one aspect, the PCR is performed using primers selected from the group consisting of SEQ ID NOs:28-33. In one embodiment, the present invention provides novel primers for PCR. In one aspect, six primers are provided. In one aspect, the primers are selected from the group of primer having SEQ ID NOs:28-33.

In one embodiment, SAS1R protein is detected using an antibody, or a fragment or homolog thereof, directed against SAS1R. In one aspect, the antibody binds to one or more SAS1R protein fragments selected from the group consisting of amino acids 1-25, 26-50, 51-75, 76-100, 101-125, 126-150, 151-175, 176-200, 201-225, 226-250, 251-275, 276-300, 301-325, 326-350, 351-375, 376-400, 401-425, and 426-431 of SAS1R human variant 1 (SEQ ID NO:23). In one aspect, the antibody binds to one or more SAS1R protein fragments selected from the group consisting of amino acids 1-20, 21-40, 41-60, 61-80, 81-100, 101-120, 121-140, 141-160, 161-180, 181-200, 201-220, 221-240, 241-260, 261-280, 281-300, 301-320, 321-340, 341-360, 361-380, 381-400, 401-420, 421-431, and 411-431 of SAS1R human variant 1 (SEQ ID NO:23).

In one embodiment, the antibody is selected from the group consisting of a single chain antibody, a monoclonal antibody, a bi-specific antibody, a chimeric antibody, a synthetic antibody, a polyclonal antibody, a humanized antibody, a fully human antibody, and active fragments or homologs thereof. In one aspect, an antibody of the invention, or a fragment or homolog thereof, binds to an epitope of SAS1R, or a fragment or homolog thereof. In one aspect, the epitope is selected from a fragment of SAS1R, selected from group consisting of amino acids 1-25, 26-50, 51-75, 76-100, 101-125, 126-150, 151-175, 176-200, 201-225, 226-250, 251-275, 276-300, 301-325, 326-350, 351-375, 376-400, 401-425, 426-431, 1-20, 21-40, 41-60, 61-80, 81-100, 101-120, 121-140, 141-160, 161-180, 181-200, 201-220, 221-240, 241-260, 261-280, 281-300, 301-320, 321-340, 341-360, 361-380, 381-400, 401-420, 421-431, and 411-431 of SAS1R human variant 1 (SEQ ID NO:23).

The present invention also provides compositions and methods for monitoring the progression or treatment of a SAS1R positive cancer in a subject. In one embodiment, the method comprises detecting SAS1R in a sample and determining the level of SAS1R in the sample, then comparing the level of SAS1R in that sample with a standard or with a previous level of SAS1R from that subject, wherein a change in the level in the sample from that subject correlates with the progression or treatment of the SAS1R positive cancer in the subject. In one aspect, the SAS1R being detected and quantified is SAS1R protein, miRNA, or mRNA. In one aspect, the detection comprises analyzing the results with an analytical device or system and a computer program. In one aspect, the results are quantified. In one aspect, the analytical device or system comprises a computer. In one aspect, the analytical device comprises a sequence analyzer. In one aspect, the level of detected SAS1R protein, miRNA, or mRNA is quantified with an analytical device and program. In one aspect, the level of detected SAS1R is compared with the level in a control sample.

In one embodiment, the sample being used to monitor the progression or treatment of a SAS1R positive cancer is selected from the group consisting of tumor biopsy, tissue sample, blood, plasma, peritoneal fluid, follicular fluid, ascites, urine, feces, saliva, mucus, phlegm, sputum, tears, cerebrospinal fluid, effusions, lavage, and Pap smears. In one aspect, the SAS1R protein, miRNA or mRNA is detected using a method selected from the group consisting of ELISA, immunoassay, immunofluorescence, immunohistochemistry, immunoprecipitation, northern blot, western blot, dot blot, PCR, and surface plasmon resonance.

The present invention further provides compositions and methods for detecting and localizing SAS1R positive cancer in a subject. In one embodiment, the present invention provides for administering to a subject a composition, wherein the composition includes a complex comprising an imaging agent and a molecule which binds to SAS1R, optionally said complex further comprising a linker or spacer, and detecting the imaging agent. In one aspect, the molecule that binds to SAS1R is a protein. In one aspect, the protein that binds to SAS1R is SLLP1 or a fragment or homolog thereof. In one aspect, the SLLP1 protein has the sequence of SEQ ID NO:14. In one aspect, the protein that binds to SAS1R is an antibody, or a fragment or homolog thereof. In one aspect, the antibody is selected from the group consisting of a single chain antibody, a monoclonal antibody, a bi-specific antibody, a chimeric antibody, a synthetic antibody, a polyclonal antibody, or a humanized antibody, or active fragments or homologs thereof.

In one embodiment, the monoclonal antibodies directed against SAS1R are selected from the group consisting of SB1, SB2, SB3, SB4, and SB5. The invention further provides hybridomas comprising SB1, SB2, SB3, SB4, and SB5, respectively. The present invention further provides isolated nucleic acids comprising nucleic acid sequences encoding the monoclonal antibodies SB1, SB2, SB3, SB4, and SB5, respectively. In one aspect, the antibodies are humanized.

In one embodiment, the imaging agent is selected from the group consisting of a radionuclide, a radiological contrast agent, a paramagnetic ion, a metal, a biological tag, a fluorescent label, a chemiluminescent label, an ultrasound contrast agent and a photoactive agent. In one aspect, the radionuclide is selected from the group consisting of $^{110}$In, $^{111}$In, $^{177}$Lu, $^{18}$F, $^{52}$Fe, $^{62}$Cu, $^{64}$Cu, $^{67}$Cu, $^{67}$Cu, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52}$mM, $^{55}$Co, $^{72}$As, $^{75}$Br, $^{76}$Br, $^{82}$mRb, $^{83}$Sr, and other gamma-, beta-, or positron-emitters. In one aspect, the imaging agent is detected with a PET or SPECT/CT scanner coupled to a computer, and analyzing imaging data using a program. In one aspect, the method detects the location of the cancer in the subject. In one aspect, the invention provides for detecting and imaging a cancer which has metastasized, i.e., the method can detect cancer in multiple locations in the same subject.

The present invention further provides compositions and methods useful for personalized medicine. In one embodiment, the present invention provides compositions and methods useful for selecting a subject with cancer who will be responsive to treatment with an antagonist or inhibitor of SAS1R, comprising detecting the presence of SAS1R protein, miRNA or mRNA in a sample from the subject, wherein the presence of SAS1R protein, miRNA or mRNA in the sample indicates that the subject will be responsive to treatment with an antagonist or inhibitor of SAS1R.

The present invention also provides compositions and methods useful for preventing and for treating SAS1R positive cancer. In one embodiment, the invention provides a vaccine for preventing cancer. In one embodiment, the present invention provides compositions and methods for inducing an immunogenic response against SAS1R protein, or a fragment thereof. In one aspect, the method comprises administering to a subject a pharmaceutical composition comprising an immunogenic amount of SAS1R protein, or an immunogenic fragment or homolog thereof. In one aspect, the SAS1R protein or fragment or homolog thereof has a sequence selected from SEQ ID NOs:6, 8, 10, 19, 20, 21, and 23.

In one embodiment, the invention comprises administering to a subject an isolated nucleic acid comprising a sequence encoding a SAS1R protein or an immunogenic fragment or homolog thereof. In one aspect, the isolated nucleic acid has a sequence selected from SEQ ID NOs:5, 7, 9, and 22.

In one embodiment, a method for treating SAS1R positive cancer comprises administering to a subject in need thereof an effective amount of an antagonist or inhibitor of SAS1R, thereby treating a SAS1R positive cancer. In one aspect, the antagonist or inhibitor inhibits SAS1R activity, levels, and expression. In one aspect, the inhibitor or antagonist binds with SAS1R protein.

In one embodiment, the inhibitor or antagonist are selected from the group consisting of antibodies and fragments and homologs thereof directed against SAS1R, drugs, therapeutic agents, antisense oligonucleotides, aptamers, phylomers, and proteins.

In one embodiment, the antibody is selected from the group consisting of a single chain antibody, a monoclonal antibody, a bi-specific antibody, a chimeric antibody, a synthetic antibody, a polyclonal antibody, or a humanized antibody, or active fragments or homologs thereof. In one aspect, the antibody binds to one or more SAS1R protein fragments selected from the group consisting of amino acids 1-25, 26-50, 51-75, 76-100, 101-125, 126-150, 151-175, 176-200, 201-225, 226-250, 251-275, 276-300, 301-325, 326-350, 351-375, 376-400, 401-425, and 426-431 of SAS1R human variant 1 (SEQ ID NO:23). In one aspect, the antibody binds to one or more SAS1R protein fragments selected from the group consisting of amino acids 1-20, 21-40, 41-60, 61-80, 81-100, 101-120, 121-140, 141-160, 161-180, 181-200, 201-220, 221-240, 241-260, 261-280, 281-300, 301-320, 321-340, 341-360, 361-380, 381-400, 401-420, 421-431, and 411-431 of SAS1R human variant 1 (SEQ ID NO:23).

In one embodiment, the protein inhibitor or antagonist is SLLP1, or a fragment or homolog thereof. In one aspect SLLP1 has the sequence of SEQ ID NO:14.

The present invention further provides compositions and methods for killing cancer cells and for inhibiting proliferation of cancer cells. The method for inhibiting proliferation or killing a SAS1R positive cancer cell comprises contacting said cancer cell with an effective amount of antibody directed against SAS1R or a fragment thereof, wherein the antibody directed against SAS1R or a fragment thereof binds with SAS1R, thereby inhibiting proliferation or killing a cancer cell. In one embodiment, the killing is antibody-mediated complement-dependent cell killing. In one aspect, complement is supplemented. In one embodiment, the invention provides compositions and methods for lysing cancer cells with polyclonal or monoclonal antibodies directed against SAS1R, or fragments thereof, in the presence of complement. In one embodiment, the cancer cell being killed or inhibited from proliferating is selected from the group consisting of carcinoma, sarcoma, uterine cancer, ovarian cancer, lung cancer, adenocarcinoma, adenocarcinoma of the lung, squamous carcinoma, squamous carcinoma of the lung, malignant mixed mullerian tumor, leukemia, lymphoma, and endometrioid carcinoma. In one aspect, the antibody is conjugated to another molecule or structure. In one aspect, the other molecule or structure is selected from the group consisting of an antibody, a protein, a pro-drug, a drug, a toxin, a protein toxin, a liposome, a radioactive isotope, and an enzyme.

The invention further provides kits for diagnosing, detecting, imaging, and treating SAS1R positive cancers.

Because the present disclosure is the first to disclose the existence of an cancer-oocyte antigen, the present application encompasses targeting not just SAS1R, but all other cancer-oocyte antigens that will be useful for diagnosing and treating cancers expressing cancer-oocyte antigens other than SAS1R. Therefore, the present application encompasses compositions and methods for detecting cancer-oocyte antigens and for preventing, diagnosing, and treating cancer-oocyte antigen positive cancers. Such compositions and methods are provided herein or disclosed in the art.

Various aspects and embodiments of the invention are described in further detail below.

BRIEF DESCRIPTION OF THE DRAWINGS

FIG. 1 depicts a summary of studies demonstrating that mouse SAS1R expression is specifically restricted to the ovary (specifically fertilized ovum, oocyte, unfertilized ovum, and zygote) based on a mouse SAS1R expression profile from EST database. Human, dog, cat and rabbit have been tested with similar results (data not shown).

FIG. 3 represents a human SAS1R expression profile from an EST database.

FIG. 20, comprising panels A-D, provides the Actin (A), DAPI (B), FITC (C) and Merged (D) images for the immune staining of MMMT 5399.

DETAILED DESCRIPTION

Figure 2:
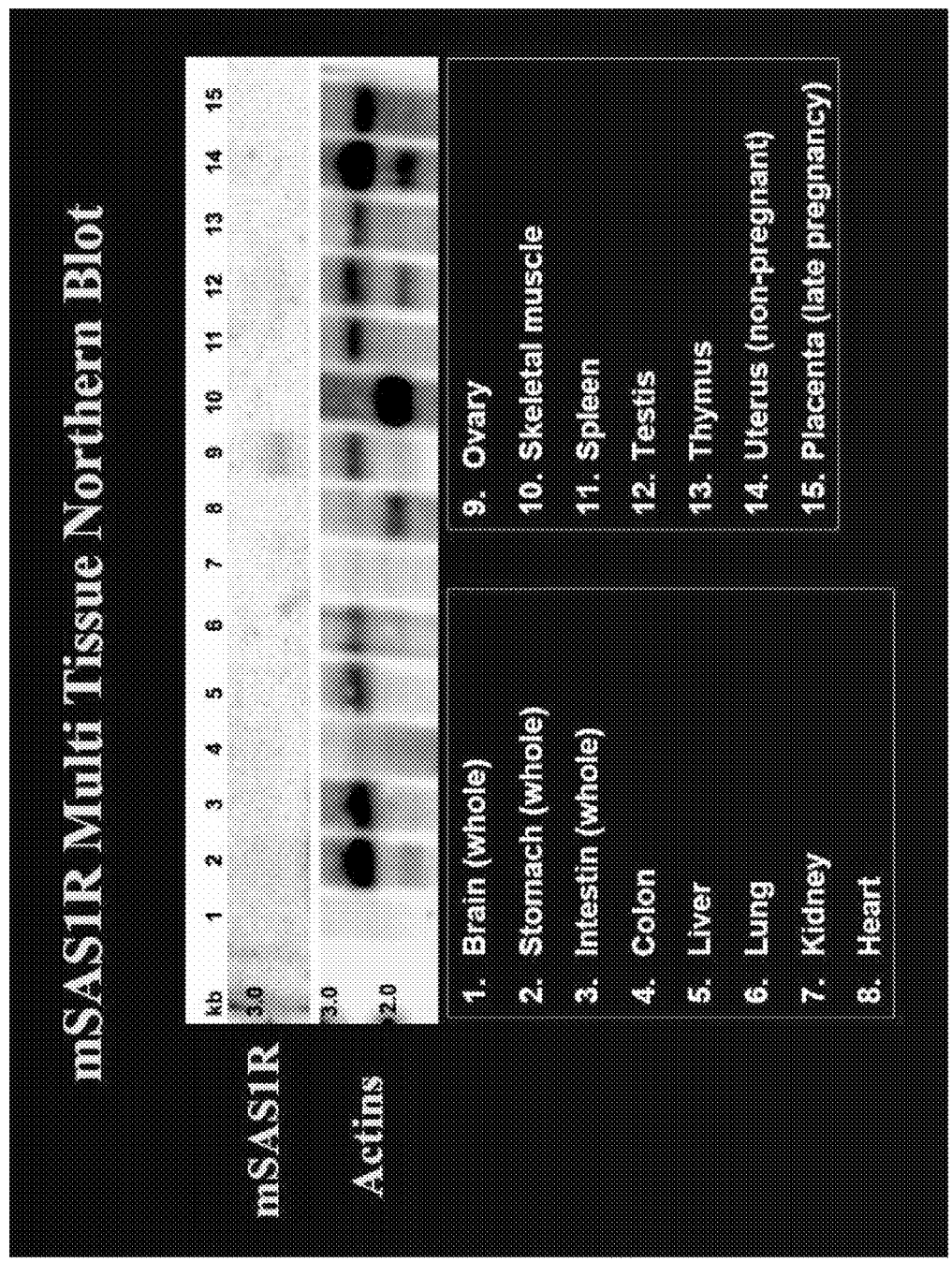
FIG. 2 provides images of a Northern blot analysis of mouse SAS1R expression in a multi-tissue northern blot further demonstrated its restricted expression in ovary relative to brain, stomach, intestine, colon, liver lung, kidney, heart, skeletal muscle, spleen, testis, uterus, and placenta. The upper panel represents mSAS1R expression and the lower panel is a control for actin.

Abbreviations and Acronyms a.a.—amino acid(s)
ADEPT—antibody-directed enzyme prodrug therapy
ASTL—astacin-like protein; this name is now commonly used and accepted and refers to the same protein also referred to as ovastacin, ZEP, SAS1R and SAS1B
BSA—bovine serum albumin
CDC—complement-dependent cytotoxicity
Co-IP—co-immunoprecipitation
FITC—fluorescein isothiocyanate FRET—fluorescence resonance energy transfer
FW—Far Western
GV—germinal vesicle
h—human (also hour)
HEK—human embryonic kidney
HPLC—reversed-phase high-pressure liquid chromatography
HS—high stringency
I—induced or immune
IF—Indirect immunofluorescence
IP—immunoprecipitation
IPTG—Isopropyl-β-D-thiogalactopyranoside
LB—Luria broth
LC/MS means liquid chromatography/mass spectrometry
LNA—locked nucleic acids
LS—low stringency
IM—immune
m—mouse
MET—mouse egg-specific TolA (referred to in the provisional application as a Colcin-like uptake protein or Colicin uptake protein)
min—minute
miRNA—microRNA
MMMT—malignant mixed mullerian tumor
NGS—normal goat serum
OL—overlay
P—purified
PI—pre-immune
PBS—phosphate-buffered saline
PBST—phosphate buffered saline with 0.05% Tween 20
PVA—polyvinylalcohol
rec—recombinant (rec is used interchangeably with "r")
SAS1R—Sperm Acrosomal SLLP1 Receptor; previously referred to as ZEP and originally discovered and called "Ovastacin" by Quesada et al.; also referred to as SAS1B; the gene encoding SAS1R is referred to as ASTL
rSAS1R—recombinant SAS1R
sec—second(s)
SLLP—sperm lysozyme-like protein
SPECT—single photon emission computed tomography
SPR—surface plasmon resonance
U—uninduced
ZEP—zinc endopeptidase (referred to in the provisional application as zinc peptidase, or ZP; used interchangeably with SAS1R, SAS1B, ovastacin and ASTL)
ZFE—zona free egg
ZIE—zona intact egg Summary of SEQ ID NOs. Used and the Matching Names SEQ ID NOs SEQ ID NO:1—mouse ("m") MET normal nucleic acid sequence
SEQ ID NO:2—mouse MET normal amino acid sequence
SEQ ID NO:3—mouse MET variant nucleic acid sequence
SEQ ID NO:4—mouse MET variant amino acid sequence
SEQ ID NO:5—mouse SAS1R Variant 2 Normal nucleic acid sequence (formerly called ZEP-Normal)
SEQ ID NO:6—mouse SAS1R Variant 2 Normal amino acid sequence (formerly called ZEP-Normal)
SEQ ID NO:7—mouse SAS1R Variant 5 nucleic acid sequence (formerly called ZEP Variant 1)
SEQ ID NO:8—mouse SAS1R Variant 5 amino acid sequence (formerly called ZEP Variant 1)
SEQ ID NO:9—mouse SAS1R Variant 3 nucleic acid sequence (formerly called ZEP Variant 2)
SEQ ID NO:10—mouse SAS1R Variant 3 amino acid sequence (formerly called ZEP Variant 2)
SEQ ID NO:11—mouse SLLP1 nucleic acid sequence
SEQ ID NO:12—mouse SLLP1 amino acid sequence
SEQ ID NO:13—human ("h") SLLP1 nucleic acid sequence
SEQ ID NO:14—human SLLP1 amino acid sequence
SEQ ID NO:15—mouse SLLP2 nucleic acid sequence
SEQ ID NO:16—mouse SLLP2 mature protein amino acid sequence
SEQ ID NO:17—human SLLP2 nucleic acid sequence
SEQ ID NO:18—human SLLP2 amino acid sequence
SEQ ID NO:19—mouse SAS1R Variant 1 amino acid sequence
SEQ ID NO:20—mouse SAS1R Variant 4 amino acid sequence
SEQ ID NO:21—mouse SAS1R Variant 6 amino acid sequence
SEQ ID NO:22—human SAS1R nucleic acid sequence (GenBank accession no. NM_001002036, 1296 bp mRNA)
SEQ ID NO:23—human SAS1R amino acid sequence (GenBank accession no. NP_001002036.3, 431 amino acids)
SEQ ID NO:24—HELMHVLGFWH (motif in SAS1R with histidine residues for Zn coordination and conserved catalytic residue, E [glutamic acid], forms part of the catalytic pocket along with a tyrosine zinc ligand embedded in the motif SVMHY (SEQ ID NO:25).
SEQ ID NO:25—SVMHY (motif in SAS1R associated with the catalytic pocket)
SEQ ID NO:26—HEXXHXXGXXH (the consensus motif of SEQ ID NO:24 can have residues which can be substituted with any amino acid, as indicated by "X", that does not ablate the function of that motif).
SEQ ID NO:27—SXMHY (the consensus motif of SEQ ID NO:25 can have residues which can be substituted with any amino acid, as indicated by "X", that does not ablate the function of that motif).

```
                                              SEQ ID NO: 28
1F primer-
GCGCCCCTGGCCTCCAGCTGCGCA SEQ ID NO: 29
2R primer-
CACGACACCACTACCACCCATGGG SEQ ID NO: 30
3F primer-
GGCTGCAGCCCAAGTGGCCCCAGG SEQ ID NO: 31
4R primer-
AGCAACACCGGGGGCACCTGCTCC SEQ ID NO: 32
5F primer-
GAGGTCCCCTTCCTGCTCTCCAGC SEQ ID NO: 33
6R primer-
GGCATGGGACCCTCTCCCACGGGG.
```

SEQ ID NOs:1-18 are the same sequences as SEQ ID NOs:1-18 of international patent application WO 2006/091535 (PCT/US2006/005970; Mandal et al.; published Aug. 31, 2006), in which SAS1R was referred to as ZEP. WO 2006/091535 is incorporated by reference in its entirety herein.

SEQ ID NOs: 1-27 are the same 27 sequences used in international patent application PCT/US/2009/063540 (Herr et al.), filed Nov. 6, 2009, published on May 14, 2010 as WO 2010/054187. A U.S. application (Ser. No. 12/613,947) claiming priority to the PCT application published on 7/22/10 as Pub. No. US 2010/0183617.

SEQ ID NOs: 28-33 are novel primers for detecting SAS1R.

DEFINITIONS

In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the term "adjuvant" refers to a substance that elicits an enhanced immune response when used in combination with a specific antigen.

As use herein, the terms "administration of" and or "administering" a compound should be understood to mean providing a compound of the invention or a prodrug of a compound of the invention to a subject in need of treatment.

As used herein, the term "aerosol" refers to suspension in the air. In particular, aerosol refers to the particlization or atomization of a formulation of the invention and its suspension in the air.

As used herein, an "agonist" is a composition of matter which, when administered to a mammal such as a human, enhances or extends a biological activity attributable to the level or presence of a target compound or molecule of interest in the mammal.

An "antagonist" is a composition of matter which when administered to a mammal such as a human, inhibits a biological activity attributable to the level or presence of a compound or molecule of interest in the mammal.

As used herein, "alleviating a disease or disorder symptom," means reducing the severity of the symptom or the frequency with which such a symptom is experienced by a patient, or both.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

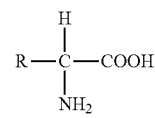

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

An "aptamer" is a compound that is selected in vitro to bind preferentially to another compound (for example, the identified proteins herein). Often, aptamers are nucleic acids or peptides because random sequences can be readily generated from nucleotides or amino acids (both naturally occurring or synthetically made) in large numbers but of course they need not be limited to these.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

As used herein, the term "biologically active fragments" or "bioactive fragment" of the polypeptides encompasses natural or synthetic portions of the full-length protein that are capable of specific binding to their natural ligand or of performing the function of the protein.

The term "biological sample," as used herein, refers to samples obtained from a subject, including, but not limited to, skin, hair, tissue, blood, plasma, cells, sweat and urine.

"C19" and "C23" are names which are also used for "SLLP1" and SLLP2".

The term "cancer", as used herein, is defined as proliferation of cells whose unique trait—loss of normal controls—results in unregulated growth, lack of differentiation, local tissue invasion, and metastasis. Examples include but are not limited to, melanoma, breast cancer, prostate cancer, ovarian cancer, uterine cancer, cervical cancer, skin cancer, pancreatic cancer, colorectal cancer, renal cancer and lung cancer.

As used herein, the term "carrier molecule" refers to any molecule that is chemically conjugated to the antigen of interest that enables an immune response resulting in antibodies specific to the native antigen.

The term "cell surface protein" means a protein found where at least part of the protein is exposed at the outer aspect of the cell membrane. Examples include growth factor receptors.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A "compound," as used herein, refers to any type of substance or agent that is commonly considered a drug, or a candidate for use as a drug, as well as combinations and mixtures of the above.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

As used herein, a "derivative" of a compound refers to a chemical compound that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, the term "diagnosis" refers to detecting aberrant SAS1R expression due to cancers expressing SAS1R. In any method of diagnosis exist false positives and false negatives. Any one method of diagnosis does not provide 100% accuracy.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used herein, the term "effector domain" refers to a domain capable of directly interacting with an effector molecule, chemical, or structure in the cytoplasm which is capable of regulating a biochemical pathway.

As used herein, the phrases "egg protein" or "egg-specific protein" refer to proteins which are expressed exclusively or predominately in eggs or ovaries. The proteins need not be expressed at all stages of egg or ovarian development.

The term "elixir," as used herein, refers in general to a clear, sweetened, alcohol-containing, usually hydroalcoholic liquid containing flavoring substances and sometimes active medicinal agents.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As used herein, a "functional" biological molecule is a biological molecule in a form in which it exhibits a property by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator using the BLAST tool at the NCBI website. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

By the term "immunizing a subject against an antigen" is meant administering to the subject a composition, a protein complex, a DNA encoding a protein complex, an antibody or a DNA encoding an antibody, which elicits an immune response in the subject, and, for example, provides protection to the subject against a disease caused by the antigen or which prevents the function of the antigen.

The term "immunologically active fragments thereof" will generally be understood in the art to refer to a fragment of a polypeptide antigen comprising at least an epitope, which means that the fragment at least comprises 4 contiguous amino acids from the sequence of the polypeptide antigen.

As used herein, the term "induction of apoptosis" means a process by which a cell is affected in such a way that it begins the process of programmed cell death, which is characterized by the fragmentation of the cell into membrane-bound particles that are subsequently eliminated by the process of phagocytosis.

As used herein, the term "inhaler" refers both to devices for nasal and pulmonary administration of a drug, e.g., in solution, powder and the like. For example, the term "inhaler" is intended to encompass a propellant driven inhaler, such as is used to administer antihistamine for acute asthma attacks, and plastic spray bottles, such as are used to administer decongestants.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

By "interaction" between a sperm protein and an egg protein is meant the interaction such as binding which is necessary for an event or process to occur, such as sperm-egg binding, fusion, or fertilization. In one aspect, the "interaction" may be similar to receptor-ligand type of binding or interaction.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds to a target receptor.

A "receptor" is a compound that specifically binds to a ligand.

A ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, New York) for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

"Malexpression" of a gene means expression of a gene in a cell of a patient afflicted with a disease or disorder, wherein the level of expression (including non-expression), the portion of the gene expressed, or the timing of the expression of the gene with regard to the cell cycle, differs from expression of the same gene in a cell of a patient not afflicted with the disease or disorder. It is understood that malexpression may cause or contribute to the disease or disorder, be a symptom of the disease or disorder, or both.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

The term "nasal administration" in all its grammatical forms refers to administration of at least one compound of the invention through the nasal mucous membrane to the bloodstream for systemic delivery of at least one compound of the invention. The advantages of nasal administration for delivery are that it does not require injection using a syringe and needle, it avoids necrosis that can accompany intramuscular administration of drugs, and trans-mucosal administration of a drug is highly amenable to self administration.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

An "oocyte" as used herein can be categorized more specifically several ways. A "naked oocyte" is defined as a female germ cell that is not surrounded by a continuous sheet of nurse granulose cells. A "primordial oocyte" is defined as a female germ cell that is surrounded by a single layer of squamous nurse granulosa cells. A "primary oocyte" is defined as a female germ cell that is surrounded by a single layer of cuboidal nurse granulose cells. A "secondary oocyte" is defined as a female germ cell that is surrounded by two layers of cuboidal granulose cells. A "preeantral oocyte" is defined as a female germ cell that is surrounded by three or more layers of granulose cells but without an antral space. An "antral oocyte" is defined as a female germ cell that is surrounded by three or more layers of granulosa cells and contains evidence of antral fluid spaces.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

The term "per application" as used herein refers to administration of a drug or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

As used herein, "pharmaceutical compositions" include formulations for human and veterinary use.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

By "presensitization" is meant pre-administration of at least one innate immune system stimulator prior to challenge with an agent. This is sometimes referred to as induction of tolerance.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A "prophylactic" treatment is a treatment administered to a subject who does not exhibit signs of a disease or exhibits only early signs of the disease for the purpose of decreasing the risk of developing pathology associated with the disease.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., The Peptides, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA. A "significant detectable level" is an amount of contaminate that would be visible in the presented data and would need to be addressed/explained during analysis of the forensic evidence.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

A "receptor" is a compound that specifically binds to a ligand.

A "ligand" is a compound that specifically binds to a target receptor.

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

The term "regulate" refers to either stimulating or inhibiting a function or activity of interest.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, *Methods for General and Molecular Bacteriology*, American Society for Microbiology, Washington, D.C., p. 574).

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

The term "SAS1R positive cancer" as used herein refers to a cancer wherein cells of the cancer express SAS1R.

"SLLP1" and "SLLP2" are also referred to as "C19" and "C23", respectively.

As used herein, the term "secondary antibody" refers to an antibody that binds to the constant region of another antibody (the primary antibody).

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this invention.

As used herein, a "substantially homologous amino acid sequences" includes those amino acid sequences which have at least about 95% homology, preferably at least about 96% homology, more preferably at least about 97% homology, even more preferably at least about 98% homology, and most preferably at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm.

The default settings used for these programs are suitable for identifying substantially similar amino acid sequences for purposes of the present invention.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M NaPO$_4$, 1 mM EDTA at 50° C. with washing in 2× standard saline citrate (SSC), 0.1% SDS at 50° C.; preferably in 7% (SDS), 0.5 M NaPO$_4$, 1 mM EDTA at 50° C. with washing in 1×SSC, 0.1% SDS at 50° C.; preferably 7% SDS, 0.5 M NaPO$_4$, 1 mM EDTA at 50° C. with washing in 0.5×SSC, 0.1% SDS at 50° C.; and more preferably in 7% SDS, 0.5 M NaPO$_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215: 3:403-10; Altschul et al., 1997 Nucleic Acids Res. 25:3389-3402). The default settings provided with these programs are suitable for determining substantial similarity of nucleic acid sequences for purposes of the present invention.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "transgenic mammal" means a mammal, the germ cells of which comprise an exogenous nucleic acid.

As used herein, a "transgenic cell" is any cell that comprises a nucleic acid sequence that has been introduced into the cell in a manner that allows expression of a gene encoded by the introduced nucleic acid sequence.

The term to "treat," as used herein, means reducing the frequency with which symptoms are experienced by a patient or subject or administering an agent or compound to reduce the frequency with which symptoms are experienced.

A "prophylactic" treatment is a treatment administered to a subject who does not exhibit signs of a disease or exhibits only early signs of the disease for the purpose of decreasing the risk of developing pathology associated with the disease.

By the term "vaccine," as used herein, is meant a composition which when inoculated into a subject has the effect of stimulating an immune response in the subject, which serves to fully or partially protect the subject against a condition, disease or its symptoms. In one aspect, the condition is conception. The term vaccine encompasses prophylactic as well as therapeutic vaccines. A combination vaccine is one which combines two or more vaccines, or two or more compounds or agents.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Embodiments

The present invention provides compositions and methods to diagnosis cancer based on the unexpected result that the ovary specific protein SAS1R is expressed in cancers, including uterine, lung, bladder, and ovarian cancers. That is, SAS1R is the first cancer-oocyte antigen discovered. Other tissues have had antigens that are generally highly developmentally regulated and restricted to expression in only one or a few tissues, but are dysregulated and expressed in cancer, such as the long known testis-cancer antigen. However, SAS1R is the first cancer-oocyte antigen/biomarker. Furthermore, SAS1R is expressed in high percentages of the various cancers tested. It was unexpected that SAS1R was expressed in these cancers and that such a high percentage of these types of cancer express SAS1R. SAS1R expression can be determined using techniques known in the art which will detect, for example, SAS1R protein or fragments of SAS1R, SAS1R mRNA, and SAS1R miRNA.

Because one cancer-oocyte antigen/biomarker has now been disclosed herein, the present invention encompasses cancer-oocyte antigen/biomarkers other than SAS1R as well. The invention encompasses using antibodies directed against the other cancer-oocyte antigens/biomarkers, targeting those antigens to kill cells or to detect the cancer cells, and using those antigens, or fragments or homologs thereof as immunogens to prevent cancer-oocyte antigen positive cancers from starting or progressing. Without wishing to be bound by any particular theory, it is contemplated that the biomarkers will be proteins and that the techniques described herein for SAS1R will be useful for targeting the new cancer-oocyte antigens as well.

The present invention provides compositions and methods useful for diagnosing, treating, and preventing cancer, based on the unexpected result disclosed herein that the ovarian protein, SAS1R, is expressed in multiple cancers, thus making SAS1R the first cancer-oocyte antigen.

In one aspect, the cancer is a carcinoma. In one aspect, the cancer is a sarcoma. In one aspect, the cancer is uterine cancer. In one aspect, the cancer is ovarian cancer. In one aspect, the cancer is lung cancer. In one aspect, the lung cancer is adenocarcinoma. In one aspect, the lung cancer is squamous carcinoma.

In one aspect, the cancer is a malignant mixed mullerian tumor (MMMT; also referred to as sarcomatoid carcinoma). In one aspect, the cancer is endometrioid carcinoma.

Cancer Diagnosis

Detection and diagnosis of SAS1R positive cancers can be performed by obtaining samples from a subject and determining whether the sample is positive for SAS1R and compositions and methods are also provided for in vivo imaging of SAS1R positive cells.

In one embodiment, tumors expressing SAS1R can be directly targeted for diagnosis. This can be done for example using antibodies or fragments thereof that are directed against SAS1R and which have been conjugated to an imaging agent useful for in vivo imaging.

In one embodiment, tissue samples and other samples obtained from a subject can be used to detect SAS1R. Tissue samples can include tumor biopsies and other tissues where SAS1R from cancer cells, including SAS1R shed from dead cancer cells. The samples other than tumor biopsies include, but are not limited to, tissue samples, blood, plasma, peritoneal fluids, ascites, follicular fluid, urine, feces, saliva, mucus, phlegm, sputum, tears, cerebrospinal fluid, effusions such as lung effusions, lavage, and Pap smears.

Antibodies and other peptides can be conjugated to a number of agents capable of being imaged in vivo and used for imaging/detection in ex vivo tests and assays such as immunofluorescence, ELISA, etc. In one embodiment, the antibody is detected using at least one of enzyme-linked immunoassay, western blot, lateral flow membrane test, latex agglutination, and other forms of immunochromatography or immunoassay utilizing at least one antibody. In one embodiment, SAS1R proteins are detected using ELISA.

Multiple techniques for measuring proteins and peptides are known in the art or described herein and can use in the practice of the invention. These include, but are not limited to, for example:

Electrochemiluminescent immunoassay;
Bioluminsescent Immunoassay (for example, with use of apoaequorin and oelenterazine);
Luminescent oxygen channeling immunoassay (LOCI);
The Erenna Immunoassay System (a modified microparticle-based sandwich immunoassay with single-molecule counting);
Nanoparticle Immunoassay: nano-particles, spheres, or tubes as solid phases
  upconverting phosphor nanoparticle using antiStokes shift
  quantum dot immunoassay (Heterogeneous immunoassay in which a nanometer-sized (less than 10 nm) semiconductor quantum dot is used as a label. A quantum dot is a highly fluorescent nanocrystal composed of CdSe, CdS, ZnSe, InP, or InAs or a layer of ZnS or CdS on, for example, a CdSe core);
Fluorescence Excitation Transfer Immunoassay;
ImmunoPCR Immunoassay;
Solid Phase, Light-Scattering Immunoassay: Indium spheres are coated on glass to measure an antibody binding to an antigen. Binding of antibodies to antigens increases dielectric layer thickness, which produces a greater degree of scatter than in areas where only an antigen is bound. Quantitation is achieved by densitometry; and
Surface Effect Immunoassay: with antibody immobilized on the surface of a waveguide (a quartz, glass, or plastic slide, or a gold- or silver-coated prism), and binding of antigen measured directly by total internal reflection fluorescence, surface plasmon resonance, or attenuated total reflection.

In one aspect, an antibody or a fragment or homolog thereof of the invention can be conjugated to an imaging agent. In one embodiment, antibody complex comprises an imaging agent selected from the group consisting of a radionuclide, a radiological contrast agent, a paramagnetic ion, a metal, a biological tag, a fluorescent label, a chemiluminescent label, an ultrasound contrast agent and a photoactive agent. In one aspect, the imaging agent is a radionuclide. In one aspect, the radionuclide is selected from the group consisting of $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52}$mMn, $^{55}$Co, $^{72}$As, $^{75}$Br, $^{76}$Br, $^{82}$mRb, $^{83}$Sr, and other gamma-, beta-, or positron-emitters. In one aspect, the radionuclide is $^{111}$In.

The invention further provides for use of the monoclonal antibodies described herein for drug delivery and for diagnostics. For example, various agents as described herein can be conjugated to the antibodies. Drugs such as calicheamicin, peptides such as D(KLAKLAK)$^2$, and radionuclides such as beta $^{90}$Y, gamma $^{131}$I, and positron $^{124}$I emitters can be conjugated to monoclonal antibodies to human SAS1R and used to image lung tumors, as radiotherapeutic and chemotherapeutic agents for treatment.

The invention further provides a method for detecting cancer, diagnosing cancer, monitoring the progression of cancer, or monitoring treatment of a cancer, wherein the cancer cells express or present SAS1R or a homolog or fragment thereof. The method comprises administering to a test subject a pharmaceutical composition comprising a peptide ligand complex wherein the complex comprises an imaging agent, and then detecting the imaging agent and determining the levels and location of the imaging agent in a test subject. The levels are determined using the systems, computers, and programs for that particular kind of imaging, whether it be MRI, PET, SPECT/CT, CAT scans, X-rays, ultrasound, etc. The values obtained from the final processing of the levels are then used for the comparison. A comparison of the levels and location in the test subject is made with the levels and location of the imaging agent from an otherwise identical location from an unaffected subject or with an unaffected area of the test subject. A higher level or different location of the imaging agent in the test subject compared with the level or location of the imaging agent in said sample from an unaffected subject or from an unaffected area of the test subject, is an indication that the test subject has a cancer expressing or presenting SAS1R or a homolog or fragment thereof. The levels or location of the detected imaging agent is an indicator of the location and amount of the biomarker SAS1R.

In one embodiment, the cancer is selected from the group consisting of lung cancer, MMMT, bladder cancer, ovarian cancer, uterine cancer, endometrial cancer, breast cancer, head and neck cancer, liver cancer, pancreatic cancer, esophageal cancer, stomach cancer, cervical cancer, prostate cancer, adrenal cancer, lymphoma, leukemia, salivary gland cancer, bone cancer, brain cancer, cerebellar cancer, colon cancer, rectal cancer, colorectal cancer, oronasopharyngeal cancer, NPC, kidney cancer, skin cancer, melanoma, basal cell carcinoma, hard palate carcinoma, squamous cell carcinoma of the tongue, meningioma, pleomorphic adenoma, astrocytoma, chondrosarcoma, cortical adenoma, hepatocellular carcinoma, pancreatic cancer, squamous cell carcinoma, and adenocarcinoma.

In one aspect, the cancer is a metastatic cancer.

The invention is also useful for comparing the levels of SAS1R being imaged to help determine whether a cancer is benign or malignant, based on the level of imaging agent detected (a measure of the amount of SAS1R).

The invention is also useful for determining the stage of carcinogenesis of a cancer and monitoring its progression from early to late stage cancer. This method is useful for determining the type and amount of therapy to use.

Optionally, a therapeutic agent can be attached or can be included in a pharmaceutical composition comprising the imaging complex.

Clinically relevant PET/SPECT tracers as used herein enable the detection of small tumors and metastases.

In one aspect, the imaging agent or detectable moiety includes, but is not limited to, a radionuclide, a radiological contrast agent, a paramagnetic ion, a metal, a biological tag, a fluorescent label, a chemiluminescent label, an ultrasound contrast agent and a photoactive agent.

The antibody, or a homolog or fragment thereof, imaging complexes of the invention encompass detecting, diagnosing, and localizing cancers other than the ones disclosed herein, as long as the cancer is a SAS1R positive cancer. The present invention further provides for quantifying levels of SAS1R, and thus encompasses the ability to distinguish normal, benign, and malignant tissue.

The invention includes detection of SAS1R microRNAs in blood samples as biomarkers. miRNAs are RNA molecules of 22 nucleotides or less in length. These molecules have been found to be highly involved in the pathology of several types of cancer. Although the miRNA molecules are generally found to be stable when associated with blood serum and its components after EDTA treatment, introduction of locked nucleic acids (LNAs) to the miRNAs via PCR further increases stability of the miRNAs. LNAs are a class of nucleic acid analogues in which the ribose ring is "locked" by a methylene bridge connecting the 2'-O atom and the 4'-C atom of the ribose ring, which increases the molecule's affinity for other molecules.

The present invention further provides kits comprising at least one antibody ligand complex of the invention, an instructional material, and optionally includes at least one imaging agent and optionally at least one therapeutic agent.

The present invention provides multiple techniques for measuring SAS1R mRNA and protein expression and levels, including but not limited to, PCR, northern blots, western blots, immunohistochemistry, and immunofluorescence.

Treating Cancer

The present invention provides compositions and methods for treating cancers expressing SAS1R. In one aspect, the expressed SAS1R is a protein. In one aspect, the present invention encompasses the use of an antibody capable of binding specifically to SAS1R on the surface of a cancer cell. In one aspect, the antibody can bind to one of the epitopes described herein. In one aspect, the antibody can binding to one of the sequences and fragments disclosed herein. Said antibody can be, for example, a single chain antibody, a monoclonal antibody, a bi-specific antibody, a chimeric antibody, a synthetic antibody, a polyclonal antibody, a humanized antibody, a human antibody, or active fragments or homologs thereof. In one aspect, a therapeutic agent is coupled to the antibody.

In one embodiment, the present invention provides antibodies useful for diagnosing and treating cancer, wherein said antibodies bind to SAS1R. In one embodiment, the present invention provides antibodies useful for diagnosing and treating cancer, wherein said antibodies bind to an epitope of SAS1R. In one aspect, the present invention provides pharmaceutical compositions comprising antibodies of the invention.

Many therapeutic agents are available that can be conjugated to an antibody directed against SAS1R and used in combination with the antibody. For example, molecules that can be attached to SAS1R include, but are not limited to, pro-drugs, drugs, toxins, protein toxins, liposomes, filled liposomes, radioactive isotopes, and enzymes. The use of antibody-enzyme conjugates directed at tumor-associated antigens to achieve site-specific activation of prodrugs to potent cytotoxic species, termed "antibody-directed enzyme prodrug therapy" (ADEPT). In one aspect, the antibody directed against SAS1R is useful for treating cancer by antibody-mediated complement-dependent cell death.

Because of the stage specific expression of SAS1R, if targeted for therapy in a cancer patient, the reserve of oocytes contained in primordial and primary follicles in the ovary would be preserved. That is because, not only is SAS1R specific for the oocyte, but it is expressed in oocyte in a precise temporal and spatial manner. For example, SAS1R expression is specific for particular stages of oocyte development during follicular maturation (data not shown). SAS1R proteins appear in ovaries only in those oocytes that have reached the secondary follicle stage of follicular maturation. SAS1R then persists only in the oocytes within subsequent stages of pre-antral and antral follicles. The first stage at which SAS1R appears, the secondary follicle, is defined as those oocytes that are surrounded by two or more layers of granulose cells. This finding indicates that using SAS1R as a drug target, vaccine, or surface target for gene or drug delivery would permit the selective attack on only the pool of maturing oocytes and not oocytes contained within primordial and primary follicles. In other words, this is the definitive demonstration that targeting SAS1R would spare the ovarian reserve of immature oocytes.

Because among adult tissues SAS1R is expressed only in oocytes and as disclosed herein in tumors, the methods of the present invention which would target SAS1R means that its use as a drug target or as a vaccine would allow for selective targeting of the cells and tissues that express SAS1R.

Additionally, it is known that SAS1R is an active enzyme, and is thus a drugable target for cancer therapy.

A cancer drug target, such as the one disclosed herein, fulfills essential criteria for targeted cancer therapy, as well as for sparing normal cells that do not express the target.

The present invention provides compositions and methods useful for inhibiting the interaction of SAS1R with other proteins. The present application further provides for the use of antibodies directed against SAS1R to detect and treat cancer. In one aspect, the type of antibody includes, but is not limited to, a polyclonal antibody, a monoclonal antibody, a chimeric antibody, and a synthetic antibody. In one aspect, the antibody is a monoclonal antibody. The invention further provides hybridomas comprising monoclonal antibodies of the invention. The invention further provides sequences and fragments of antibodies of the invention.

Inhibitors of SAS1R include those which inhibit its interaction or binding with a sperm protein such as SLLP1 or any other protein, its activity as a protease, or inhibit its regulation of downstream activities included in SAS1R signal transduction pathways, including its role in cancer cells. In one aspect, the inhibitor is SAS1R, or a fragment or homolog of SAS1R which binds with SLLP1. In one aspect, the SAS1R fragment is an N-terminus portion of the protein. In one aspect, the N-terminus comprises about the amino terminal 121 amino acid residues of mature SAS1R. In another aspect, the SAS1R fragment which binds with SLLP1 and inhibits SLLP1 interaction with an egg is a C-terminus portion of SAS1R. In one aspect, the C-terminus of the SAS1R comprises about the carboxy terminal 210 amino acid residues of SAS1R. One of ordinary skill in the art will appreciate that any kind of compound that inhibits SAS1R levels, function, or activity as described herein, or those that are yet unknown, are encompassed by the present invention.

An inhibitor of SAS1R can be any type of molecule that inhibits, for examples, SAS1R function, activity, expression, and protein levels.

In one embodiment, the present invention provides compositions and methods useful for determining that SAS1R functions as an active metalloprotease, as well as for measuring that function. These methods are useful for determining whether a test compound or molecule can inhibit SAS1R and whether they are useful for treating cancer. The present application includes compounds identified by these methods.

In one aspect, SAS1R is inhibited in an N-terminus portion of the protein. In one aspect, the N-terminus comprises about the amino terminal 121 amino acid residues of mature SAS1R. In another aspect, the SAS1R is inhibited in a C-terminus portion of the protein. In one aspect, the C-terminus of the protein comprises about the carboxy terminal 210 amino acid residues of SAS1R. In one aspect, the inhibitor is an antibody directed against SAS1R. In another aspect, the inhibitor is a drug or other compound. In one aspect, the inhibitor inhibits the protease activity of SAS1R. In another aspect, the inhibitor inhibits the interaction of SAS1R with SLLP1 or any other protein. In one aspect, the interaction is binding.

The present inventors have surprisingly found that suitable antigens for immunotherapeutic strategies include the protein SAS1R. The present application discloses immunogenic compositions comprising an immunogen that is derived from eggs in normal cells, which as disclosed herein is also expressed in, for example, lung, uterine and ovarian cancers. That antigen is the SAS1R protein, as well as antigenic fragments and homologs thereof. The present application demonstrates that cells expressing SAS1R can be killed using such strategies.

The present invention provides compositions and methods useful for detecting and diagnosing uterine and ovarian cancer and for treating these diseases.

In one aspect, SAS1R, or fragments or homologs thereof which maintain the immunogenic activity of full length SAS1R, can be administered to a subject to elicit an immune response against SAS1R. In one aspect, the administration of SAS1R and fragments and homologs thereof which elicit an immune response is useful as a vaccine. In one aspect, it is a vaccine against cancer. In one aspect, the cancer is lung, uterine cancer or ovarian cancer. In one aspect, the cancer is a malignant mixed mullerian tumor. In one aspect, the ovarian cancer is a serous ovarian cancer.

SAS1R isoforms are found on the cell surface in oocytes and in transfected cells, as well as on cancer cells as described herein. Therefore, in cancer cells expressing SAS1R on the surface, SAS1R is a tumor selective surface target. In one aspect, cancer cells can be targeted with an antibody directed against SAS1R. In one aspect, the antibody is a humanized antibody. In one aspect, the antibody has a toxin or drug linked to it for delivery to a cancer cell.

The present invention further provides novel primers useful for identifying and diagnosing SAS1R expression.

In one embodiment, the compositions and methods of the invention are useful in mammals. In one aspect, the mammal is a human.

The SAS1R enzyme shows stage specific expression in secondary and subsequent follicular oocytes, including preantral and antral follicles (data not shown), rendering it a suitable target for cancer therapy or as a vaccine that will spare naked, primordial, and primary oocytes, and preserve the ovarian reserve of germ cells. Therefore, the invention further encompasses the compositions and methods for identifying compounds that inhibit SAS1R.

The present invention further provides methods for treating cancer. In one aspect, the invention provides compositions and methods for treating cancer cells expressing SAS1R. In one aspect, SAS1R is a cell surface protein. The methods for treating cancer cells expressing SAS1R include those described herein and other known methods which can target SAS1R and its activity.

The linkage of a diagnostic biomarker to a specific therapy will result in the "intelligent" treatment of cancer by identifying subjects whose disease will respond to a specific treatment. This is often referred to as "individualized therapy" or "personalized medicine". For example, an ovarian or uterine cancer biomarker would greatly reduce the costs associated with drug development by enabling the selection of a more homogeneous patient population for smaller, more cost-effective clinical trials. A useful biomarker can also accelerate drug development by facilitating decisions regarding which agents to pursue in the early stages of clinical development. By emphasizing targets that can be both a successful diagnostic or screening test and a therapeutic drug or vaccine target, particular advances may be possible.

The present invention provides a means to phenotype a subject's tumor to identify the SAS1R signature. This subject will likely benefit from a SAS1R targeted therapy. Such therapy can be a first or "front line" therapy, used before more traditional chemotherapeutic agents which induce weakness, hair loss, diarrhea and anemia, due to their non selective mechanisms of action.

The present invention further provides for altering the actin distribution in a cancer cell and altering the appearance of the cells, comprising contacting said cell with an antibody directed against SAS1R, wherein said antibody binds with SAS1R and the actin distribution of the cell is altered and the appearance of the cell is altered.

The present invention further provides compositions and methods utilizing SAS1R, and fragments and homologs thereof, to elicit an immune response against SAS1R. In one aspect, administration of SAS1R or antigenic fragments or homologs thereof results in inhibiting SAS1R. In one aspect, such an immunogenic response and resulting inhibition of SAS1R function.

Endometrial cancer nomenclature includes Type 1 and Type 2 cancers. Type 1 is endometrioid, it is the most common, is hormonally driven, and most are detected at low stage and there is a slow progression. Type 2 (UPSC, MMT, Clear cell) is aggressive and there is low survival. There are about 40,000 new cases of uterine cancer each year in the U.S., of which about 7,500 die. There are no screening assay for early detection and monitoring of uterine cancer. Data disclosed herein that SAS1R is unexpectedly a uterine cancer marker in a form of uterine cancer known as MMMT (Malignant mixed mullerian tumor). Of Type 2 endometrial carcinomas, the MMMT (also referred to as Sarcomatoid carcinoma) has a complex biology and comprises an epithelial (glands) component with mesenchymal differentiation. UPSC has PTEN mutations, is epithelial, and is transplantable.

MMMTs typically present as a polypoid mass protruding through the cervical os. It is a carcinoma with carcinoma and sarcoma histologic features (sarcomatoid carcinoma). This type of cancer occurs predominantly in post-menopausal women. MMMTs account for approximately 10% of endometrial malignancies.

Many studies have demonstrated that at the time of diagnosis, a cancer patient already has circulating cancer cells within his or her blood stream. It is not uncommon for 5 or 10 cancer cells to be found in each milliliter of blood. This means that it is not uncommon for thousands of cancer cells to be present in virtually every organ, as potential metastases, at the time of diagnosis. The survival of even a tiny fraction of these cells will result in the development of a metastasis, and reduce the survival of the patient.

The following are useful mammalian SAS1R sequences:

```
mouse SAS1R Variant 1, 435 residues-
                                                (SEQ ID NO: 19)
MGIMGSLWPWILTMLSLLGLSMGAPSASRCSGVCSTSVPEGFTPEGSPVFQD

KDIPAINQGLISEETPESSFLVEGDIIRPSPFRLLSVTNNKWPKGVGGFVEIPFL

LSRKYDELSRRVIMDAFAEFERFTCIRFVAYHGQRDFVSILPMAGCFSGVGR

SGGMQVVSLAPTCLRKGRGIVLHELMHVLGFWHEHSRADRDRYIQVNWNE

ILPGFEINFIKSRSTNMLVPYDYSSVMHYGRFAFSWRGQPTIIPLWTSSVHIGQ

RWNLSTSDITRVCRLYNCSRSVPDSHGRGFEAQSDGSSLTPASISRLQRLLEA

LSEESGSSAPSGSRTGGQSIAGLGNSQQGWEHPPQSTFSVGALARPPQMLAD

ASKSGPGAGADSLSLEQFQLAQAPTVPLALFPEARDKPAPIQDAFERLAPLP

GGCAPGSHIREVPRD mouse SAS1R Variant 2 (formerly called ZEP-N), 414
a.a. residues-
                                                 (SEQ ID NO: 6)
MGAPSASRCSGVCSTSVPEGFTPEGSPVFQDKDIPAINQGLISEETPESSFLVE

GDIIRPSPFRLLSVTNNKWPKGVGGFVEIPFLLSRKYDELSRRVIMDAFAEFE

RFTCIRFVAYHGQRDFVSILPMAGCFSGVGRSGGMQVVSLAPTCLRKGRGIV

LHELMHVLGFWHEHSRADRDRYIQVNWNEILPGFEINFIKSRSTNMLVPYD

YSSVMHYGRFAFSWRGQPTIIPLWTSSVHIGQRWNLSTSDITRVCRLYNCSR

SVPDSHGRGFEAQSDGSSLTPASISRLQRLLEALSEESGSSAPSGSRTGGQSIA

GLGNSQQGWEHPPQSTFSVGALARPPQMLADASKSGPGAGADSLSLEQFQL

AQAPTVPLALFPEARDKPAPIQDAFERLAPLPGGCAPGSHIREVPRD mouse SAS1R Variant 3 (formerly called ZEP-Variant 2),
380 a.a. residues-
                                                (SEQ ID NO: 10)
MGAPSASRCSGVCSTSVPEGFTPEGSPVFQDKDIPAINQGLISEETPESSFLLS

RKYDELSRRVIMDAFAEFERFTCIRFVAYHGQRDFVSILPMAGCFSGVGRSG

GMQVVSLAPTCLRKGRGIVLHELMHVLGFWHEHSRADRDRYIQVNWNEIL

PGFEINFIKSRSTNMLVPYDYSSVMHYGRFAFSWRGQPTIIPLWTSSVHIGQR

WNLSTSDITRVCRLYNCSRSVPDSHGRGFEAQSDGSSLTPASISRLQRLLEAL
```

-continued

SEESGSSAPSGSRTGGQSIAGLGNSQQGWEHPPQSTFSVGALARPPQMLADA

SKSGPGAGADSLSLEQFQLAQAPTVPLALFPEARDKPAPIQDAFERLAPLPG

GCAPGSHIREVPRD mouse SAS1R Variant 4, 401 a.a. residues-
(SEQ ID NO: 20)
MGIMGSLWPWILTMLSLLGLSMGAPSASRCSGVCSTSVPEGFTPEGSPVFQD

KDIPAINQGLISEETPESSFLLSRKYDELSRRVIMDAFAEFERFTCIRFVAYHG

QRDFVSILPMAGCFSGVGRSGGMQVVSLAPTCLRKGRGIVLHELMHVLGF

WHEHSRADRDRYIQVNWNEILPGFEINFIKSRSTNMLVPYDYSSVMHYGRF

AFSWRGQPTIIPLWTSSVHIGQRWNLSTSDITRVCRLYNCSRSVPDSHGRGFE

AQSDGSSLTPASISRLQRLLEALSEESGSSAPSGSRTGGQSIAGLGNSQQGWE

HPPQSTFSVGALARPPQMLADASKSGPGAGADSLSLEQFQLAQAPTVPLALF

PEARDKPAPIQDAFERLAPLPGGCAPGSHIREVPRD mouse SAS1R Variant 5 (formerly called ZEP Variant 1),
392 a.a. residues-
(SEQ ID NO: 8)
MGAPSASRCSGVCSTSVPEGFTPEGSPVFQDKDIPAINQGLISEETPESSFLVE

GDIIRPGVSHGVSFPDELSRRVIMDAFAEFERFTCIRFVAYHGQRDFVSILPM

AGCFSGVGRSGGMQVVSLAPTCLRKGRGIVLHELMHVLGFWHEHSRADRD

RYIQVNWNEILPGFEINFIKSRSTNMLVPYDYSSVMHYGRFAFSWRGQPTIIP

LWTSSVHIGQRWNLSTSDITRVCRLYNCSRSVPDSHGRGFEAQSDGSSLTPA

SISRLQRLLEALSEESGSSAPSGSRTGGQSIAGLGNSQQGWEHPPQSTFSVGA

LARPPQMLADASKSGPGAGADSLSLEQFQLAQAPTVPLALFPEARDKPAPIQ

DAFERLAPLPGGCAPGSHIREVPRD mouse SAS1R Variant 6, 413 a.a. residues-
(SEQ ID NO: 21)
MGIMGSLWPWILTMLSLLGLSMGAPSASRCSGVCSTSVPEGFTPEGSPVFQD

KDIPAINQGLISEETPESSFLVEGDIIRPGVSHGVSFPNELSRRVIMDAFAEFER

FTCIRFVAYHGQRDFVSILPMAGCFSGVGRSGGMQVVSLAPTCLRKGRGIVL

HELMHVLGFWHEHSRADRDRYIQVNWNEILPGFEINFIKSRSTNMLVPYDY

SSVMHYGRFAFSWRGQPTIIPLWTSSVHIGQRWNLSTSDITRVCRLYNCSRS

VPDSHGRGFEAQSDGSSLTPASISRLQRLLEALSEESGSSAPSGSRTGGQSIAG

LGNSQQGWEHPPQSTFSVGALARPPQMLADASKSGPGAGADSLSLEQFQLA

QAPTVPLALFPEARDKPAPIQDAFERLAPLPGGCAPGSHIREVPRD

Human SAS1R nucleic acid sequence- GenBank accession no.
NM_001002036, 1296 bp mRNA-
(SEQ ID NO: 22)
atggagggtgtaggggtctctggccttgggtgctggtctgctctccttgccaggtgtg atcctaggagcgcccctggcctccagctgcgcaggagcctgtggtaccagcttcccagat ggcctcacccctgagggaacccaggcctccggggacaaggacattcctgcaattaaccaa gggctcatcctggaagaaaccccagagagcagcttcctcatcgagggggacatcatccgg ccgagtcccttccgactgctgtcagcaaccagcaacaaatgcccatgggtggtagtggt gtcgtggaggtccccttcctgctctccagcaagtacgatgagcccagccgccaggtcatc ctggaggctcttgcggagtttgaacgttccacgtgcatcaggtttgtcacctatcaggac cagagagacttcatttccatcatccccatgtatgggtgcttctcgagtgtggggcgcagt ggagggatgcaggtggtctccctggcgcccacgtgtctccagaagggccggggcattgtc

```
cttcatgagctcatgcatgtgctgggcttctggcacgagcacacgcgggccgaccgggac cgctatatccgtgtcaactggaacgagatcctgccaggctttgaaatcaacttcatcaag tctcagagcagcaacatgctgacgccctatgactactcctctgtgatgcactatgggagg ctcgccttcagccggcgtgggctgccaccatcacaccactttgggccccagtgtccac atcggccagcgatggaacctgagtgcctcggacatcacccgggtcctcaaactctacggc tgcagcccaagtggccccaggccccgtgggagagggtcccatgcccacagcactggtagg agccccgctccggcctccctatctctgcagcggcttttggaggcactgtcggcggaatcc aggagccccgacccagtggttccagtgcgggaggccagcccgttcctgcagggcctggg gagagcccacatgggtgggagtccctgcctgaaaagctcagtgcagaggcctcggca aggcagcctcagaccctagcttcctcccaagatcaaggcctggagcaggtgcccccggt gttgctcaggagcagtcctggctggccggagtgtccaccaagcccacagtcccatcttca gaagcaggaatccagccagtccctgtccagggaagcccagctctgccaggggctgtgta cctagaaatcatttcaaggggatgtccgaagattaa Human SAS1R protein-431 amino acids, GenBank accession no.
NP_001002036.3-
                                                  (SEQ ID NO: 23)
MEGVGGLWPWVLGLLSLPGVILGAPLASSCAGACGTSFPDGLTPEGTQASG

DKDIPAINQGLILEETPESSFLIEGDIIRPSPFRLLSATSNKWPMGGSGVVEVPF

LLSSKYDEPSRQVILEALAEFERSTCIRFVTYQDQRDFISIIPMYGCFSSVGRS

GGMQVVSLAPTCLQKGRGIVLHELMHVLGFWHEHTRADRDRYIRVNWNEI

LPGFEINFIKSQSSNMLTPYDYSSVMHYGRLAFSRRGLPTITPLWAPSVHIGQ

RWNLSASDITRVLKLYGCSPSGPRPRGRGSHAHSTGRSPAPASLSLQRLLEA

LSAESRSPDPSGSSAGGQPVPAGPGESPHGWESPALKKLSAEASARQPQTLA

SSPRSRPGAGAPGVAQEQSWLAGVSTKPTVPSSEAGIQPVPVQGSPALPGGC

VPRNHFKGMSED
```

The present invention encompasses techniques demonstrated herein to detect SAS1R, and one of ordinary skill in the art will appreciate that other techniques can be used as well. Detecting and measuring protein can be done in many ways. For Example, useful methods include, for example, performing LC-MS/MS analyses, which can be performed on a ThermoFinnigan LCQ Deca ion trap MS instrument equipped with a ThermoFinnigan Surveyor HPLC pump and microelectrospray source and operated with ThermoFinnigan Xcalibur version 1.2 system control and data analysis software. Analysis of samples can be performed with an acetonitrile gradient and a Monitor C18 (Column Engineering) packed tip with 100 µm ID, 360 µm OD, and 5-15 µm tip opening. The flow from the HPLC pump can be split to achieve 500 mL to 1 µl flow rate from the packed tip. Two gradients can be used, "fast" and "normal", depending on the complexity of the sample being analyzed.

A protein can be subjected to Tandem Mass Spectroscopic Analysis and peptide sequences obtained.

In one embodiment, the invention provides a pharmaceutical composition comprising a pharmaceutically-acceptable carrier and SAS1R, or a homolog, fragment or derivative thereof, wherein said protein is capable of inducing an immune response in a subject. In one aspect, the method is useful as a vaccine or as a treatment. In one aspect, the invention provides a pharmaceutical composition, wherein said egg protein or peptide comprises an amino acid sequence selected from the group consisting of SEQ ID NOs:6, 8, 10, 19, 20, 21, and 23, and fragments and homologs thereof.

In one embodiment, at least one isolated nucleic acid comprising a nucleic acid sequence encoding an egg protein is administered. In one aspect, the egg protein comprises a sequence selected from the group consisting of SEQ ID NOs: 6, 8, 10, 19, 20, 21, and 23, and fragments and homologs thereof.

An administered protein or a protein expressed by an administered isolated nucleic acid comprising a sequence encoding the protein can act to inhibit SLLP1 and SAS1R interaction or binding.

The present invention also provides for administering at least one SLLP1 protein or biologically active homologs and fragments thereof capable of binding with or interacting with SAS1R to detect SAS1R. In one aspect, the SLLP1 protein is labeled.

It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

Antibodies and their Preparation

Antibodies directed against proteins, polypeptides, or peptide fragments thereof of the invention may be generated using methods that are well known in the art. For instance, U.S. patent application Ser. No. 07/481,491, which is incorporated by reference herein in its entirety, discloses methods of raising antibodies to peptides. For the production of antibodies, various host animals, including but not limited to rabbits, mice, and rats, can be immunized by injection with a polypeptide or peptide fragment thereof. To increase the immunological response, various adjuvants may be used depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

In one embodiment, antibodies, or antisera, directed against SAS1R or a homolog or fragment thereof, are useful for blocking the activity of SAS1R, including its ability to interact with other molecules or cells.

Fragments of SAS1R may be generated and antibodies prepared against the fragments. Assays are provided herein to determine whether an antibody directed against SAS1R, or a fragment thereof, have the ability to detect SAS1R, to inhibit SAS1R activity, or regulate SAS1R function.

The assays include measuring the ability of SAS1R to bind with or interact with SLLP proteins, as well as the ability of an antibody to block SAS1R's role in fertilization. For example, in vitro fertilization assays are described herein using an antibody directed SAS1R and this type of assay can be used to test the ability of new antibodies to block SAS1R's function. These same assays can be used to test any compound or agent's ability to disrupt SAS1R's interaction with a SLLP protein or to inhibit fertilization. Protease assays for measuring SAS1R protease activity are also available when needed to confirm that a fragment or homolog of SAS1R maintains the same activity as the parent SAS1R molecule.

Various methods of preparing fragments of SAS1R and making antibodies against SAS1R are available and these methods can be used to map the various regions of SAS1R that are susceptible to inhibition by an antibody.

For example, fragments of SAS1R can be prepared for use as an antigen, such as wherein the antibody binds to one of more fragments comprising amino acids 1-25, 26-50, 51-75, 76-100, 101-125, 126-150, 151-175, 176-200, 201-225, 226-250, 251-275, 276-300, 301-325, 326-350, 351-375, 376-400, and 401-414 of SAS1R Variant 2 (SEQ ID NO:6) or wherein the antibody binds to one or more fragments comprising amino acids 1-25, 26-50, 51-75, 76-100, 101-125, 126-150, 151-175, 176-200, 201-225, 226-250, 251-275, 276-300, 301-325, 326-350, 351-375, 376-400, 401-425, and 426-435 of SAS1R Variant 1 (SEQ ID NO:19) or wherein the antibody binds to amino acids 1-25, 26-50, 51-75, 76-100, 101-125, 126-150, 151-175, 176-200, 201-225, 226-250, 251-275, 276-300, 301-325, 326-350, 351-375, 376-400, 401-425, and 426-431 of SAS1R Variant 1 (SEQ ID NO:23). The invention further encompasses fragments comprising 20 amino acids, such as amino acid residues 1-20, 21-40, 41-60, etc. Such techniques can also be applied to the full-length protein.

Of course, these fragments can also be prepared to yield overlapping sequences and longer and shorter fragments can be prepared. For example, as described herein, interaction experiments between SLLP1 and SAS1R indicate there are at least two binding regions between the two proteins when they interact, which may have different functions. There, fragments encompassing sections of the more N-terminal region of SAS1R or the more C-terminal region of SAS1R can be prepared, such as wherein the antibody binds to amino acids about 1 to about 121 (N-terminal) or an antibody which binds to about 204 to about 414 (more C-terminal) of SAS1R (SEQ ID NO:6) or an antibody which binds to similar regions of SEQ ID NO:23 (human SAS1R).

The antigenic fragments of the proteins of the invention may include peptide antigens that are at least about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150 or up to about 200 amino acids in length. Also included are full-length unprocessed protein as well as mature processed protein. These various length antigenic fragments may be designed in tandem order of linear amino acid sequence of the immunogen of choice, such as SAS1R, or staggered in linear sequence of the protein. In addition, antibodies to three-dimensional epitopes, i.e., non-linear epitopes, can also be prepared, based on, e.g., crystallographic data of proteins. Hosts may also be injected with peptides of different lengths encompassing a desired target sequence. Antibodies obtained from that injection may be screened against the short antigens of SAS1R and against mature SAS1R. Antibodies prepared against a SAS1R peptide may be tested for activity against that peptide as well as the full length SAS1R protein. Antibodies may have affinities of at least about $10^{-6}$M, $10^{-7}$M, $10^{-8}$M, $10^{-9}$M, $10^{-10}$M, $10^{-11}$M, or $10^{-12}$M toward the SAS1R peptide and/or the full-length SAS1R protein.

In one embodiment, the invention provides a therapeutic cancer vaccine comprising a pharmaceutical composition of the invention, said composition comprising one or more proteins, or variants, homologs, or fragments thereof, comprising an amino acid sequence selected from the group consisting of SEQ ID NOs: 6, 8, 10, 19, 20, 21, and 23, and fragments and homologs thereof, and optionally at least one other egg protein, or a variant, fragment, or homolog thereof.

Because of the temporally regulated expression of SAS1R in normal cells, any cells that might be killed would not include the early stage germ cells.

For the preparation of monoclonal antibodies, any technique which provides for the production of antibody molecules by continuous cell lines in culture may be utilized. For example, the hybridoma technique originally developed by Kohler and Milstein (1975, *Nature* 256:495-497), the trioma technique, the human B-cell hybridoma technique (Kozbor et al., 1983, *Immunology Today* 4:72), and the EBV-hybridoma technique (Cole et al., 1985, in *Monoclonal Antibodies and Cancer Therapy*, Alan R. Liss, Inc., pp. 77-96) may be employed to produce human monoclonal antibodies. In another embodiment, monoclonal antibodies are produced in germ-free animals.

In one embodiment, the monoclonal antibodies described herein and the hybridomas making the antibodies, as well as those not described herein, will be deposited with the American Type Culture Collection (10801 University Boulevard, Manassas, Va. 20110-2209) and assigned Accession Numbers. The deposits will be maintained under the terms of the Budapest Treaty on the International Recognition of the Deposit of Microorganisms for the Purposes of Patent Procedure and made available for use under those terms. This assures maintenance of a viable culture of the deposit for 30 years from the date of deposit. The deposits will be made available by ATCC under the terms of the Budapest Treaty, and subject to an agreement between the University of Virginia and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC section 122 and the Commissioner's rules pursuant thereto (including 37 CFR section 1.14 with particular reference to 886 OG 638). The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws. Nucleic acid and amino acid sequences will be deposited with GenBank and made accessible to the public.

In accordance with the invention, human antibodies may be used and obtained by utilizing human hybridomas (Cote et al., 1983, *Proc. Natl. Acad. Sci. U.S.A.* 80:2026-2030) or by transforming human B cells with EBV virus in vitro (Cole et al., 1985, in *Monoclonal Antibodies and Cancer Therapy*, Alan R. Liss, Inc., pp. 77-96). Furthermore, techniques developed for the production of "chimeric antibodies" (Morrison et al., 1984, *Proc. Natl. Acad. Sci. U.S.A.* 81:6851-6855; Neuberger et al., 1984, *Nature* 312:604-608; Takeda et al., 1985, *Nature* 314:452-454) by splicing the genes from a mouse antibody molecule specific for epitopes of SLLP polypeptides together with genes from a human antibody molecule of appropriate biological activity can be employed; such antibodies are within the scope of the present invention. Once specific monoclonal antibodies have been developed, the preparation of mutants and variants thereof by conventional techniques is also available.

In one embodiment, techniques described for the production of single-chain antibodies (U.S. Pat. No. 4,946,778, incorporated by reference herein in its entirety) are adapted to produce protein-specific single-chain antibodies. In another embodiment, the techniques described for the construction of Fab expression libraries (Huse et al., 1989, *Science* 246:1275-1281) are utilized to allow rapid and easy identification of monoclonal Fab fragments possessing the desired specificity for specific antigens, proteins, derivatives, or analogs of the invention.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment; the Fab fragments which can be generated by treating the antibody molecule with papain and a reducing agent; and Fv fragments.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

A nucleic acid encoding the monoclonal antibody obtained using the procedures described herein may be cloned and sequenced using technology which is available in the art, and is described, for example, in Wright et al. (1992, Critical Rev. in Immunol. 12(3,4):125-168) and the references cited therein. Further, the antibody of the invention may be "humanized" using the technology described in Wright et al., (supra) and in the references cited therein, and in Gu et al. (1997, Thrombosis and Hematocyst 77(4):755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art.

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222: 581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

In the production of antibodies, screening for the desired antibody can be accomplished by techniques known in the art, e.g., ELISA (enzyme-linked immunosorbent assay). Antibodies generated in accordance with the present invention may include, but are not limited to, polyclonal, monoclonal, chimeric (i.e., "humanized"), and single chain (recombinant) antibodies, Fab fragments, and fragments produced by a Fab expression library.

The peptides of the present invention may be readily prepared by standard, well-established techniques, such as solid-phase peptide synthesis (SPPS) as described by Stewart et al. in *Solid Phase Peptide Synthesis,* 2nd Edition, 1984, Pierce Chemical Company, Rockford, Ill.; and as described by Bodanszky and Bodanszky in *The Practice of Peptide Synthesis,* 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions that will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenyl esters.

Examples of solid phase peptide synthesis methods include the BOC method that utilized tert-butyloxcarbonyl as the α-amino protecting group, and the FMOC method which utilizes 9-fluorenylmethyloxcarbonyl to protect the α-amino of the amino acid residues, both methods of which are well-known by those of skill in the art.

To ensure that the proteins or peptides obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide can be purified to remove contaminants. In this regard, it will be appreciated that the peptide will be purified to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure peptide obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

Aptamers

The present invention is also directed to useful aptamers for blocking SAS1R function and activity, and its expression levels. In one embodiment, an aptamer is a compound that is selected in vitro to bind preferentially to another compound (in this case the identified proteins). In one aspect, aptamers are nucleic acids or peptides, because random sequences can be readily generated from nucleotides or amino acids (both naturally occurring or synthetically made) in large numbers but of course they need not be limited to these. In another aspect, the nucleic acid aptamers are short strands of DNA that bind protein targets. In one aspect, the aptamers are oligonucleotide aptamers. Oligonucleotide aptamers are oligonucleotides which can bind to a specific protein sequence of interest. A general method of identifying aptamers is to start with partially degenerate oligonucleotides, and then simultaneously screen the many thousands of oligonucleotides for the ability to bind to a desired protein. The bound oligonucleotide can be eluted from the protein and sequenced to identify the specific recognition sequence. Transfer of large amounts of a chemically stabilized aptamer into cells can result in specific binding to a polypeptide of interest, thereby blocking its function. [For example, see the following publications describing in vitro selection of aptamers: Klug et al., Mol. Biol. Reports 20:97-107 (1994); Wallis et al., Chem. Biol. 2:543-552 (1995); Ellington, Curr. Biol. 4:427-429 (1994); Lato et al., Chem. Biol. 2:291-303 (1995); Conrad et al., Mol. Div. 1:69-78 (1995); and Uphoff et al., Curr. Opin. Struct. Biol. 6:281-287 (1996)].

The present invention further encompasses the use of phylomers which inhibit or prevent SAS1R function or levels.

Aptamers offer advantages over other oligonucleotide-based approaches that artificially interfere with target gene function due to their ability to bind protein products of these genes with high affinity and specificity. However, RNA aptamers can be limited in their ability to target intracellular proteins since even nuclease-resistant aptamers do not efficiently enter the intracellular compartments. Moreover, attempts at expressing RNA aptamers within mammalian cells through vector-based approaches have been hampered by the presence of additional flanking sequences in expressed RNA aptamers, which may alter their functional conformation.

The idea of using single-stranded nucleic acids (DNA and RNA aptamers) to target protein molecules is based on the ability of short sequences (20 mers to 80 mers) to fold into unique 3D conformations that enable them to bind targeted proteins with high affinity and specificity. RNA aptamers have been expressed successfully inside eukaryotic cells, such as yeast and multicellular organisms, and have been shown to have inhibitory effects on their targeted proteins in the cellular environment.

Methods of Identifying Antagonists and Inhibitors of SAS1R

As used herein, an antagonist or inhibiting agent may comprise, without limitation, a drug, a small molecule, an antibody, an antigen binding portion thereof or a biosynthetic antibody binding site that binds a particular target protein; an antisense molecule that hybridizes in vivo to a nucleic acid encoding a target protein or a regulatory element associated therewith, or a ribozyme, aptamer, or small molecule that binds to and/or inhibits a target protein, or that binds to and/or inhibits, reduces or otherwise modulates expression of nucleic acid encoding a target protein.

This invention encompasses methods of screening compounds to identify those compounds that act as agonists (stimulate) or antagonists (inhibit) of the protein interactions and pathways described herein. Screening assays for antagonist compound candidates are designed to identify compounds that bind or complex with the peptides described herein, or otherwise interfere with the interaction of the peptides with other cellular proteins. Such screening assays will include assays amenable to high-throughput screening of chemical libraries, making them particularly suitable for identifying small molecule drug candidates.

SAS1R assays also include those described in detail herein, such as far-western, co-immunoprecipitation, immunoassays, immunocytochemical/immunolocalization, interaction with SLLP protein, fertilization, contraceptions, and immunogenicity.

The assays can be performed in a variety of formats, including protein-protein binding assays, biochemical screening assays, high-throughput assays, immunoassays, and cell-based assays, which are well characterized in the art.

All assays for antagonists are common in that they call for contacting the compound or drug candidate with a peptide identified herein under conditions and for a time sufficient to allow these two components to interact.

In binding assays, the interaction is binding and the complex formed can be isolated or detected in the reaction mixture. In a particular embodiment, one of the peptides of the complexes described herein, or the test compound or drug candidate is immobilized on a solid phase, e.g., on a microtiter plate, by covalent or non-covalent attachments. Non-covalent attachment generally is accomplished by coating the solid surface with a solution of the peptide and drying. Alternatively, an immobilized antibody, e.g., a monoclonal antibody, specific for the peptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with, but does not bind to a particular peptide identified herein, its interaction with that peptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, Nature (London), 340:245-246 (1989); Chien et al., Proc. Natl. Acad. Sci. USA, 88:9578-9582 (1991)) as disclosed by Chevray and Nathans, Proc. Natl. Acad. Sci. USA, 89: 5789-5793 (1991). Complete kits for identifying protein-protein interactions between two specific proteins using the two-hybrid technique are available. This system can also be extended to map protein domains involved in specific protein interactions as well as to pinpoint amino acid residues that are crucial for these interactions.

Compounds that interfere with the interaction of a peptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the peptide may be added to a cell along with the compound to be screened for a particular activity and the ability of the compound to inhibit the activity of interest in the presence of the peptide indicates that the compound is an antagonist to the peptide. The peptide can be labeled, such as by radioactivity.

Other assays and libraries are encompassed within the invention, such as the use of Phylomers® and reverse yeast two-hybrid assays (see Watt, 2006, Nature Biotechnology, 24:177; Watt, U.S. Pat. No. 6,994,982; Watt, U.S. Pat. Pub. No. 2005/0287580; Watt, U.S. Pat. No. 6,510,495; Barr et al., 2004, J. Biol. Chem., 279:41:43178-43189; the contents of each of these publications is hereby incorporated by reference herein in their entirety). Phylomers® are derived from sub domains of natural proteins, which makes them potentially more stable than conventional short random peptides. Phylomers® are sourced from biological genomes that are not human in origin. This feature significantly enhances the potency associated with Phylomers® against human protein targets. Phylogica's current Phylomer® library has a complexity of 50 million clones, which is comparable with the numerical complexity of random peptide or antibody Fab fragment libraries. An Interacting Peptide Library, consisting of 63 million peptides fused to the B42 activation domain, can be used to isolate peptides capable of binding to a target protein in a forward yeast two hybrid screen. The second is a Blocking Peptide Library made up of over 2 million peptides that can be used to screen for peptides capable of disrupting a specific protein interaction using the reverse two-hybrid system.

The Phylomer® library consists of protein fragments, which have been sourced from a diverse range of bacterial genomes. The libraries are highly enriched for stable subdomains (15-50 amino acids long). This technology can be integrated with high throughput screening techniques such as phage display and reverse yeast two-hybrid traps.

The present application discloses compositions and methods for inhibiting the proteins described herein, and those not disclosed which are known in the art are encompassed within the invention. For example, various modulators/effectors are known, e.g. antibodies, biologically active nucleic acids, such as antisense molecules, RNAi molecules, or ribozymes, aptamers, peptides or low-molecular weight organic compounds recognizing said polynucleotides or polypeptides.

The present invention also encompasses pharmaceutical and therapeutic compositions comprising the compounds of the present invention.

The present invention is also directed to pharmaceutical compositions comprising the compounds of the present invention. More particularly, such compounds can be formulated as pharmaceutical compositions using standard pharmaceutically acceptable carriers, fillers, solublizing agents and stabilizers known to those skilled in the art.

Vaccines and Immunogens

In one embodiment, the invention relates to methods and reagents for immunizing and treating a subject with an antigenic compound of the invention such as SAS1R and fragments and homologs thereof, to elicit specific cellular and humoral immune-responses against such specific antigens. The invention provides methods of using specifically prepared immunogen in fresh or lyophilized liposome, proper routes of administration of the immunogen, proper doses of the immunogen, and specific combinations of heterologous immunization including DNA priming in one administration route followed by liposome-mediated protein antigen boost in a different route to tailor the immune responses in respects of enhancing cell mediated immune response, cytokine secretion, humoral immune response, especially skewing T helper responses to be Th1 or a balanced Th1 and Th2 type. For more detail, see Klinefelter (U.S. patent application Ser. No. 11/572,453, which claims priority to international patent application PCT/US2005/026102).

A homolog herein is understood to comprise an immunogenic polypeptide having at least 70%, preferably at least 80%, more preferably at least 90%, still more preferably at least 95%, still more preferably at least 98% and most preferably at least 99% amino acid sequence identity with the naturally occurring SAS1R polypeptides mentioned above and is still capable of eliciting at least the immune response obtainable thereby. A homolog or analog may herein comprise substitutions, insertions, deletions, additional N- or C-terminal amino acids, and/or additional chemical moieties, such as carbohydrates, to increase stability, solubility, and immunogenicity.

In one embodiment of the invention, the present immunogenic polypeptides as defined herein, are glycosylated. Without wishing to be bound by any particular theory, it is hypothesized herein that by glycosylation of these polypeptides the immunogenicity thereof may be increased. Therefore, in one embodiment, the aforementioned immunogenic polypeptide as defined herein before, is glycosylated, having a carbohydrate content varying from 10-80 wt %, based on the total weight of the glycoprotein or glycosylated polypeptide. More preferably said carbohydrate content ranges from 15-70 wt %, still more preferably from 20-60 wt %. In another embodiment, said glycosylated immunogenic polypeptide comprises a glycosylation pattern that is similar to that of the corresponding zona pellucida glycoprotein (or fragment thereof) of the human that is treated. It is hypothesized that this even further increases the immunogenicity of said polypeptide. Thus, it is preferred that the immunogenic polypeptide comprises a glycosylation pattern that is similar to that of the corresponding SAS1R glycoprotein.

In one embodiment, the source of a polypeptide comprises an effective amount of an immunogenic polypeptide selected from SAS1R protein, and immunologically active homologs thereof and fragments thereof, or a nucleic acid sequence encoding said immunogenic polypeptide.

In one embodiment, the present method of immunization comprises the administration of a source of immunogenically active polypeptide fragments, said polypeptide fragments being selected from SAS1R protein fragments and/or homologs thereof as defined herein before, said polypeptide fragments comprising dominant CTL and/or HTL epitopes and which fragments are between 18 and 45 amino acids in length. Peptides having a length between 18 and 45 amino acids have been observed to provide superior immunogenic properties as is described in WO 02/070006.

Peptides may advantageously be chemically synthesized and may optionally be (partially) overlapping and/or may also be ligated to other molecules, peptides, or proteins. Peptides may also be fused to form synthetic proteins, as in Welters et al. (Vaccine. 2004 Dec. 2; 23(3):305-11). It may also be advantageous to add to the amino- or carboxy-terminus of the peptide chemical moieties or additional (modified or D-) amino acids in order to increase the stability and/or decrease the biodegradability of the peptide. To improve immunogenicity, immuno-stimulating moieties may be attached, e.g. by lipidation or glycosylation. To enhance the solubility of the peptide, addition of charged or polar amino acids may be used, in order to enhance solubility and increase stability in vivo.

For immunization purposes, the aforementioned immunogenic polypeptides of the invention may also be fused with proteins, such as, but not limited to, tetanus toxin/toxoid, diphtheria toxin/toxoid or other carrier molecules. The polypeptides according to the invention may also be advantageously fused to heatshock proteins, such as recombinant endogenous (murine) gp96 (GRP94) as a carrier for immunodominant peptides as described in (references: Rapp U K and Kaufmann S H, Int Immunol. 2004 April; 16(4):597-605; Zugel U, Infect Immun. 2001 June; 69(6):4164-7) or fusion proteins with Hsp70 (Triebel et al; WO9954464).

The individual amino acid residues of the present immunogenic (poly)peptides of the invention can be incorporated in the peptide by a peptide bond or peptide bond mimetic. A peptide bond mimetic of the invention includes peptide backbone modifications well known to those skilled in the art. Such modifications include modifications of the amide nitrogen, the alpha carbon, amide carbonyl, complete replacement of the amide bond, extensions, deletions, or backbone crosslinks. See, generally, Spatola, Chemistry and Biochemistry of Amino Acids, Peptides and Proteins, Vol. VII (Weinstein ed., 1983). Several peptide backbone modifications are known and can be used in the practice of the invention.

Amino acid mimetics may also be incorporated in the polypeptides. An "amino acid mimetic" as used here is a moiety other than a naturally occurring amino acid that conformationally and functionally serves as a substitute for an amino acid in a polypeptide of the present invention. Such a moiety serves as a substitute for an amino acid residue if it does not interfere with the ability of the peptide to elicit an immune response against the native SAS1R T cell epitopes. Amino acid mimetics may include non-protein amino acids. A number of suitable amino acid mimetics are known to the skilled artisan, they include cyclohexylalanine, 3-cyclohexylpropionic acid, L-adamantyl alanine, adamantylacetic acid and the like. Peptide mimetics suitable for peptides of the present invention are discussed by Morgan and Gainor, (1989) Ann. Repts. Med. Chem. 24:243-252.*

In one embodiment, the present method comprises the administration of a composition comprising one or more of the present immunogenic polypeptides as defined herein above, and at least one excipient. Excipients are well known in the art of pharmacy and may for instance be found in textbooks such as Remington's pharmaceutical sciences, Mack Publishing, 1995.

The present method for immunization may further comprise the administration, and in one aspect, the co-administration, of at least one adjuvant. Adjuvants may comprise any adjuvant known in the art of vaccination and may be selected using textbooks like Current Protocols in Immunology, Wiley Interscience, 2004.

Adjuvants are herein intended to include any substance or compound that, when used, in combination with an antigen, to immunize a human or an animal, stimulates the immune system, thereby provoking, enhancing or facilitating the immune response against the antigen, preferably without generating a specific immune response to the adjuvant itself. In one aspect, adjuvants can enhance the immune response against a given antigen by at least a factor of 1.5, 2, 2.5, 5, 10, or 20, as compared to the immune response generated against the antigen under the same conditions but in the absence of the adjuvant. Tests for determining the statistical average enhancement of the immune response against a given antigen as produced by an adjuvant in a group of animals or humans over a corresponding control group are available in the art. The adjuvant preferably is capable of enhancing the immune response against at least two different antigens. The adjuvant of the invention will usually be a compound that is foreign to a human, thereby excluding immunostimulatory compounds that are endogenous to humans, such as e.g. interleukins, interferons, and other hormones.

A number of adjuvants are well known to one of ordinary skill in the art. Suitable adjuvants include, e.g., incomplete Freund's adjuvant, alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dip-almitoyl-sn-glycero-3-hydroxy-phosphoryloxy)-ethylamine (CGP 19835A, referred to as MTP-PE), DDA (2 dimethyldioctadecylammonium bromide), polyIC, Poly-A-poly-U, RIBI™, GERBU™, Pam3™, Carbopol™, Specol™, Titermax™, tetanus toxoid, diphtheria toxoid, meningococcal outer membrane proteins, diphtheria protein $CRM_{197}$. Preferred adjuvants comprise a ligand that is recognized by a Toll-like-receptor (TLR) present on antigen presenting cells. Various ligands recognized by TLR's are known in the art and include e.g. lipopeptides (see, e.g., WO 04/110486), lipopolysaccharides, peptidoglycans, liopteichoic acids, lipoarabinomannans, lipoproteins (from mycoplasma or spirochetes), double-stranded RNA (poly I:C), unmethylated DNA, flagellin, CpG-containing DNA, and imidazoquinolines, as well derivatives of these ligands having chemical modifications.

The methods of immunization of the present application further encompass the administration, including the co-administration, of a CD40 binding molecule in order to enhance a CTL response and thereby enhance the therapeutic effects of the methods and compositions of the invention. The use of CD40 binding molecules is described in WO 99/61065, incorporated herein by reference. The CD40 binding molecule is preferably an antibody or fragment thereof or a CD40 Ligand or a variant thereof, and may be added separately or may be comprised within a composition according to the current invention. Such effective dosages will depend on a variety of factors including the condition and general state of health of the patient. Thus, dosage regimens can be determined and adjusted by trained medical personnel to provide the optimum therapeutic or prophylactic effect.

In the present method, the one or more immunogenic polypeptides are typically administered at a dosage of about 1 ug/kg patient body weight or more at least once. Often dosages are greater than 10 ug/kg. According to the present invention, the dosages preferably range from 1 ug/kg to 1 mg/kg.

In one embodiment typical dosage regimens comprise administering a dosage of 1-1000 ug/kg, more preferably 10-500 ug/kg, still more preferably 10-150 ug/kg, once, twice or three times a week for a period of one, two, three, four or five weeks. According to one embodiment, 10-100 ug/kg is administered once a week for a period of one or two weeks.

The present method, in one aspect, comprises administration of the present immunogenic polypeptides and compositions comprising them via the injection, transdermal, or oral route. In another, embodiment of the invention, the present method comprises vaginal administration of the present immunogenic polypeptides and compositions comprising them.

Another aspect of the invention relates to a pharmaceutical preparation comprising as the active ingredient the present source of a polypeptide as defined herein before. More particularly pharmaceutical preparation comprises as the active ingredient one or more of the aforementioned immunogenic polypeptides selected from the group of SAS1R proteins, homologues thereof and fragments of said SAS1R proteins and homologs thereof, or, alternatively, a gene therapy vector as defined herein above.

The present invention further provides a pharmaceutical preparation comprising one or more of the immunogenic polypeptides of the invention. The concentration of said polypeptide in the pharmaceutical composition can vary widely, i.e., from less than about 0.1% by weight, usually being at least about 1% by weight to as much as 20% by weight or more.

The composition may comprise a pharmaceutically acceptable carrier in addition to the active ingredient. The pharmaceutical carrier can be any compatible, non-toxic substance suitable to deliver the immunogenic polypeptides or gene therapy vectors to the patient. For polypeptides, sterile water, alcohol, fats, waxes, and inert solids may be used as the carrier. Pharmaceutically acceptable adjuvants, buffering agents, dispersing agents, and the like, may also be incorporated into the pharmaceutical compositions.

In one embodiment, the present pharmaceutical composition comprises an adjuvant, as defined in more detail herein before. Adjuvants useful for incorporation in the present composition are preferably selected from the group of ligands that are recognized by a Toll-like-receptor (TLR) present on antigen presenting cells, including lipopeptides, lipopolysaccharides, peptidoglycans, liopteichoic acids, lipoarabinomannans, lipoproteins (from mycoplasma or spirochetes), double-stranded RNA (poly I:C), unmethylated DNA, flagellin, CpG-containing DNA, and imidazoquinolines, as well derivatives of these ligands having chemical modifications. The routineer will be able to determine the exact amounts of anyone of these adjuvants to be incorporated in the present pharmaceutical preparations in order to render them sufficiently immunogenic. According to another preferred embodiment, the present pharmaceutical preparation may comprise one or more additional ingredients that are used to enhance CTL immunity as explained herein before. According to a particularly preferred embodiment the present pharmaceutical preparation comprises a CD40 binding molecule.

Methods of producing pharmaceutical compositions comprising polypeptides are described in U.S. Pat. Nos. 5,789, 543 and 6,207,718. The preferred form depends on the intended mode of administration and therapeutic application.

In one embodiment, the present immunogenic proteins or polypeptides are administered by injection. The parenteral route for administration of the polypeptide is in accordance with known methods, e.g. injection or infusion by intravenous, intraperitoneal, intramuscular, intra-arterial, subcutaneous, or intralesional routes. The protein or polypeptide may be administered continuously by infusion or by bolus injection. A typical composition for intravenous infusion could be made up to contain 10 to 50 ml of sterile 0.9% NaCl or 5% glucose optionally supplemented with a 20% albumin solution and between 10 ug and 50 mg, preferably between 50 ug and 10 mg, of the polypeptide. A typical pharmaceutical composition for intramuscular injection would be made up to contain, for example, 1-10 ml of sterile buffered water and between 10 ug and 50 mg, preferably between 50 ug and 10 mg, of the polypeptide of the present invention. Methods for preparing parenterally administrable compositions are well known in the art and described in more detail in various sources, including, for example, Remington's Pharmaceutical Science (15th ed., Mack Publishing, Easton, Pa., 1980) (incorporated by reference in its entirety for all purposes).

For convenience, immune responses are often described in the present invention as being either "primary" or "secondary" immune responses. A primary immune response, which is also described as a "protective" immune response, refers to an immune response produced in an individual as a result of some initial exposure (e.g., the initial "immunization") to a particular antigen. Such an immunization can occur, for example, as the result of some natural exposure to the antigen (for example, from initial infection by some pathogen that exhibits or presents the antigen). Alternatively, the immunization can occur because of vaccinating the individual with a vaccine containing the antigen. For example, the vaccine can be a vaccine comprising one or more antigenic epitopes or fragments of SAS1R.

The vaccine can also be modified to express other immune activators such as IL2, and costimulatory molecules, among others.

Another type of vaccine that can be combined with antibodies to an antigen is a vaccine prepared from a cell lysate of interest, in conjunction with an immunological adjuvant, or a mixture of lysates from cells of interest plus DETOX™ immunological adjuvant. Vaccine treatment can be boosted with anti-antigen antibodies, with or without additional chemotherapeutic treatment.

When used in vivo for therapy, the antibodies of the subject invention are administered to the subject in therapeutically effective amounts (i.e., amounts that have desired therapeutic effect). They will normally be administered parenterally. The dose and dosage regimen will depend upon the degree of the infection, the characteristics of the particular antibody or immunotoxin used, e.g., its therapeutic index, the patient, and the patient's history. Advantageously the antibody or immunotoxin is administered continuously over a period of 1-2 weeks. Optionally, the administration is made during the course of adjunct therapy such as antimicrobial treatment, or administration of tumor necrosis factor, interferon, or other cytoprotective or immunomodulatory agent.

For parenteral administration, the antibodies will be formulated in a unit dosage injectable form (solution, suspension, emulsion) in association with a pharmaceutically acceptable parenteral vehicle. Such vehicles are inherently nontoxic, and non-therapeutic. Examples of such vehicle are water, saline, Ringer's solution, dextrose solution, and 5% human serum albumin. Nonaqueous vehicles such as fixed oils and ethyl oleate can also be used. Liposomes can be used as carriers. The vehicle can contain minor amounts of additives such as substances that enhance isotonicity and chemical stability, e.g., buffers and preservatives. The antibodies will typically be formulated in such vehicles at concentrations of about 1.0 mg/ml to about 10 mg/ml.

Use of IgM antibodies can be preferred for certain applications; however, IgG molecules by being smaller can be more able than IgM molecules to localize to certain types of infected cells.

There is evidence that complement activation in vivo leads to a variety of biological effects, including the induction of an inflammatory response and the activation of macrophages (Unanue and Benecerraf, Textbook of Immunology, 2nd Edition, Williams & Wilkins, p. 218 (1984)). The increased vasodilation accompanying inflammation can increase the ability of various agents to localize. Therefore, antigen-antibody combinations of the type specified by this invention can be used in many ways. Additionally, purified antigens (Hakomori, Ann. Rev. Immunol. 2:103, 1984) or anti-idiotypic antibodies (Nepom et al., Proc. Natl. Acad. Sci. USA 81: 2864, 1985; Koprowski et al., Proc. Natl. Acad. Sci. USA 81: 216, 1984) relating to such antigens could be used to induce an active immune response in human patients.

The antibody compositions used are formulated and dosages established in a fashion consistent with good medical practice taking into account the condition or disorder to be treated, the condition of the individual patient, the site of delivery of the composition, the method of administration, and other factors known to practitioners. The antibody compositions are prepared for administration according to the description of preparation of polypeptides for administration, infra.

As is well understood in the art, biospecific capture reagents include antibodies, binding fragments of antibodies which bind to activated integrin receptors on metastatic cells (e.g., single chain antibodies, Fab' fragments, F(ab)'2 fragments, and scFv proteins and affibodies (Affibody, Teknikringen 30, floor 6, Box 700 04, Stockholm SE-10044, Sweden; See U.S. Pat. No. 5,831,012, incorporated herein by reference in its entirety and for all purposes)). Depending on intended use, they also can include receptors and other proteins that specifically bind another biomolecule.

The hybrid antibodies and hybrid antibody fragments include complete antibody molecules having full length heavy and light chains, or any fragment thereof, such as Fab, Fab', F(ab')2, Fd, scFv, antibody light chains and antibody heavy chains. Chimeric antibodies which have variable regions as described herein and constant regions from various species are also suitable. See for example, U.S. Application No. 20030022244.

Initially, a predetermined target object is chosen to which an antibody can be raised. Techniques for generating monoclonal antibodies directed to target objects are well known to those skilled in the art. Examples of such techniques include, but are not limited to, those involving display libraries, xeno or humab mice, hybridomas, and the like. Target objects include any substance which is capable of exhibiting antigenicity and are usually proteins or protein polysaccharides. Examples include receptors, enzymes, hormones, growth factors, peptides and the like. It should be understood that not only are naturally occurring antibodies suitable for use in accordance with the present disclosure, but engineered antibodies and antibody fragments which are directed to a predetermined object are also suitable.

The present application discloses compositions and methods for inhibiting the proteins described herein, and those not disclosed which are known in the art are encompassed within the invention. For example, various modulators/effectors are known, e.g. antibodies, biologically active nucleic acids, such as antisense molecules, RNAi molecules, or ribozymes, aptamers, peptides or low-molecular weight organic compounds recognizing said polynucleotides or polypeptides, as well as the protein itself and fragments thereof.

The present invention further encompasses the identification of functional fragments for the use of SAS1R for use as antigens for therapeutic antibodies as well as its use as an immunogen and as an anticancer vaccine.

In one embodiment, a mimotope analysis of full length SAS1R can be performed by subdividing the sequence into, for example, a series of 15 amino acid peptides, with each peptide overlapping by three amino acids. All peptides can be biotinylated and allowed to bind to streptavidin-coated wells in 96-well plates. The reactivity of various antisera can be detected by enzyme-linked immunosorbent assay (ELISA). After blocking non-specific binding, SAS1R antibody can be added sequentially (i.e., either affinity-purified anti-SAS1R or affinity-purified anti-full-length recombinant SAS1R), followed by the sequential addition of peroxidase-conjugated secondary antibody, and peroxidase substrate.

The optical density of each well can be read at 450 nm and duplicate wells averaged. The average value obtained from a similar ELISA using control serum (i.e., preimmune serum) can be subtracted from the test Ig values and the resultant values plotted to determine which linear epitopes are recognized by the Ig.

The second and third components in the strategy to identify functional fragments of SAS1R rely on the synthesis of non-biotinylated peptides corresponding to the epitopes (peptides) predicted by the mimotope analysis. To determine whether any of the epitopes recognized by mimotope analysis are exposed on the egg, immunocytochemical staining with the Ig, without and with each of the peptides, can performed.

Methods for reducing fertility in females using peptides can be found, for example, in Klinefelter (U.S. patent application Ser. No. 11/572,453, filed Feb. 19, 2008, based on international patent application PCT/US2005/026102, filed Jul. 22, 2005).

Pharmaceutical Compositions and Administration

The present invention is also directed to pharmaceutical compositions comprising the compounds of the present invention. More particularly, such compounds can be formulated as pharmaceutical compositions using standard pharmaceutically acceptable carriers, fillers, solublizing agents and stabilizers known to those skilled in the art.

The invention is also directed to methods of administering the compounds of the invention to a subject. In one embodiment, the invention provides a method of treating a subject by administering compounds identified using the methods of the invention description. Pharmaceutical compositions comprising the present compounds are administered to a subject in need thereof by any number of routes including, but not limited to, topical, oral, intravenous, intramuscular, intraarterial, intramedullary, intrathecal, intraventricular, transdermal, subcutaneous, intraperitoneal, intranasal, enteral, topical, sublingual, or rectal means.

In accordance with one embodiment, a method of treating a subject in need of such treatment is provided. The method comprises administering a pharmaceutical composition comprising at least one compound of the present invention to a subject in need thereof. Compounds identified by the methods of the invention can be administered with known compounds or other medications as well.

The invention also encompasses the use of pharmaceutical compositions of an appropriate compound, and homologs, fragments, analogs, or derivatives thereof to practice the methods of the invention, the composition comprising at least one appropriate compound, and homolog, fragment, analog, or derivative thereof and a pharmaceutically-acceptable carrier.

The pharmaceutical compositions useful for practicing the invention may be administered to deliver a dose of between 1 ng/kg/day and 100 mg/kg/day.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

It will be understood by the skilled artisan that such pharmaceutical compositions are generally suitable for administration to animals of all sorts. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys. The invention is also contemplated for use in contraception for nuisance animals such as rodents.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically, dosages of the compound of the invention which may be administered to an animal, preferably a human, range in amount from 1 µg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the condition or disease being treated, the type and age of the animal, etc.

Suitable preparations of vaccines include injectables, either as liquid solutions or suspensions, however, solid forms suitable for solution in, suspension in, liquid prior to injection, may also be prepared. The preparation may also be emulsified, or the polypeptides encapsulated in liposomes. The active immunogenic ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants which enhance the effectiveness of the vaccine.

The invention is also directed to methods of administering the compounds of the invention to a subject. In one embodiment, the invention provides a method of treating a subject by administering compounds identified using the methods of the invention. Pharmaceutical compositions comprising the present compounds are administered to an individual in need thereof by any number of routes including, but not limited to, topical, oral, intravenous, intramuscular, intra arterial, intramedullary, intrathecal, intraventricular, transdermal, subcutaneous, intraperitoneal, intranasal, enteral, topical, sublingual, or rectal means.

In accordance with one embodiment, a method of treating and vaccinating a subject in need of such treatment is provided. The method comprises administering a pharmaceutical composition comprising at least one compound of the present invention to a subject in need thereof. Compounds identified by the methods of the invention can be administered with known compounds or other medications as well.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate, and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

A variety of vaginal drug delivery systems is known in the art. Suitable systems include creams, foams, tablets, gels, liquid dosage forms, suppositories, and pessaries. Mucoadhesive gels and hydrogels, comprising weakly crosslinked polymers which are able to swell in contact with water and spread onto the surface of the mucosa, have been used for vaccination with peptides and proteins through the vaginal route previously. The present invention further provides for the use of microspheres for the vaginal delivery of peptide and protein drugs. More detailed specifications of vaginally administered dosage forms including excipients and actual methods of preparing said dosage forms are known, or will be apparent, to those skilled in this art. For example, Remington's Pharmaceutical Sciences (15th ed., Mack Publishing, Easton, Pa., 1980) is referred to.

The invention also includes a kit comprising the composition of the invention and an instructional material which describes adventitially administering the composition to a cell or a tissue of a mammal. In another embodiment, this kit comprises a (preferably sterile) solvent suitable for dissolving or suspending the composition of the invention prior to administering the compound to the mammal.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the peptide of the invention or be shipped together with a container which contains the peptide. Alternatively, the instructional material may be shipped separately from the container with the intention that the instructional material and the compound be used cooperatively by the recipient.

Other techniques known in the art may be used in the practice of the present invention, including those described in international patent application WO 2006/091535 (PCT/US2006/005970), the entirety of which is incorporated by reference herein.

Imaging SAS1R Positive Tumors—

The present invention encompasses the preparation of complexes comprising antibodies, and fragments and homologs thereof, directed against SAS1R as peptide ligands, and at least one imaging agent such as a metal, radionuclide, etc., which are typically conjugated to a chelator in order to complex the imaging agent. Useful Antibodies directed against SAS1R can include polyclonal, monoclonal, and humanized, etc.

In certain embodiments, the imaging agent is attached to the complex by a chelator. In one aspect, the chelator is DOTA.

A number of trivalent metal radionuclides have physical properties suitable for radioisotope imaging (e.g., indium-111 ($^{111}$In), gallium-67/68 ($^{67/68}$Ga) and yttrium-86 ($^{86}$Y) or for targeted radionuclide therapy (e.g., $^{90}$Y and lutetium-177 ($^{177}$Lu)). These metal radionuclides can be combined with a targeting biomolecule (such as a peptide or antibody) in order to diagnose, monitor or treat disease. To obtain a radiolabeled biomolecule with the required stability, the peptide or protein must first be conjugated to a suitable chelator in order to complex the metal. The requirements of chelators for trivalent metals (such as In, Y, Ga and Lu) for labeling peptides are generally the same as those for labeling proteins. The complexes should be stable in biological systems and their chelating ability should not be impaired by reaction with the peptide. Most often, diethylenetriaminepentaacetic acid (DTPA) and/or 1,4,7,10-tetraazacyclododecane-1,4,7,10-tetraacetic acid (DOTA; CAS 60239-18-1) are used (see Choe and Lee, 2007, Current Pharmaceutical Design, 13:17-31; Li et al., 2007, J. Nuclear Medicine, "$^{64}$Cu-Labeled Tetrameric and Octameric RGD Peptides for Small-Animal PET of Tumor avb3 Integrin Expression", 48:1162-1171; Nahrendorf et al, 2009, JACC Cardiovasc. Imaging, 2:10:1213-1222; Li et al., 2009, Mol. Cancer. Ther., 8:5:1239-1249; Yim et al., 2010, J. Med. Chem., 53:3944-3953; Dijkgraaf et al., 2010, Eur. J. Nucl. Med. Mol. Imaging, published online 21 Sep., 2010; U.S. patent application Ser. No. 10/792,582; Dransfield et al., U.S. Pat. Pub. Nos. US 2010/0261875; U.S. Pat. No. 7,666, 979). Of the metals mentioned, the DOTA complexes are more thermodynamically and kinetically stable than the DTPA complexes (see Sosabowski et al., Nature Protocols 1, -972-976 (2006) and Leon-Rodriguez et al., Bioconjugate chemistry, Jan. 3, 2008; 19(2):391-402).

Chelating Agents

In some embodiments, a chelating agent may be attached to peptide, directly or indirectly, and used to chelate a therapeutic or diagnostic agent, such as a radionuclide. Exemplary chelators include but are not limited to DTPA (such as Mx-DTPA), DOTA, TETA, NETA or NOTA. Methods of conjugation and use of chelating agents to attach metals or other ligands to proteins are well known in the art (see, e.g., U.S. patent application Ser. No. 12/112,289, incorporated herein by reference in its entirety).

Useful chelators encompassed by the invention include, but are not limited to, DTPA, DO3A, DOTA, EDTA, TETA, EHPG, HBED, NOTA, DOTMA, TETMA, PDTA, TTHA, LICAM, HYNIC, and MECAM. HYNIC is particularly useful for chelating Tc99, another imaging agent of the invention.

Modifications

The present invention further provides for the use of molecules such as polyethylene glycol ("PEG") molecules as part of the complex. In one aspect, the PEG is about 20,000 m.w. or about less than about 20,000 m.w. In another aspect, the PEG is less than about 18,000 m.w. In yet another aspect, the PEG is less that about 16,000 m.w. In a further aspect, the PEG is less than about 14,000 m.w. In a further aspect, the PEG is less than about 12,000 m.w. In a further aspect, the PEG is less than about 10,000 m.w. In a further aspect, the PEG is less than about 8,000 m.w. In a further aspect, the PEG is less than about 7,000 m.w. In a further aspect, the PEG is less than about 6,000 m.w. In a further aspect, the PEG is less than about 5,000 m.w. In a further aspect, the PEG is less than about 4,000 m.w. In a further aspect, the PEG is less than about 3,000 m.w. In a further aspect, the PEG is less than about 2,000 m.w. In a further aspect, the PEG is less than about 1,000 m.w. In a further aspect, the PEG is less than about 500 m.w.

In one aspect, the PEG is PEG5000.

Peptide Modification and Preparation

Peptide preparation is described in the Examples. It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines ($-NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring or non-standard synthetic amino acids. The peptides of the invention are not limited to products of any of the specific exemplary processes listed herein.

The invention includes the use of beta-alanine (also referred to as β-alanine, β-Ala, bA, and βA, having the structure:

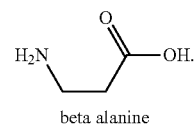

beta alanine

Sequences are provided herein which use the symbol "βA", but in the Sequence Listing submitted herewith "βA" is provided as "Xaa" and reference in the text of the Sequence Listing indicates that Xaa is beta alanine Peptides useful in the present invention, such as standards, or modifications for analysis, may be readily prepared by standard, well-established techniques, such as solid-phase peptide synthesis (SPPS) as described by Stewart et al. in *Solid Phase Peptide Synthesis,* 2nd Edition, 1984, Pierce Chemical Company, Rockford, Ill.; and as described by Bodanszky and Bodanszky in *The Practice of Peptide Synthesis,* 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well-known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide may be purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high performance liquid chromatography (HPLC) using an alkylated silica column such as $C_4$-, $C_9$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

As discussed, modifications or optimizations of peptide ligands of the invention are within the scope of the application. Modified or optimized peptides are included within the definition of peptide binding ligand. Specifically, a peptide sequence identified can be modified to optimize its potency, pharmacokinetic behavior, stability and/or other biological, physical and chemical properties.

Amino Acid Substitutions

In certain embodiments, the disclosed methods and compositions may involve preparing peptides with one or more substituted amino acid residues.

In various embodiments, the structural, physical and/or therapeutic characteristics of peptide sequences may be optimized by replacing one or more amino acid residues.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art. For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2', -3', or 4'-methyl-2, 3 or 4-biphenylalanine, and 2- or 3-pyridylalanine Substitution of amino acids containing basic functions: including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157:105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (O) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Tip. (See, e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

Linkers

Additionally, modifications encompassed by the invention include introduction of linkers or spacers between the targeting sequence of the binding moiety or binding polypeptide and the detectable label or therapeutic agent. For example, use of such linkers/spacers can improve the relevant properties of the binding peptides (e.g., increase serum stability, etc.). These linkers can include, but are not restricted to, substituted or unsubstituted alkyl chains, polyethylene glycol derivatives, amino acid spacers, sugars, or aliphatic or aromatic spacers common in the art.

For example, suitable linkers include homobifunctional and heterobifunctional cross-linking molecules. The homobifunctional molecules have at least two reactive functional groups, which are the same. The reactive functional groups on a homobifunctional molecule include, for example, aldehyde groups and active ester groups. Homobifunctional molecules having aldehyde groups include, for example, glutaraldehyde and subaraldehyde.

Homobifunctional linker molecules having at least two active ester units include esters of dicarboxylic acids and N-hydroxysuccinimide. Some examples of such N-succinimidyl esters include disuccinimidyl suberate and dithio-bis-(succinimidyl propionate), and their soluble bis-sulfonic acid and bis-sulfonate salts such as their sodium and potassium salts.

Heterobifunctional linker molecules have at least two different reactive groups. Some examples of heterobifunctional reagents containing reactive disulfide bonds include N-succinimidyl 3-(2-pyridyl-dithio)propionate (Carlsson et al., 1978. Biochem. J., 173:723-737), sodium S-4-succinimidyloxycarbonyl-alpha-methylbenzylthiosulfate, and 4-succinimidyloxycarbonyl-alpha-methyl-(2-pyridyldithio)toluene. N-succinimidyl 3-(2-pyridyldithio)propionate is preferred. Some examples of heterobifunctional reagents comprising reactive groups having a double bond that reacts with a thiol group include succinimidyl 4-(N-maleimidomethyl)cyclohexahe-1-carboxylate and succinimidyl m-maleimidobenzoate. Other heterobifunctional molecules include succinimidyl 3-(maleimido)propionate, sulfosuccinimidyl 4-(p-maleimido-phenyl)butyrate, sulfosuccinimidyl 4-(N-maleimidomethyl-cyclohexane)-1-carboxylate, maleimidobenzoyl-5N-hydroxy-succinimide ester.

Furthermore, linkers that are combinations of the molecules and/or moieties described above, can also be employed to confer special advantage to the properties of the peptide. Lipid molecules with linkers may be attached to allow formulation of ultrasound bubbles, liposomes or other aggregation based constructs. Such constructs could be employed as agents for targeting and delivery of a diagnostic reporter, a therapeutic agent (e.g., a chemical "warhead" for therapy), or a combination of these.

Constructs employing dimers, multimers, or polymers of one or more peptide ligands of the invention are also contemplated. Indeed, there is ample literature evidence that the binding of low potency peptides or small molecules can be substantially increased by the formation of dimers and multimers. Thus, dimeric and multimeric constructs (both homogeneous and heterogeneous) are within the scope of the instant invention. The polypeptide sequences in the dimeric constructs can be attached at their N- or C-terminus or the N-epsilon nitrogen of a suitably placed lysine moiety (or another function bearing a selectively derivatizable group such as a pendant oxyamino or other nucleophilic group), or can be joined together via one or more linkers (e.g., those discussed herein) employing the appropriate attachment chemistry. This coupling chemistry can include amide, urea, thiourea, oxime, or aminoacetylamide (from chloro- or bromoacetamide derivatives, but is not so limited). Linkers can also be used for attachment to a chelating agent.

Diagnosis by In Vivo Imaging

In a further aspect, the invention provides in vivo methods and compositions for diagnosing a cancer. The methods include identifying a subject at risk for or suspected of having a cancer expressing SAS1R; administering to a subject a diagnostic composition comprising an antibody/peptide ligand complex of the invention conjugated to an imaging molecule, and imaging the imaging molecule within the subject using in vivo imaging techniques. In some embodiments, the imaging molecule is a magnetofluorescent particle. In some embodiments, the magnetofluorescent particle comprises a near infrared (NIR) fluorochrome (NIRF). In some embodiments, the composition is administered via route selected from the group consisting of intradermal, subcutaneous, intraperitoneal, intravenous, intraarterial, oral, and gastric routes. In some embodiments, the in vivo imaging includes but is not limited to magnetic resonance imaging (MRI), intravital laser scanning microscopy, endoscopy, PET, SPECT/CT, and radiographic imaging. The invention further provides for monitoring the progression of cancer or during treatment of the cancer, including during carcinogenesis.

In one embodiment, the present invention further provides compositions and methods for monitoring the progression or treatment of a cancer.

In another embodiment, the present invention provides methods for surgically removing cancer cells. The methods include a) providing: i) a composition comprising an antibody/peptide ligand complex of the invention for distinguishing a cancer cell expressing SAS1R from a non-cancer cell; ii) to a subject known to have the cancer; iii) an in vivo imaging device; and b) administering the composition to the subject; c) imaging the SAS1R-expressing cells in vivo with the imaging device; and d) removing the cancer cells from the subject following detecting their location.

Therapeutic Agents

In other embodiments, therapeutic agents, including, but not limited to, cytotoxic agents, anti-angiogenic agents, pro-apoptotic agents, antibiotics, hormones, hormone antagonists, chemokines, drugs, prodrugs, toxins, enzymes or other agents may be used as adjunct therapies when using the antibody/peptide ligand complexes described herein. Drugs useful in the invention may, for example, possess a pharmaceutical property selected from the group consisting of antimitotic, antikinase, alkylating, antimetabolite, antibiotic, alkaloid, anti-angiogenic, pro-apoptotic agents and combinations thereof.

In another aspect, the present invention provides methods for identifying a cancer cell-binding partner having selective affinity for SAS1R. The methods include selectively immobilizing a diverse population of binding molecules to a solid support, contacting (e.g., simultaneously contacting) the diverse population immobilized on the solid support with one or more SAS1R peptides or cells expressing SAS1R and determining at least one binding molecule which selectively binds to one or more of the SAS1R peptide ligands, including those expressed by a bacteriophage. Also described herein are rapid and efficient methods for the identification of binding molecules that exhibit selective affinity for one or more SAS1R binding molecules of interest. The methods are advantageous in that they allow the simultaneous screening of multiple binding molecules. Moreover, very little information is required regarding the identity or function of either the binding molecule or the ligand for use in the present inventions. For example, diverse populations of binding molecules can be simultaneously screened against diverse populations of peptide ligands to rapidly identify numerous molecules exhibiting a desired binding specificity. The methods described herein can therefore be advantageously applied for the discovery of specific reagents, such as peptide ligands and biomarkers, for diagnosis and treatment of human diseases.

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

Imaging and Diagnostic Agents

Diagnostic agents are selected from, for example, the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters. Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III). Ultrasound contrast agents may comprise liposomes, such as gas filled liposomes. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerythrin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, i.e., protium ($^1$H), deuterium ($^2$H), or tritium ($^3$H) in any combination. Similarly, any carbon atom or set thereof in a molecule can be any of the isotopic form of carbons, such as $^{11}$C, $^{12}$C, $^{13}$C, or $^{14}$C, or any nitrogen atom or set thereof in a molecule can be any of the isotopic forms of nitrogen, such as $^{13}$N, $^{14}$N, or $^{15}$N. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or $^{14}$C radiolabeled sample where only some fraction of the set of molecules making up the macroscopic sample contains a radioactive atom. It is also understood that many elements that are not artificially isotopically enriched themselves are mixtures of naturally occurring isotopic forms, such as $^{14}$N and $^{15}$N, $^{32}$S and $^{34}$S, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, $^{14}$C and $^3$H can be prepared using neutrons generated in a nuclear reactor. Following nuclear transformation, $^{14}$C and $^3$H are incorporated into precursor molecules, followed by further elaboration as needed.

Techniques for detecting and measuring these agents are provided in the art or described herein.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

EXAMPLES

The following Examples disclose the results of studies designed to determine whether the protein SAS1R, which was known to be a tissue-specific and developmental-specific protein, might also be a protein that is dysregulated in cancer cells and perhaps be a cancer-oocyte antigen/biomarker.

General Materials and Methods—

HEK293 is a virally transformed cell line derived from human embryonic kidney cells grown in tissue culture.

Cell images and SAS1R detection can be done using techniques described herein or those known in the art. For example, after fixation, cells can be imaged using a Nikon TE 2000-E2 confocal microscope. Representative images can bee acquired using a 60X/1.45 Nikon oil immersion objective and MicroFire Picture Frame imaging software (Optronics, Galeta, Calif.). Images can be digitized and analyzed.

Various anti-SAS1R antibodies not described herein are also available, either commercially, or were previously described by this group. For example, mouse anti-V5 tag monoclonal antibody and c-terminal anti-his monoclonal antibody described in Herr et al. (PCT Pat. Pub. No. WO 2010/054187)

SAS1R, a Cancer-Oocyte Antigen in Uterine and Ovarian Tumors

See also PCT Pat. Pub. WO 2006/091535, Aug. 31, 2006; Herr et al., PCT Pat. Pub. WO 2010/054187, May 14, 2010).

The immunohistochemical data show that in mice and humans the SAS1R protein is restricted to the oocyte among normal tissues. This result is supported by the EST databanks showing expression of SAS1R messages only in ovary among normal tissues. SAS1R protein appears at the primary to secondary follicle transition during folliculogenesis.

Human SAS1R, contains the canonical zinc metalloproteinase motif of SEQ ID NO:26 (HEXXHXXGXXH), where G is replaced with X. It has 431 amino acid residues with a molecular weight of ~46 kDa. The domain structure includes a signal sequence followed by a propeptide domain, a metalloproteinase domain (catalytic domain), and a unique carboxyterminal domain.

The SAS1R protein is accessible on the surface of ovulated mouse and human oocytes (surface staining) that have undergone the M1-M2 transition; i.e., SAS1R is a cell surface protein (see Herr et al., WO 2010/054187). It also is found on the surface of CHO cells into which the full-length gene has been transfected. There is a transmembrane domain upstream of the catalytic domain that appears to be mediating this surface localization in mammals, but this transmembrane domain appears to be absent in the lower organisms. The SAS1R protein is an active metalloprotease enzyme.

SAS1R splice variants were demonstrated for the mouse (see Herr et al., WO 2010/054187). It is further demonstrated herein, that mouse SAS1R expression is specifically restricted to the ovary (specifically fertilized ovum, oocyte, unfertilized ovum, and zygote) based on a mouse SAS1R expression profile from EST database (FIG. 1). Additionally, examination of mouse SAS1R expression in a multi-tissue northern blot further demonstrated its restricted expression in ovary relative to brain, stomach, intestine, colon, liver lung, kidney, heart, skeletal muscle, spleen, testis, uterus, and placenta (FIG. 2).

Figure 4:
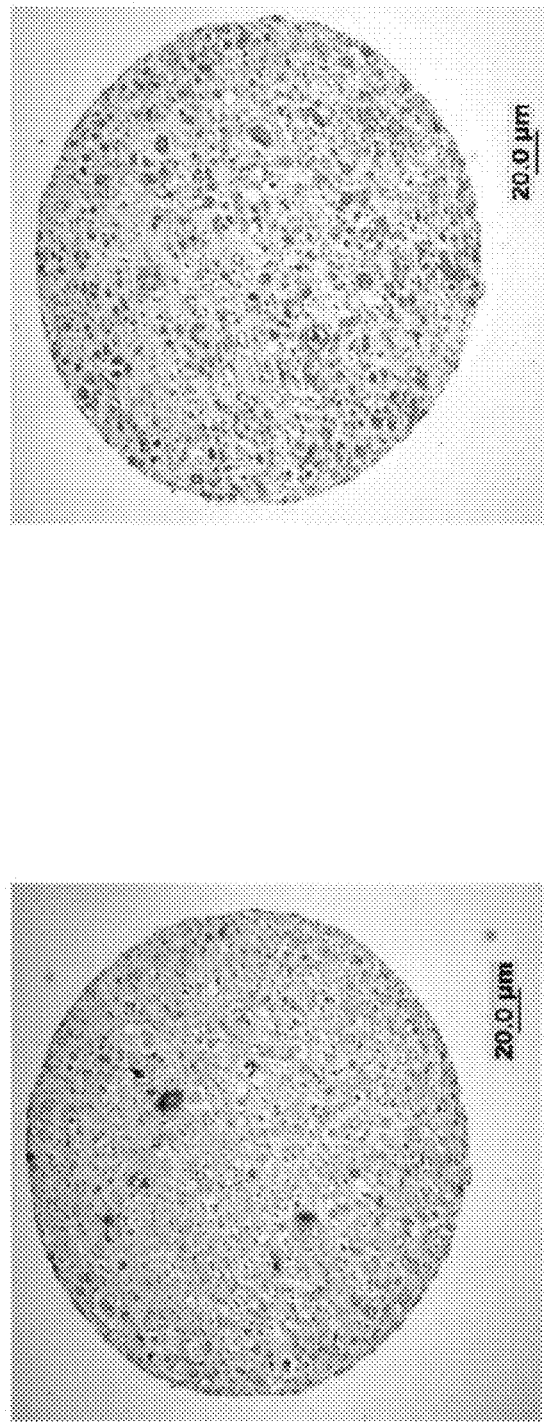
FIG. 4 demonstrates using immunolocalization techniques that SAS1R is indeed expressed in a malignant mixed mullerian tumor (MMMT). Left panel/micrograph—control; Right panel/micrograph—test.
Figure 5:
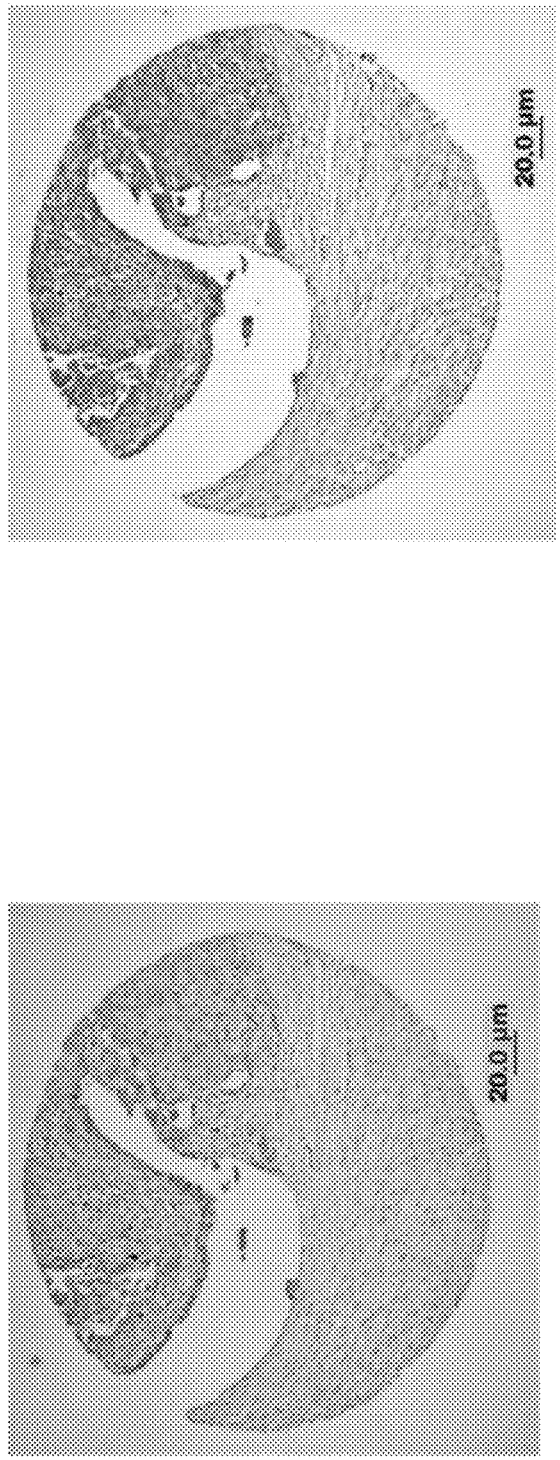
FIG. 5 demonstrates using immunolocalization techniques that SAS1R is indeed expressed in a malignant mixed mullerian tumor (MMMT). Left panel/micrograph—control; Right panel/micrograph—test.
Figure 6:
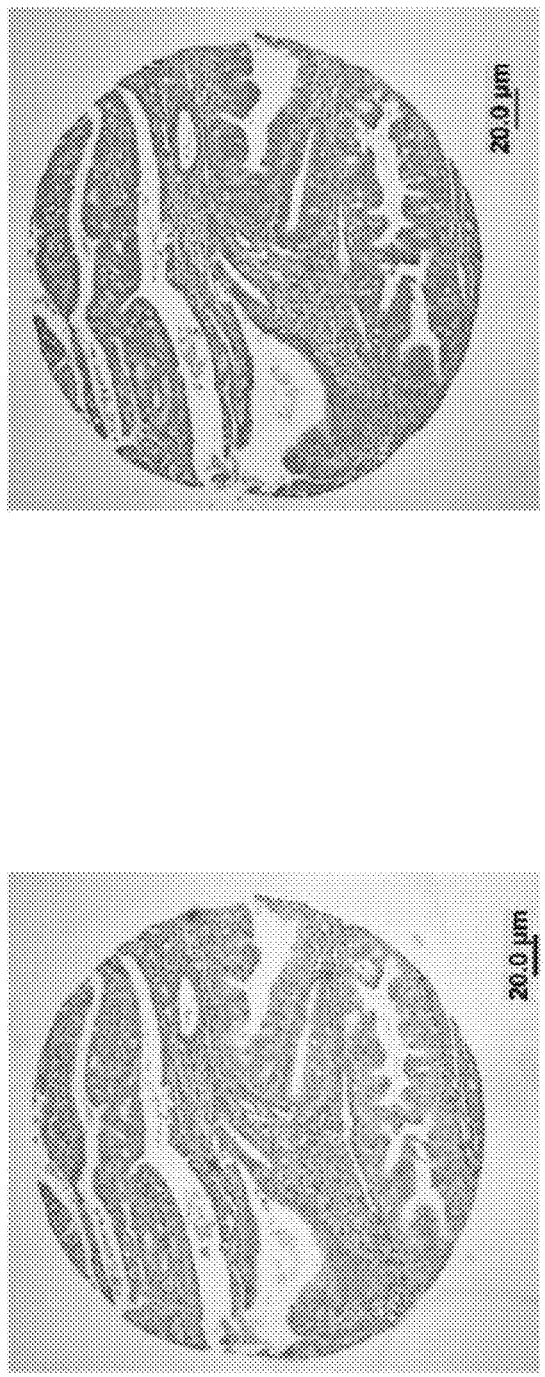
FIG. 6 demonstrates using immunolocalization techniques that SAS1R is also expressed in an endometrioid carcinoma. Left panel/micrograph-control; Right panel/micrograph—test.
Figure 7:
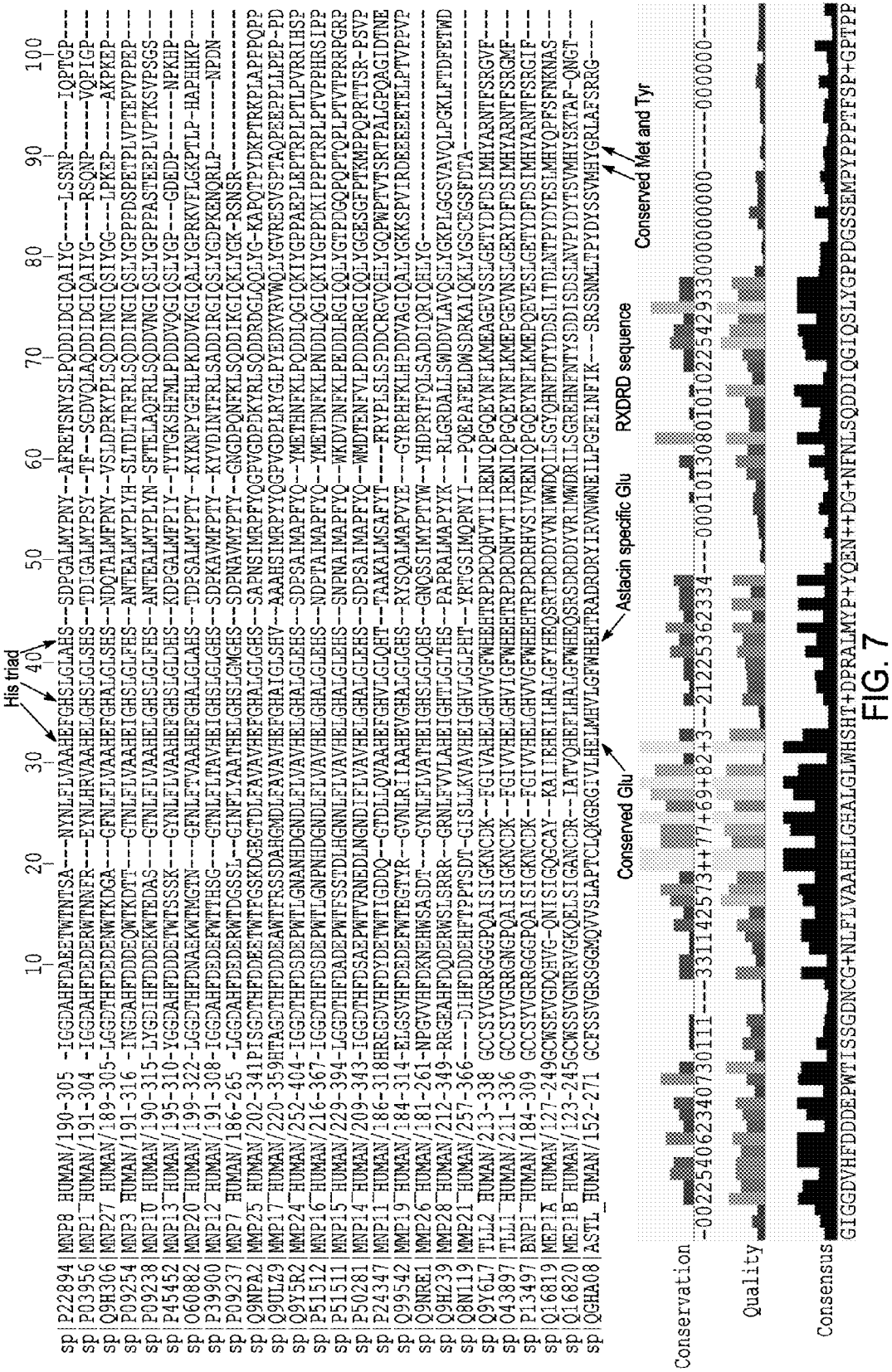
FIG. 7 provides a sequence comparison schematic of MMTs to SAS1R. Indicated are a conservation of the His triad for zinc liganding, and active site glutamate (Astacin specific glutamate, RXDRD, Met and Tyr residues). There was little sequence similarity between MMP and Astacin proteinase families.

Next, a human SAS1R expression profile from an EST database is provided (FIG. 3) and human SAS1R ESTs in GenBank are demonstrated herein to be found in uterine cancer. A series of studies were then performed to determine if SAS1R is expressed in human uterine tumors. FIGS. 4 and 5 demonstrate using immunolocalization techniques that SAS1R is indeed expressed in a malignant mixed mullerian tumor (MMMT). FIG. 6 demonstrates that SAS1R is also expressed in an endometrioid carcinoma. FIG. 7 provides a sequence comparison schematic of MMTs to SAS1R.

It was found that there is a conservation of the His triad for zinc liganding, and active site glutamate (Astacin specific glutamate, RXDRD, Met and Tyr residues). There was little sequence similarity between MMP and Astacin proteinase families. Without wishing to be bound by any particular theory, substrate binding may be different among the families. Therefore, SAS1R is a target for developing selective inhibitors that do not affect other members of the broad astacin family.

Figure 8:
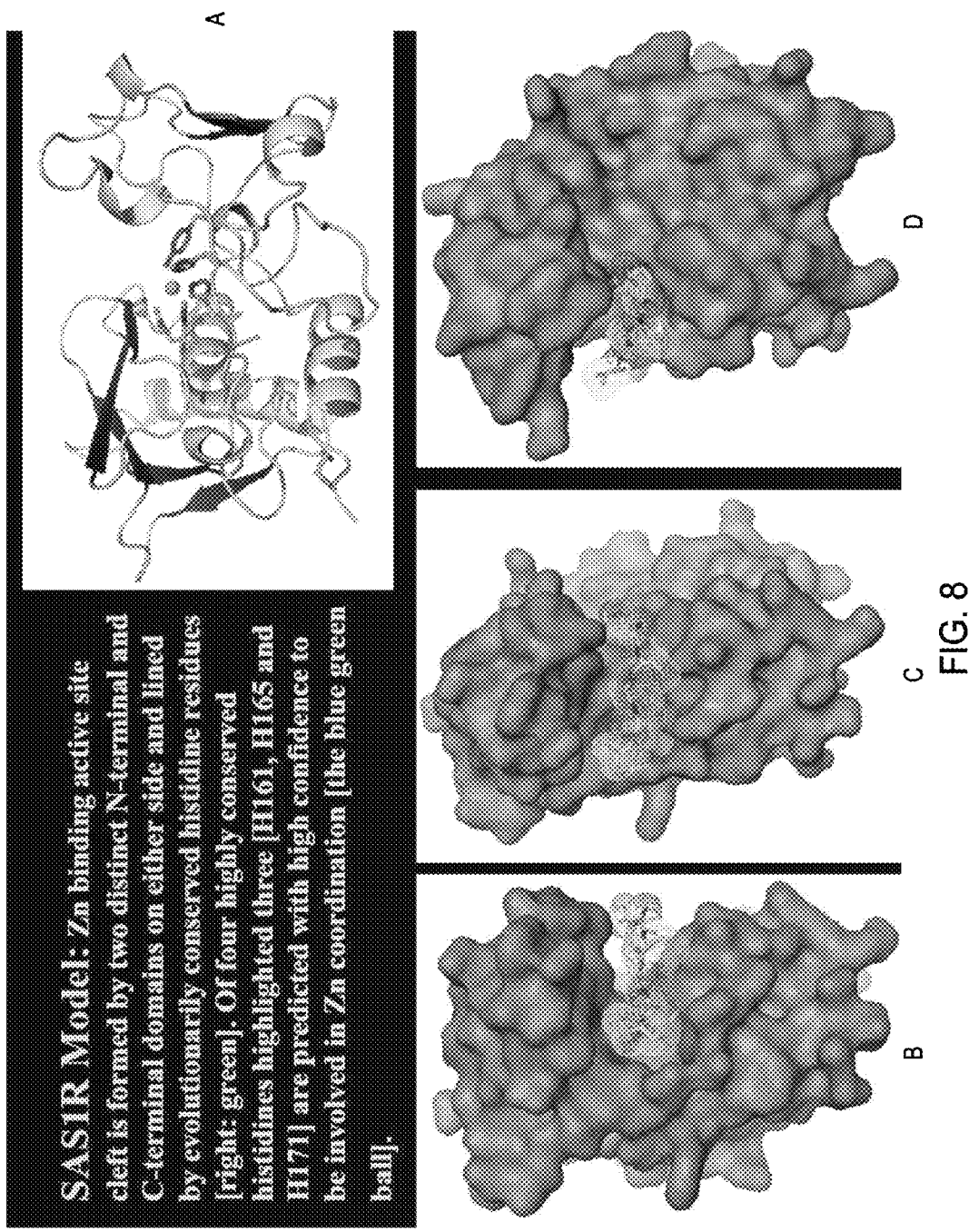
FIG. 8, comprising panels A-D, provides a structural model of SAS1R. The Zn binding active site cleft is formed by two distinct N-terminal and C-terminal domains on either side and lined by evolutionarily conserved histidine residues (on the right, and green in the color version). Of four highly conserved histidines highlighted, three of them (H161, H165, and H171) are predicted with high confidence to be involved in Zn coordination (it is a blue green ball in the color version of the model).

FIG. 8 provides a structural model of SAS1R. The Zn binding active site cleft is formed by two distinct N-terminal and C-terminal domains on either side and lined by evolutionarily conserved histidine residues (on the right, and green in the color version). Of four highly conserved histidines highlighted, three of them (H161, H165, and H171) are predicted with high confidence to be involved in Zn coordination (it is a blue green ball in the color version of the model).

Figure 9:
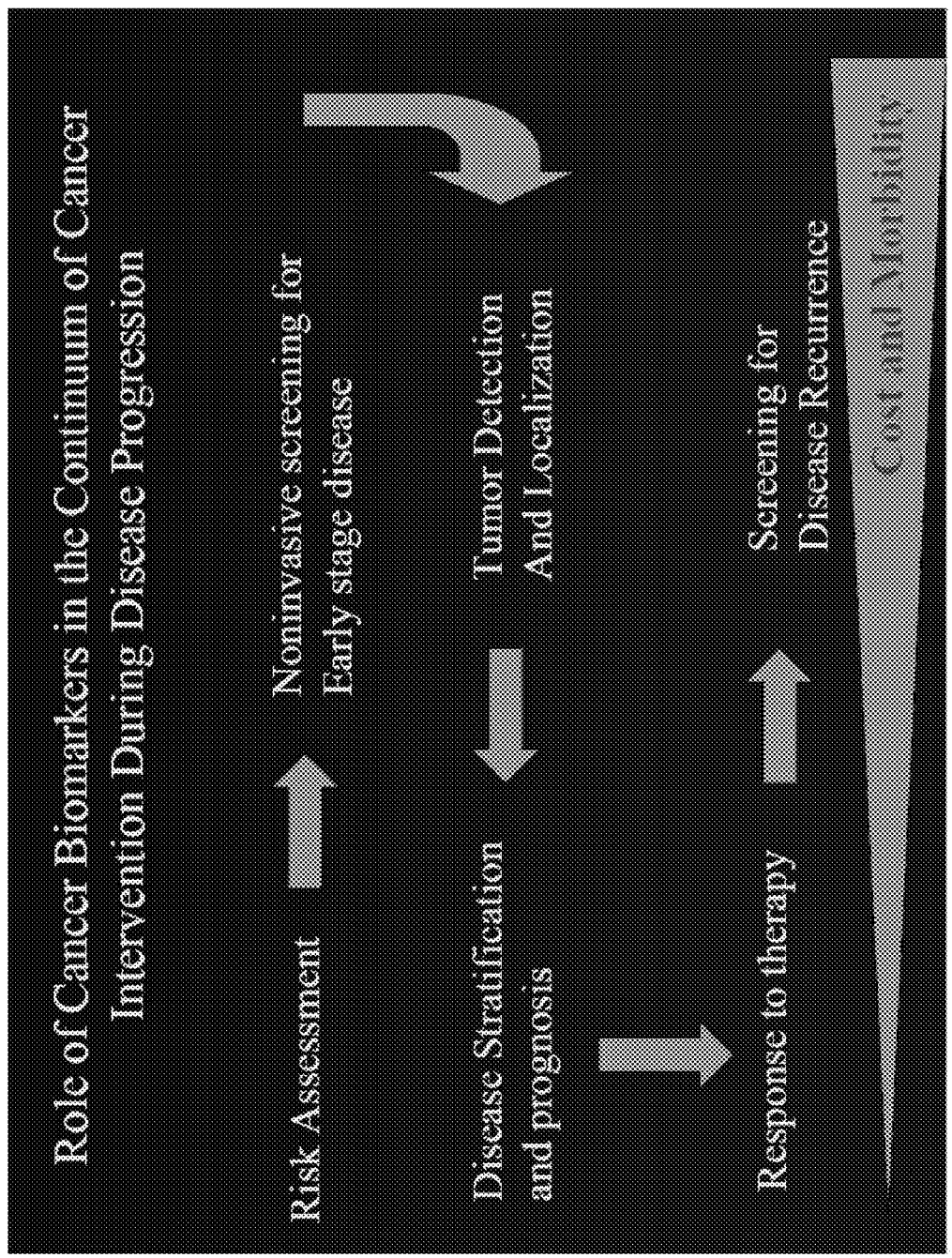
FIG. 9 provides a schematic illustration of the role of cancer biomarkers in the continuum of cancer intervention during disease progression.

FIG. 9 provides a schematic illustration of the role of cancer biomarkers in the continuum of cancer intervention during disease progression.

A series of experiments were performed to further examine SAS1R expression in uterine tumors and uterine cancer cells.

MMMT Cell Lines—
SNU539 mMMT (MMMT 539)—Korean homologous tumor absence of estrauterine elements like chondrosarcoma and osteosarcoma. It is an established cell line.
MMMT 308
MAD10—the cell line is a primary endometrium stromal cell line from normal donor and immortalized with hTERT and is used as a control cell.

The present application provides the novel primers for identifying and diagnosing cancers expressing SAS1R (SAS1B). Primers 1,2 (1F and 2R)=pro-peptide domain, 237 bp product. Primers 3,4 (3F and 4R)=c-term domain 309 bp product. Primers 5,6 (5F and 6R)=catalytic domain 579 bp product.

TOPO Cloning and Sequencing—

For TOPO cloning, PCR product was eluted and cloned in TOPO vector for transformation in TOP10 cells. White colonies were picked up next day for miniprep and digested with EcoRI restriction enzyme. They were then sequenced. Sequencing confirmed the identity of the gene to be SAS1R with 99% identity using excised products from normal human ovary and ovarian/uterine tumors. No other gene shared any sequence homology with the primer set (six primers—see below) designed by us for amplification and thereby confirmed by gene sequencing, including any other astacin family member or any of the 135 or so known metalloproteases.

The primers (SEQ ID NOs:28-33) used are as follows:

```
1F
GCGCCCCTGGCCTCCAGCTGCGCA

2R
CACGACACCACTACCACCCATGGG

3F
GGCTGCAGCCCAAGTGGCCCCAGG

4R
AGCAACACCGGGGGCACCTGCTCC

5F
GAGGTCCCCTTCCTGCTCTCCAGC

6R
GGCATGGGACCCTCTCCCACGGGG.
```

The invention encompasses other primers as well that are useful for identifying, diagnosing, and monitoring the progression and treatment of cancers expressing SAS1R.

Figure 10:
FIG. 10 demonstrates the electrophoretic results of PCR amplification for two MMMT uterine tumor cell lines and a normal control (MMMT 308, MMMT 539, and MAD10), with primers 1 and 2. 237 bp—upper gel; 130 bp GAPDH control—lower gel FIG. 11 demonstrates the electrophoretic results of PCR amplification for two MMMT uterine tumor cell lines and a normal control (MMMT 308, MMMT 539, and MAD10), for primers 3 and 4. 309 bp—upper gel; 130 bp GAPDH control-lower gel FIG. 12 demonstrates the electrophoretic results of PCR amplification for two MMMT uterine tumor cell lines and a normal control (MMMT 308, MMMT 539, and MAD10), for primers 5 and 6. 579 bp—upper gel; 130 bp GAPDH control-lower gel FIG. 13 demonstrates the results of a sequence analysis of MMMT 308 F.
Figure 11:
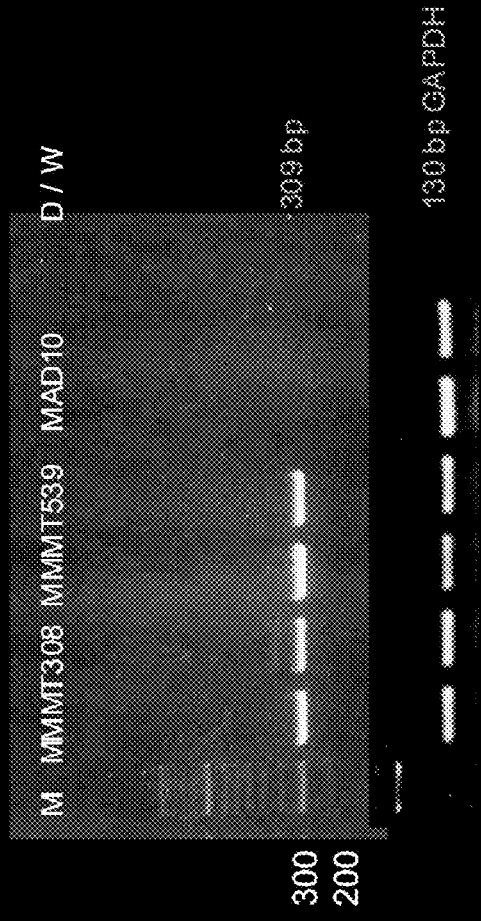
Figure 12:
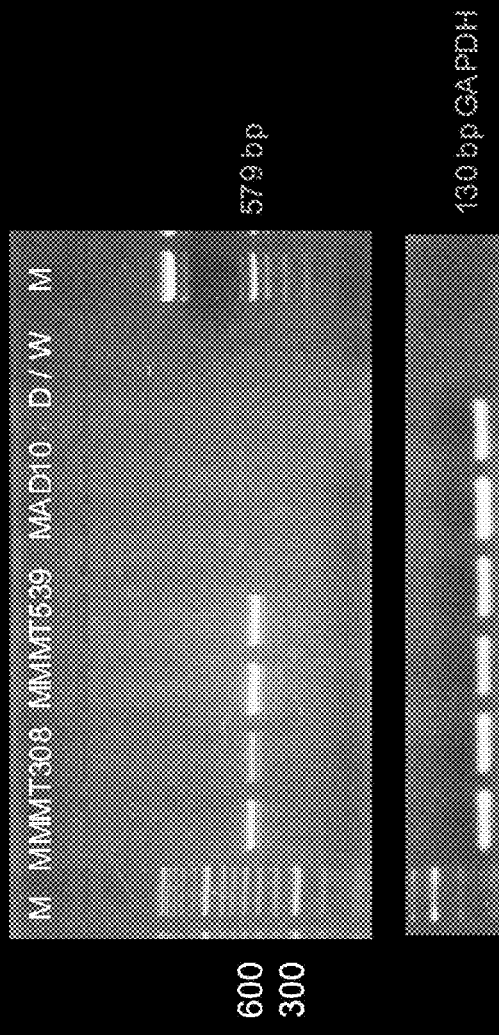

FIGS. 10, 11, and 12 show the results of PCR amplification for two MMMT uterine tumor cell lines and a normal control (MMMT 308, MMMT 539, and MAD10), for primers 1 and 2, primers 3 and 4, and primers 5 and 6, respectively.

Figure 13:
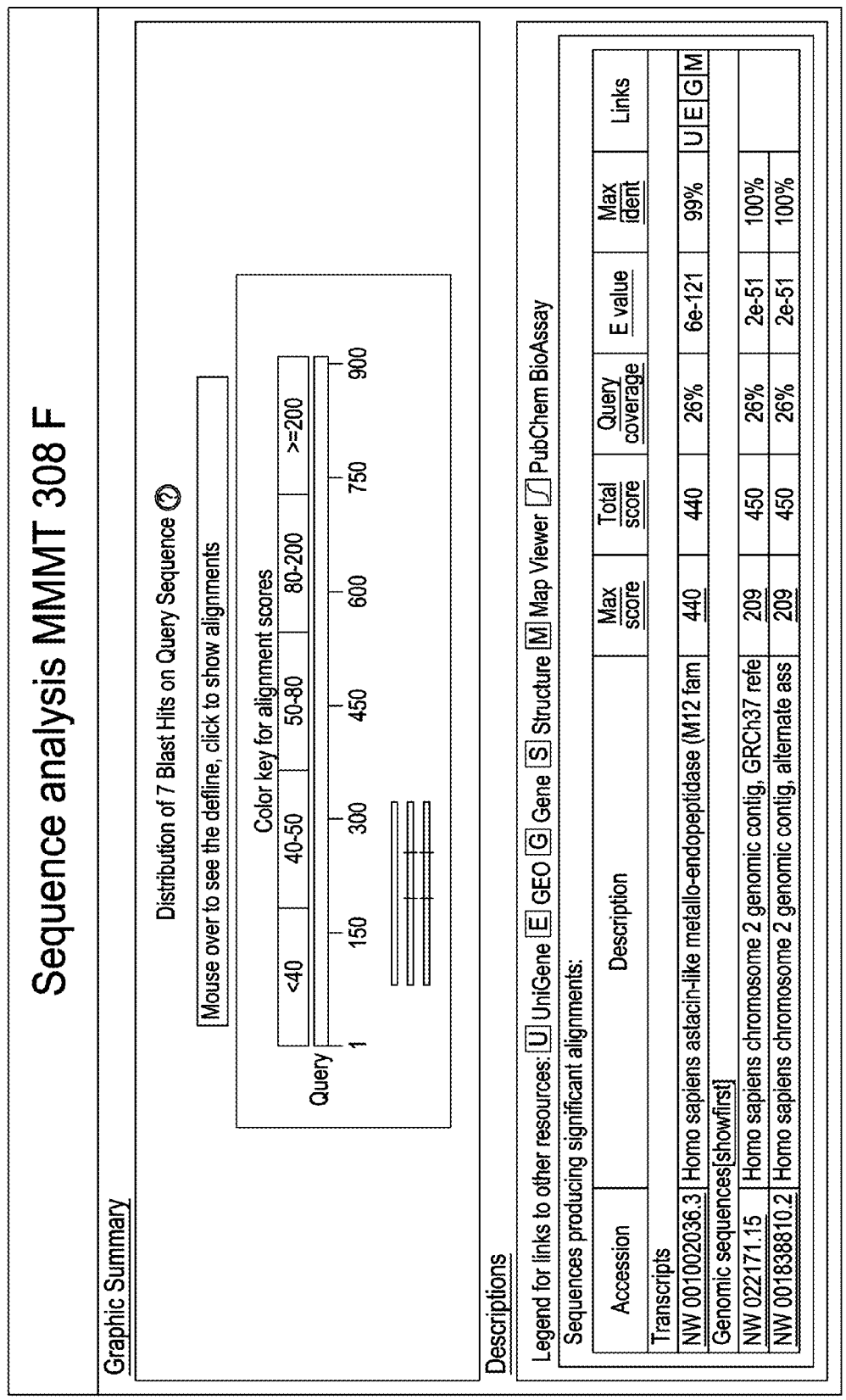

FIG. 13 demonstrates the results of a sequence analysis of MMMT 308 F.

Figure 14:
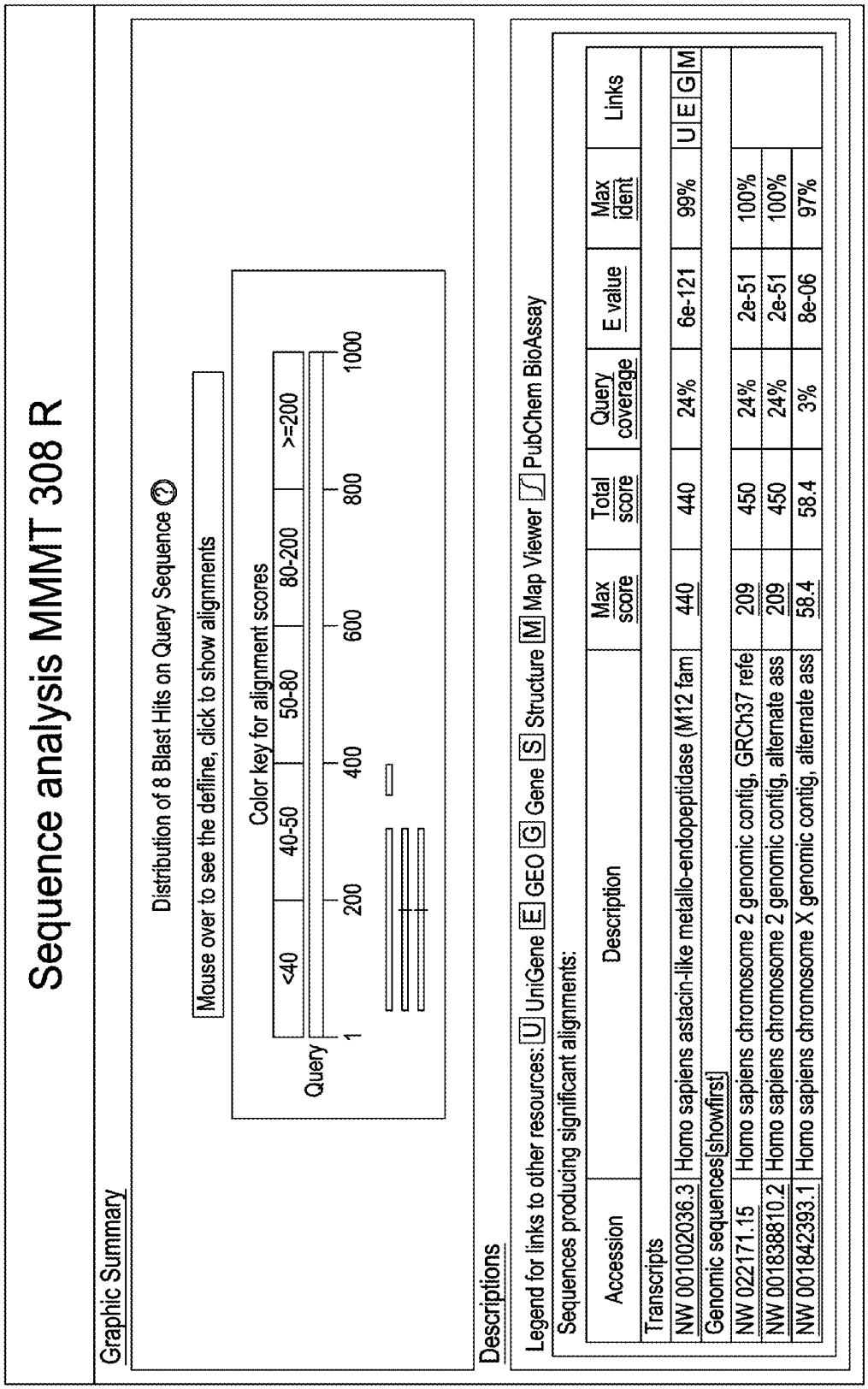
FIG. 14 demonstrates the results of a sequence analysis of MMMT 308 R.

FIG. 14 demonstrates the results of a sequence analysis of MMMT 308 R.

Figure 15:
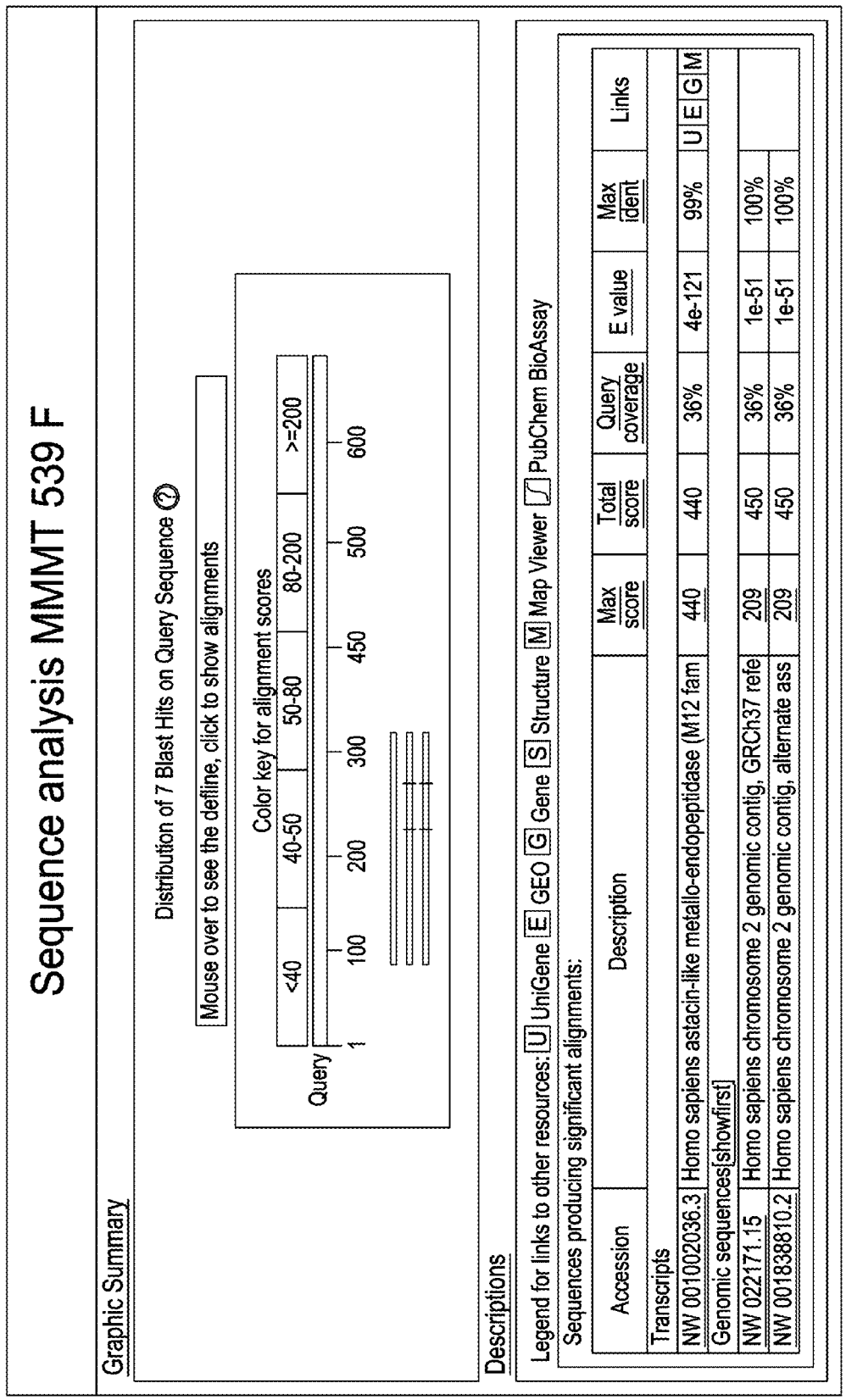
FIG. 15 demonstrates the results of a sequence analysis of MMMT 539 F.

FIG. 15 demonstrates the results of a sequence analysis of MMMT 539 F.

Figure 16:
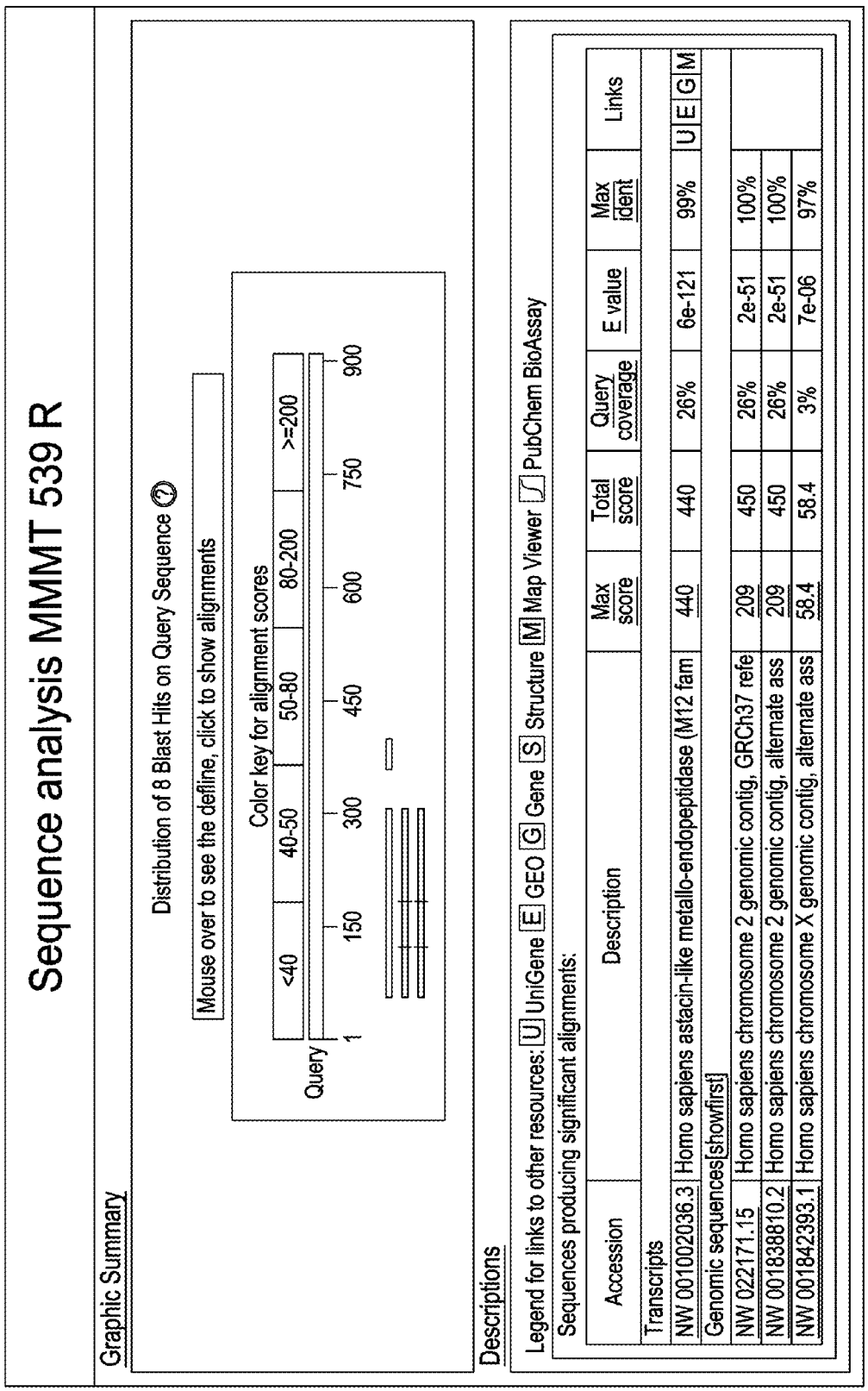
FIG. 16 demonstrates the results of a sequence analysis of MMMT 539 R.

FIG. 16 demonstrates the results of a sequence analysis of MMMT 539 R.

Antibodies were prepared against SAS1R, including a rabbit polyclonal. This laboratory has prepared antibodies against SAS1R previously as well (Herr et al., WO 2010/054187). Other reagents for use in studying SAS1R are commercially available, although they are generally referred to by the providers by the name ASTL. For example, Abcam provides rabbit anti-ASTL antibodies against the propeptide domain, catalytic domain, and a general antibody, which can be used in western blots and in immunohistochemistry. Santa Cruz Biotechnology provides anti-ASTL antibodies useful for western blotting, immunoprecipitation, immunofluorescence, and ELISA. Sigma-Aldrich provides an antibody useful for immunohistochemistry and in protein arrays.

Figure 17:
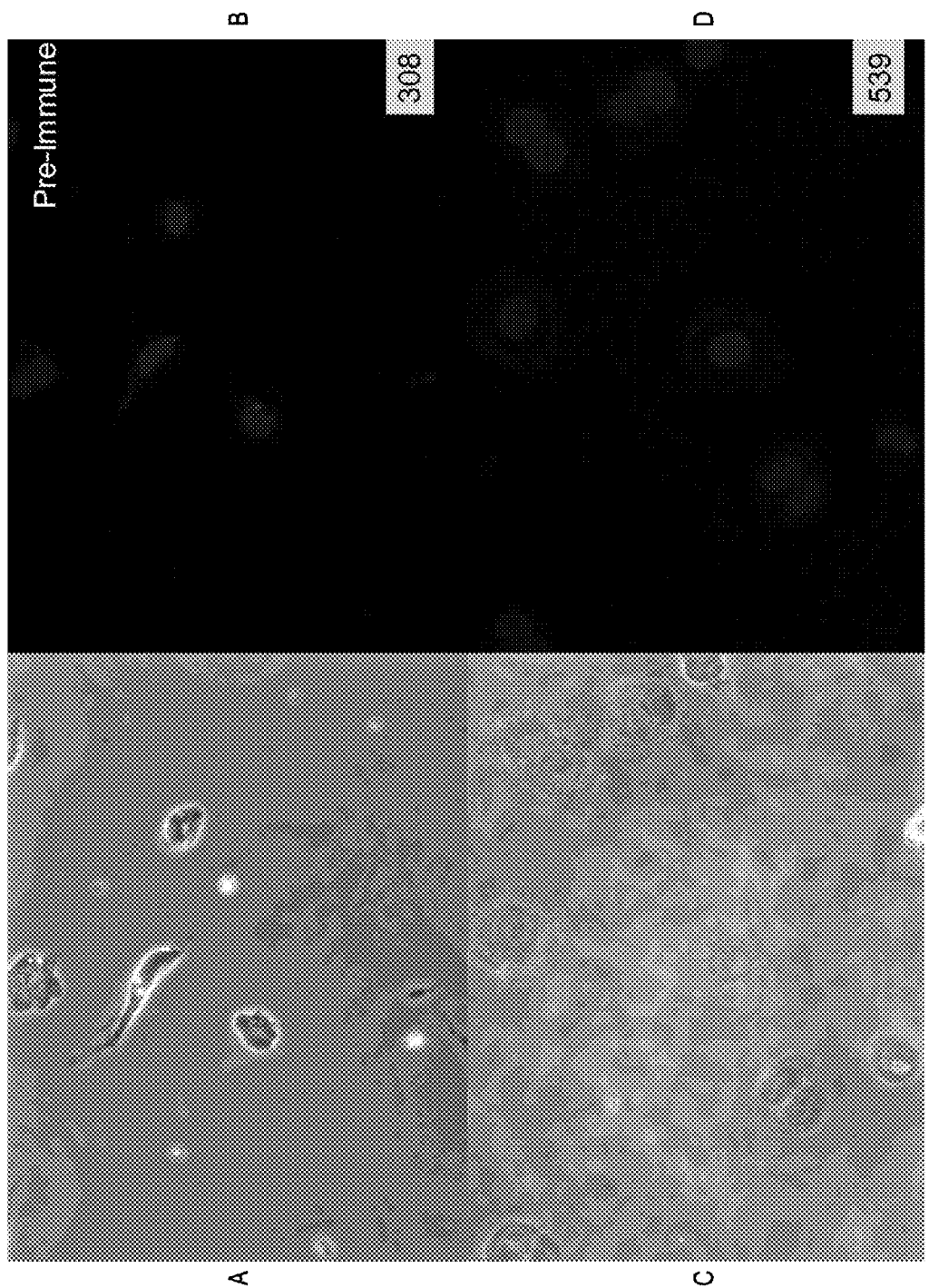
FIG. 17, comprising micrographs A-D, provides the control (pre-immune) results of expression of SAS1R in MMMT 308 and MMMT 539 cell lines using indirect immunofluorescence (panels A-D; upper-308; lower-539; A and C-phase contrast; B and D—pre-immune).
Figure 18:
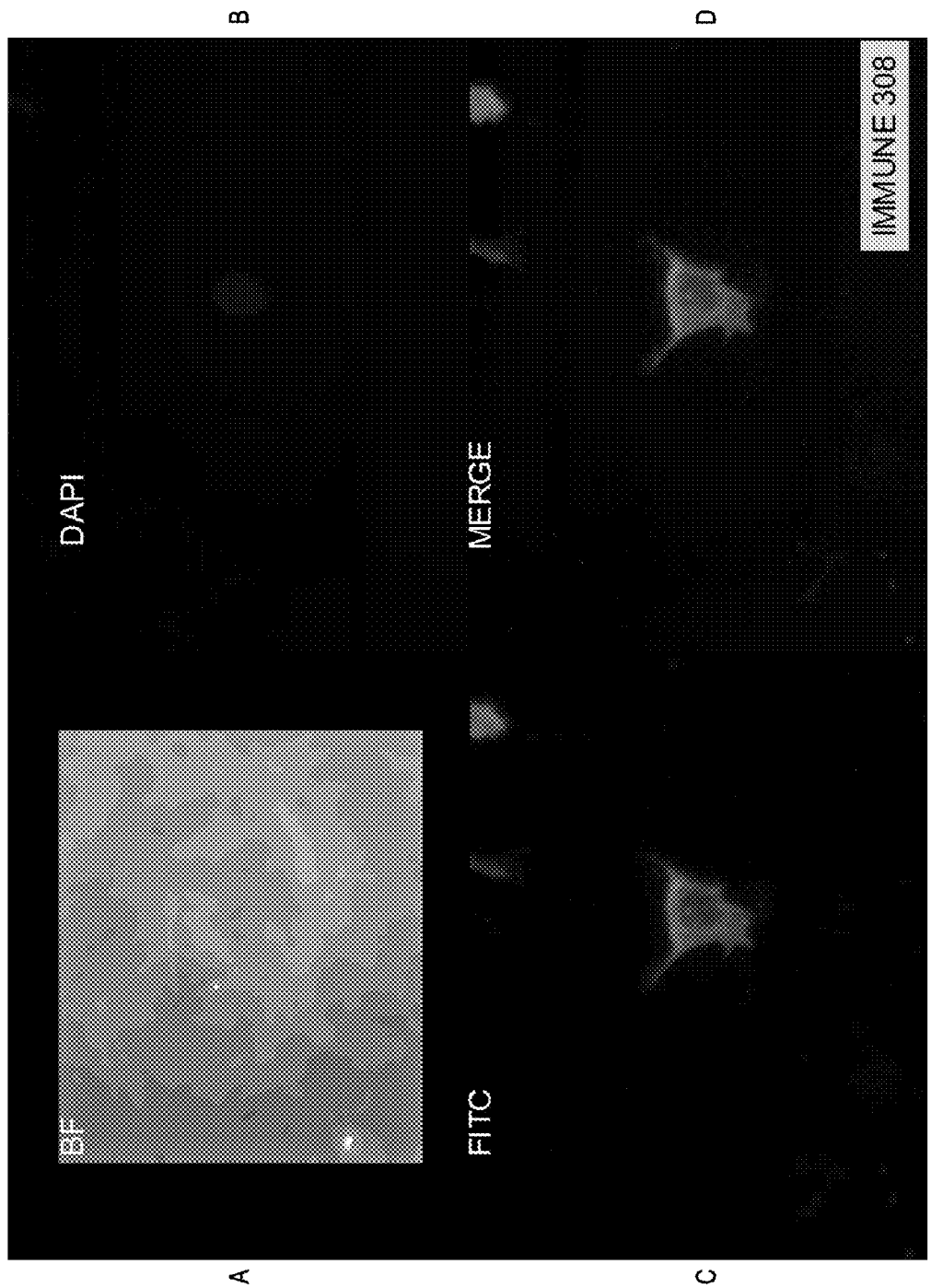
FIG. 18, comprising micrographs A-D, provides the BF (A), DAPI (B), FITC (C) and Merged (D) images for the immune staining of MMMT 308.
Figure 19:
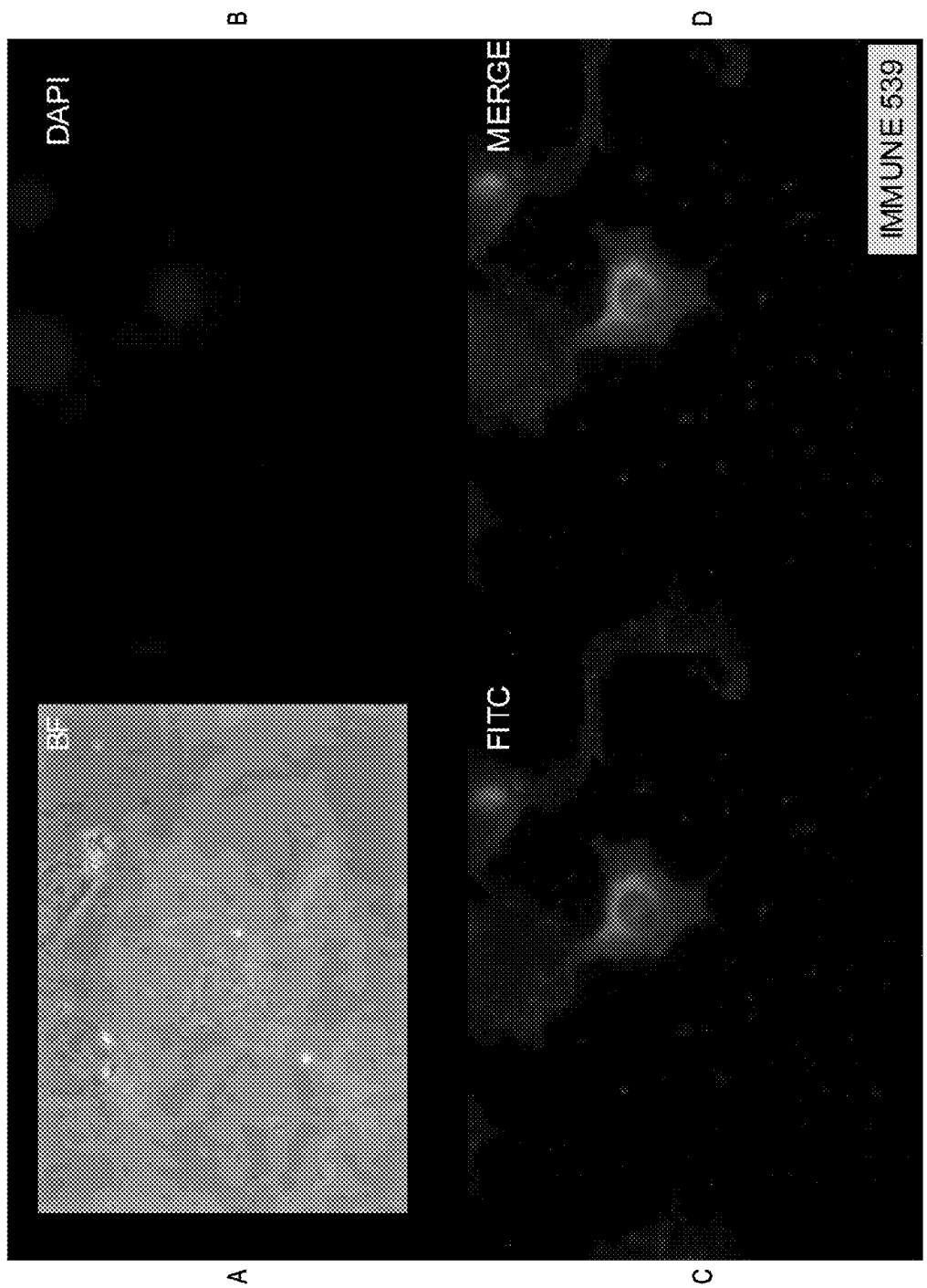
FIG. 19, comprising micrographs A-D, provides the BF (A), DAPI (B), FITC (C) and Merged (D) images for the immune staining of MMMT 539.

Next, the expression of SAS1R in MMMT 308 and MMMT 539 cell lines was studied using indirect immunofluorescence. The first figure, FIG. 17, provides the control (pre-immune) results of expression of SAS1R in MMMT 308 and MMMT 539 cell lines using indirect immunofluorescence (panels A-D; upper-308; lower-539; A and C— phase contrast; B and D—pre-immune). FIG. 18 provides the BF (A), DAPI (B), FITC (C) and Merged (D) images for the immune staining of MMMT 308. FIG. 19 provides the BF (A), DAPI (B), FITC (C) and Merged (D) images for the immune staining of MMMT 539. FIG. 20 provides the Actin (A), DAPI (B), FITC (C) and Merged (D) images for the immune staining of MMMT 539.

The present results demonstrate that, in addition to its restricted expression and localization within the ooplasm, the SAS1R protein appears in humans in tumors of the uterus, including malignant mixed Mullerian tumors and endometrial carcinomas.

A series of tumor samples were obtained and examined for SAS1R expression. It was found that the incidence of SAS1R protein in MMMT punch biopsy samples was 86% (expressed in 12 of 14 mMMT tumors) and 66% (expressed in 14 of 21) in endometrial carcinomas. Review of the micrographs and microscopic observation demonstrated strong cytoplasmic staining of the mesenchymal differentiated tumor cells and cytoplasmic staining of both glandular and mesenchymal cells of the tumor.

SAS1R in Lung Cancer and Bladder Cancer

Figure 21:
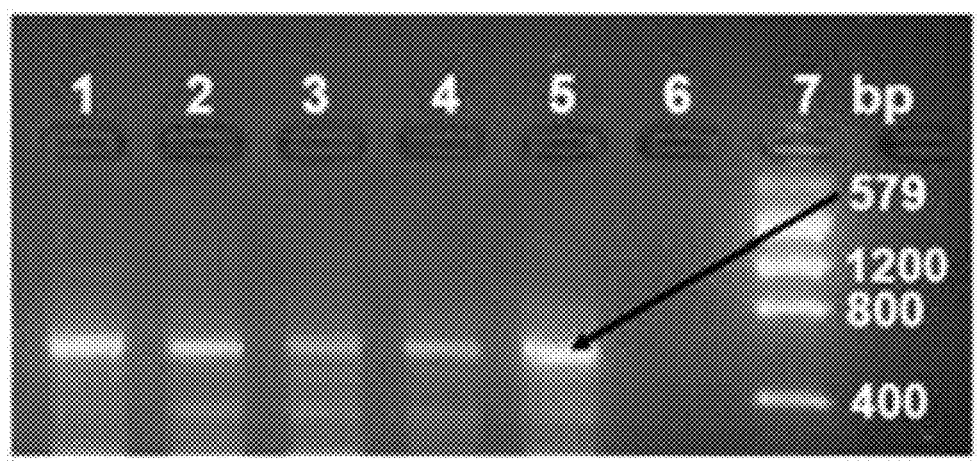
FIG. 21 demonstrates the results of an electrophoretic analysis of SAS1R gene expression in human cancer cells and controls. The catalytic domain product of 579 bp. The blot represents PCR amplification of the human SAS1R catalytic domain of 579 bp in lung cancer cell lines NCI-H226 (Ln-1) and A549 (Ln-2), HEK-293 (Ln-3), human ovary (Ln-4), MMMT 539 (Ln-5), control water (Ln-6), and the standards ladder is shown in Ln-7.
Figure 22:
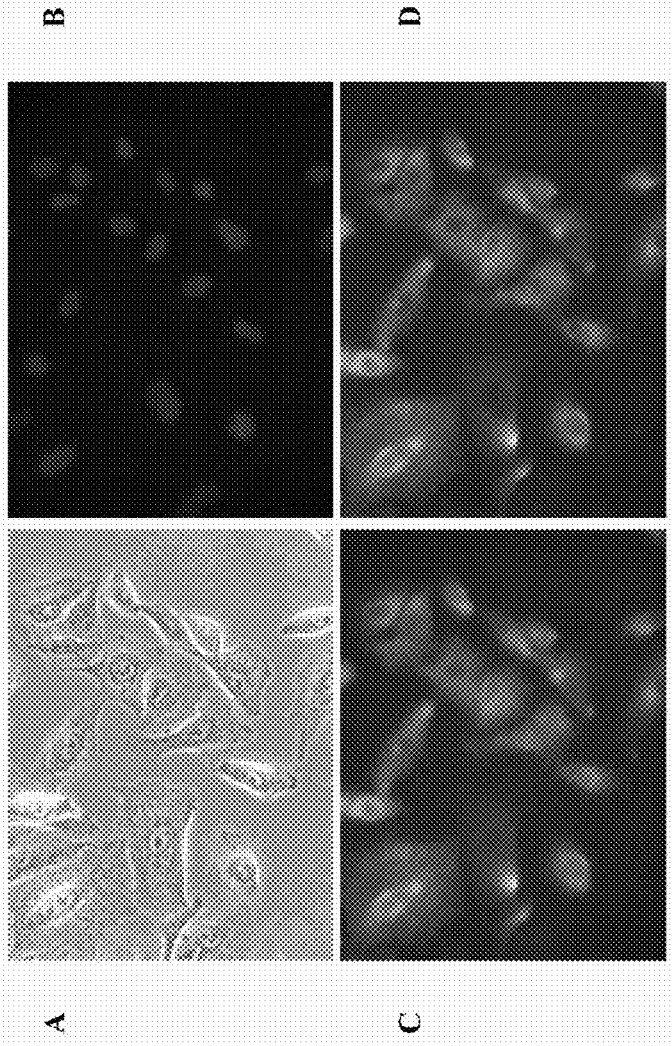
FIG. 22, comprising images of four micrographs (A-D), represents the results of SAS1R localization in fixed unpermeabilized human lung adenocarcinoma cell line A549 cells in culture probed with the immune antibody. Upper left—phase contrast; Upper right—DAPI (nuclear) only; Lower left—DAPI and SAS1R; Lower right—SAS1R only FIG. 23, comprising images of three micrographs (A-C) represents the results of SAS1R localization studies in fixed unpermeabilized human lung adenocarcinoma cell line A549 cells probed with the preimmune antibody. A—phase contrast; B—DAPI (blue in the color photograph); SAS1R—(green in the color photograph)
Figure 23:
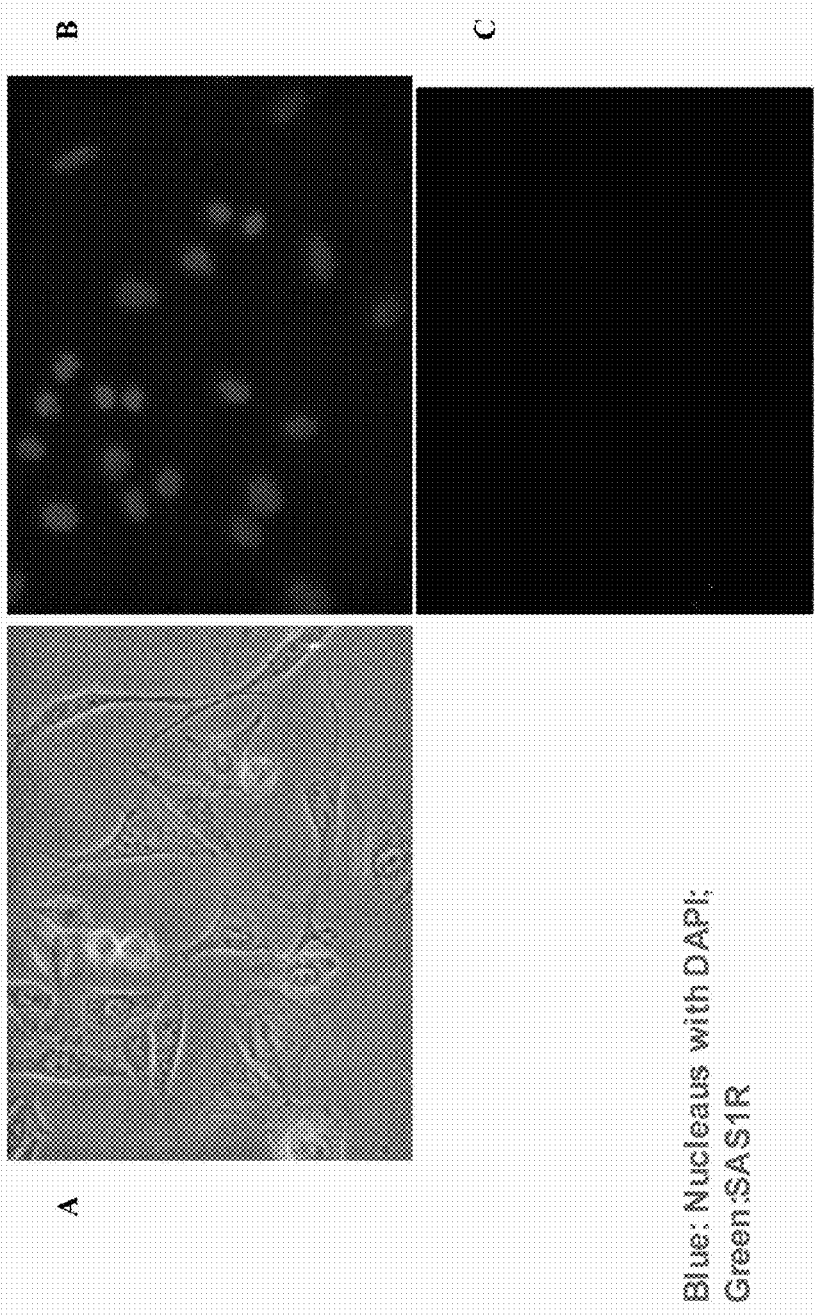
FIG. 23C represents a negative control.

A series of experiments were performed to determine if other cancer also expressed SAS1R. Lung and bladder cancer cell lines and tumor samples were used. Several experiments were performed and they confirmed SAS1R expression in several squamous and adenocarcinoma lung cancer cell lines. Some cell lines were also stained in culture for SAS1R protein and some were tested for gene expression of SAS1R by isolating full length SAS1R cDNA and amplifying it. Lung tumor samples were also used for SAS1R cDNA isolation and amplification. Human lung cancer cell lines included A549 and NCI-H226. Bladder cancer cell lines included human UMUC3. SAS1R was identified in lung cancers and cell lines and also found to be expressed at the surface of the two lung cancer cell lines tested. Controls included HEK293 human embryonic kidney cells, normal lung, human ovary, water, and the MMMT 539 uterine cancer as a positive control. These data demonstrate that SAS1R can be a useful marker for lung cancer (FIG. 21) and bladder cancer (data not shown) and that its surface location makes it an easy target for diagnosis and therapy. FIG. 21 demonstrates the results of an electrophoretic analysis of SAS1R gene expression in human lung cancer cells and the controls described above. The figure demonstrates the catalytic domain product of 579 bp. FIG. 22, comprising images of four micrographs (A-D), represents the results of SAS1R localization in fixed unpermeabilized human lung adenocarcinoma cell line A549 cells in culture probed with the immune antibody. FIG. 23, comprising images of three micrographs (A-C) represents the results of SAS1R localization studies in fixed unpermeabilized human lung adenocarcinoma cell line A549 cells probed with the preimmune antibody. FIG. 23C represents a negative control.

Figure 37:
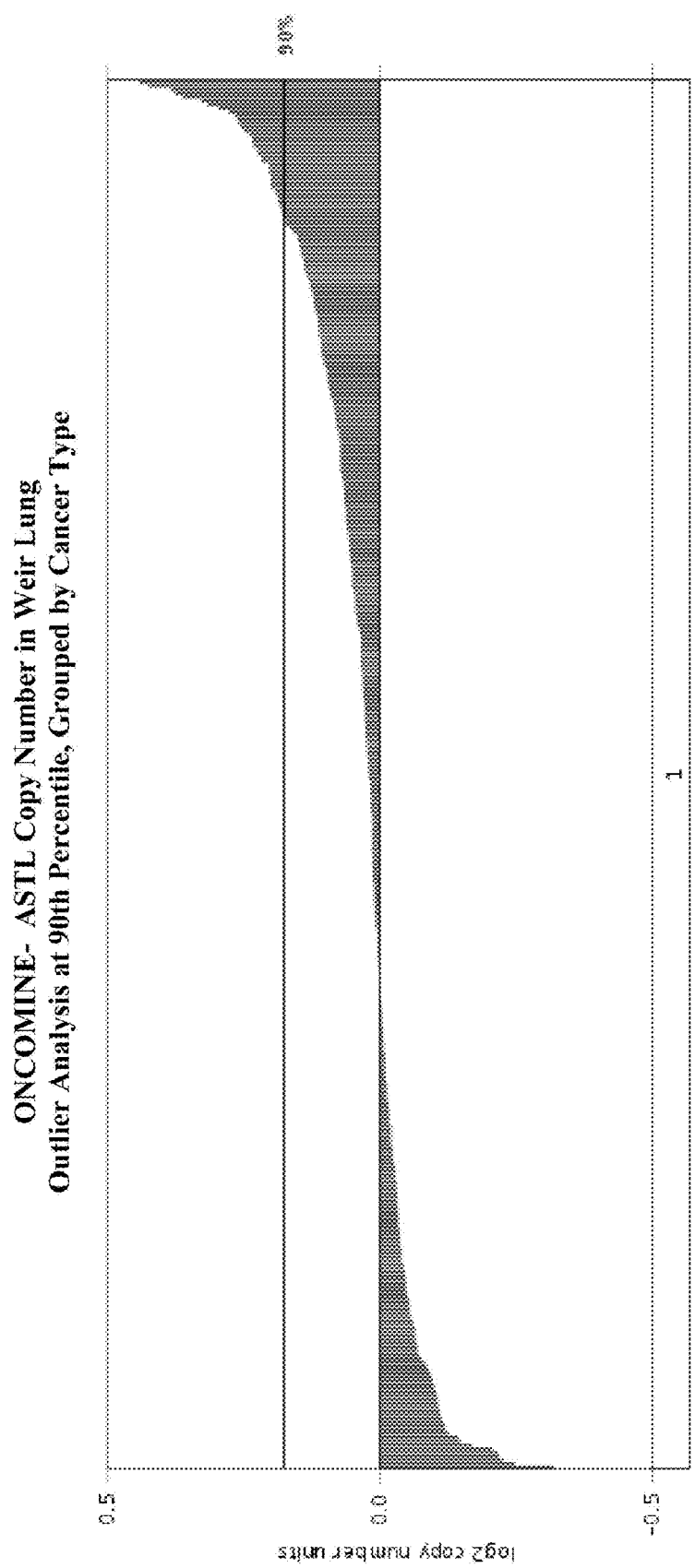
FIG. 37 is a graphic representation of an analysis of ASTL (the gene encoding SAS1R) gene copy number in Weir Lung. Weir, et al. (2007, Nature, 450, 893-898) deposited the gene chip array datasets. These datasets were then interrogated herein for ASTL using Oncomine. The analysis is an outlier analysis at the 90th percentile, grouped by cancer type. The ordinate represents log 2 copy number units. Data represent 371 lung adenocarcinomas. DNA—18,823 measured genes; RefSeq Genes—UCSC refGene, July 2009, hg18, NCBI 36.1, March 2006; Copy Number Gene Rank—1389 (in top 8%); COPA—3.154; Reporter—02-096160608.

SAS1R (ASTL) was also analyzed by Oncomine and its expression was found to be upregulated in 371 lung adenocarcinomas (FIG. 37), which places SAS1R with a gain copy number ranking of 1389, which places it in the top 8% of genes upregulated in lung adenocarcinomas. These data from primary tumors is supported by upregulation of SAS1R in lung adenosquamous and adenocarcinoma cells lines. The analysis was based datasets prepared by Weir, et al. (2007, Nature, 450, 893-898), who had deposited the gene chip array datasets. These datasets were then interrogated herein for ASTL using Oncomine. The analysis is an outlier analysis at the 90th percentile, grouped by cancer type. The ordinate represents log 2 copy number units. Data represent 371 lung adenocarcinomas. DNA-18,823 measured genes; RefSeq Genes—UCSC refGene, July 2009, hg18, NCBI 36.1, March 2006); Copy Number Gene Rank-1389 (in top 8%); COPA-3.154; Reporter-02-096160608.

Analysis of other cancers described herein for ASTL copy number (the gene encoding SAS1R) demonstrated increased copy numbers as well (not shown).

Figure 34:
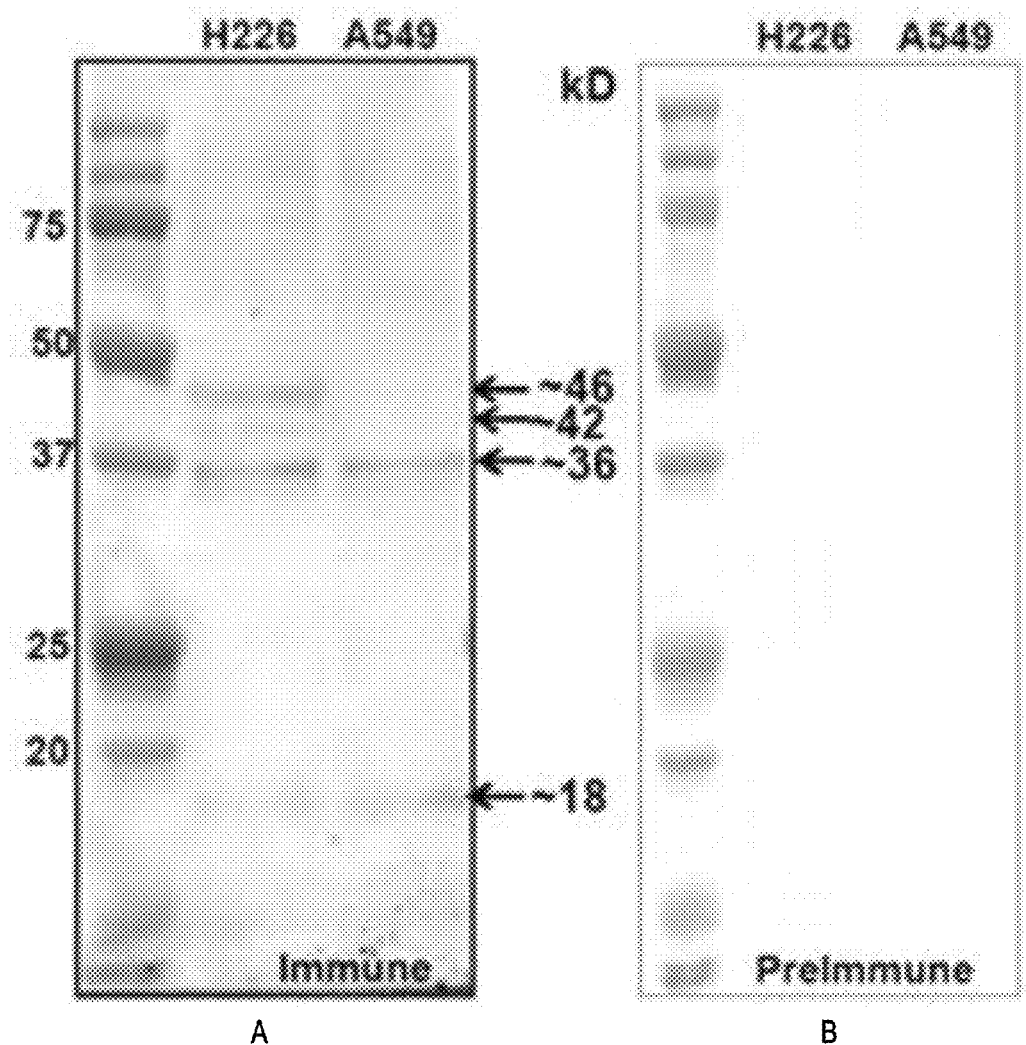
FIG. 34, comprising left (A) and right (B) panels, provides images of Western blotting of protein extracts from lung cancer H226 and A549 cell lines using a guinea pig polyclonal anti-human SAS1R antibody. They show expression of full length (46 kD) and truncated SAS1R proteins in both lung cancer cell lines H226 and A549.

Western blotting (FIG. 34) of protein extracts from lung cancer H226 and A549 cell lines using a guinea pig polyclonal anti-human ovastacin antibody showed expression of full length (46 kD) and truncated ovastacin proteins in both lung cancer cell lines H226 and A549.

Staining of cells in culture was also performed to localize SAS1R. Most importantly, as shown with other cells herein and in the ovary, SAS1R can be localized to the surfaces of both H226 and A549 cells (not shown).

SAS1R expression in Ovarian Tumors—

Figure 24:
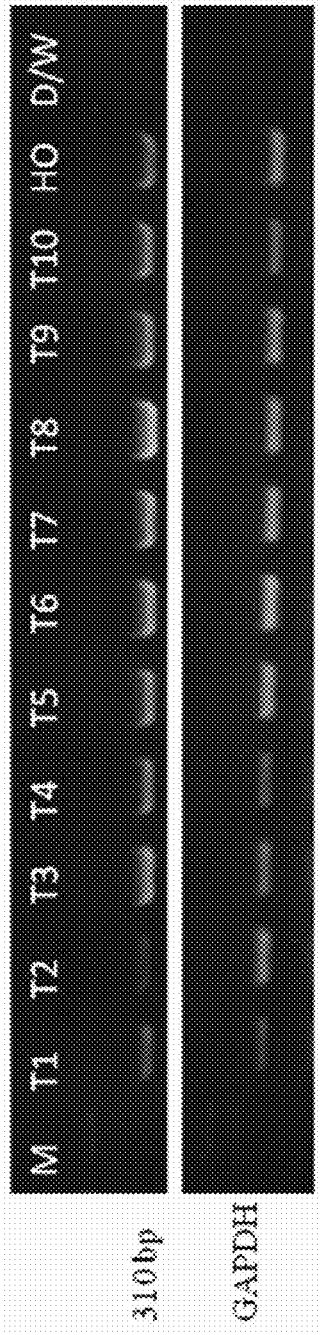
FIG. 24 is an image of an electrophoretic analysis of SAS1R expression using C-term specific primers amplifying a 310 bp product (upper panel). Ten ovarian tumors (lane identification—T1-T10) were analyzed and all expressed SAS1R. The normal ovarian tissue sample control (HO) also demonstrated the presence of SAS1R transcripts. The upper panel represents the 310 bp product and the lower panel the GAPDH control.

As described, SAS1R was known to be expressed in normal ovary tissue, and in fact, ovary is the only tissue where SAS1R protein expression has been found to be detectable under normal conditions. Because of this, it was decided to examine ovarian tumors for SAS1R expression. FIG. 24 is an image of an electrophoretic analysis of SAS1R expression using C-term specific primers amplifying a 310 bp product. Ten ovarian tumors (T1-T10) were analyzed and all expressed SAS1R. The normal ovarian tissue sample control (HO) also demonstrated the presence of SAS1R transcripts. The upper panel represents the 310 bp product and the lower panel the GAPDH control.

SAS1R Expression in Uterine Tumors—

Figure 25:
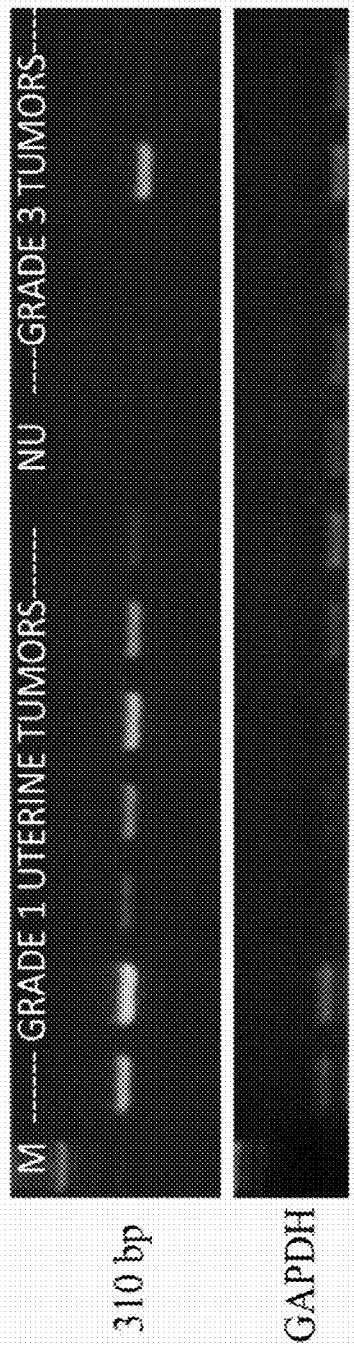
FIG. 25 provides images (upper and lower panels) of the electrophoretic analysis of SAS1R expression in uterine tumors and normal uterus. C-term specific primers amplifying a 310 bp product was used to detect expression. The upper panel represents the 310 product and the lower panel is the GAPDH control. NU—Normal uterine sample. SAS1R transcripts were detected in seven of seven (7/7) Grade 1 uterine tumors. SAS1R transcripts were detected in one of four (1/4) Grade 3 uterine tumors. SAS1R transcripts were not detectable in normal uterine tissue.

As a follow up to the experiments described above, the 310 bp product of SAS1R was also examined in normal human uterine tissue and in human uterine tumors. FIG. 25 provides images (upper and lower panels) of the electrophoretic analysis of SAS1R expression in uterine tumors and normal uterus. C-term specific primers amplifying a 310 bp product was used to detect expression. The upper panel represents the 310 product and the lower panel is the GAPDH control. NU—Normal uterine sample. SAS1R transcripts were detected in seven of seven (7/7) Grade 1 uterine tumors. SAS1R transcripts were detected in one of four (1/4) Grade 3 uterine tumors. SAS1R transcripts were not detectable in normal uterine tissue.

SAS1R Expression in MMMT Cells—

Figure 26:
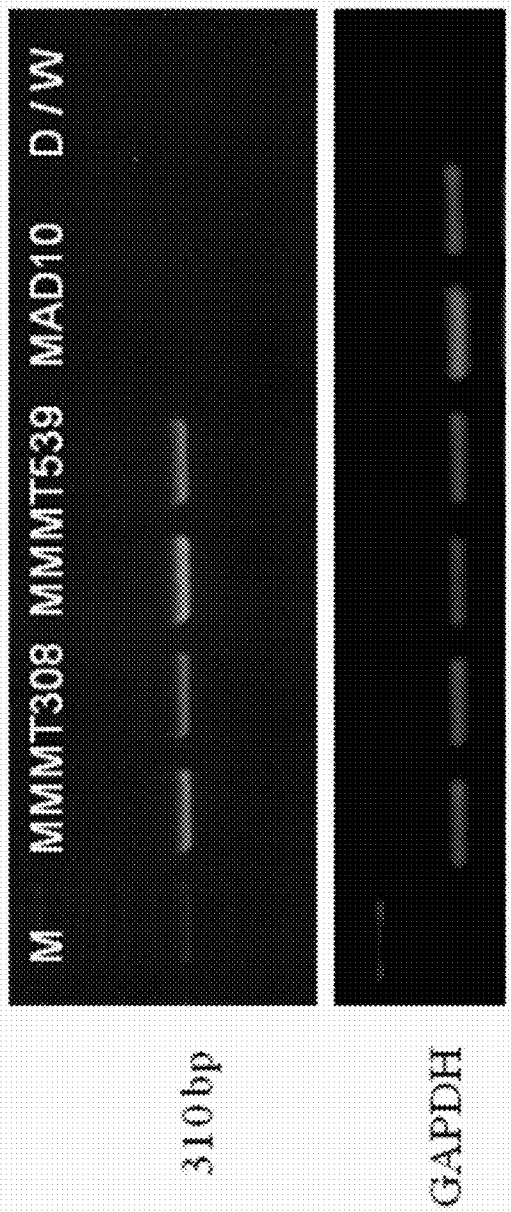
FIG. 26 provides images of the electrophoretic analysis of detection of the 310 bp SAS1R product for MMMT 308 and MMMT 539 cancer cell lines compared to the control endometrial cell line (MAD10), confirming the SAS1R gene sequence with 99% identity and verifying the results described above for the MMMT cancer cell lines. The upper panel indicates the 310 bp SAS1R product and the lower panel represents the GAPDH control.

FIG. 26 provides images of the electrophoretic analysis of detection of the 310 bp SAS1R product for MMMT308 and MMMT539 cancer cell lines compared to the control endometrial cell line (MAD10), confirming the SAS1R gene sequence with 99% identity and verifying the results described above for the MMMT cancer cell lines. The upper panel indicates the 310 bp SAS1R product and the lower panel represents the GAPDH control.

Figure 27:
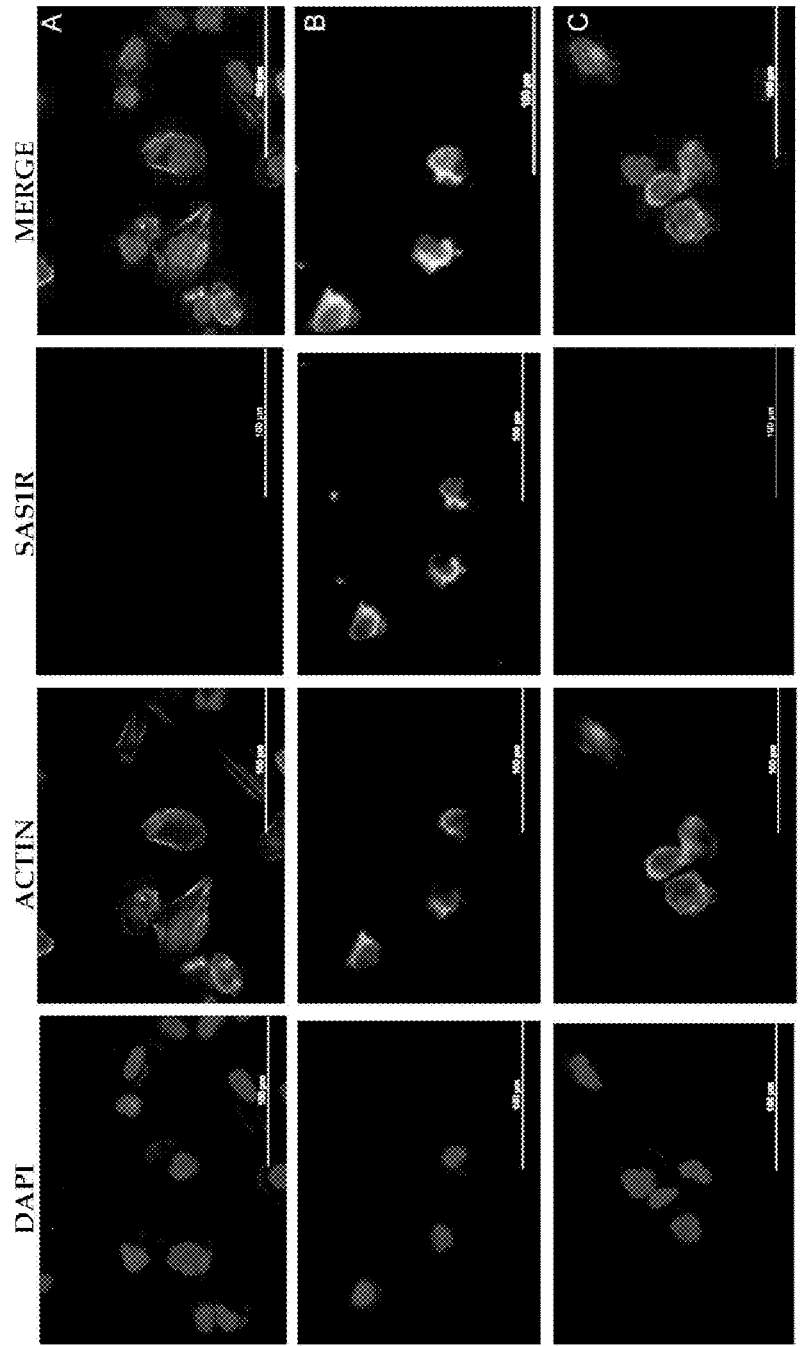
FIG. 27, comprising FIGS. 27A to 27F (four panels each), represents images of live cell staining with a rabbit polyclonal antibody directed against SAS1R which demonstrate cell surface localization of SAS1R in MMT tumor cells. Panels 27 A, C, and E have been stained with preimmune sera. Panels B, D and F are stained with immune sera to SAS1R. The four rows, left to right, for FIGS. 27A to 27F represent DAPI staining, staining for Actin, SAS1R staining, and MERGE. Cell nuclei were counterstained with DAPI. Phalloidin (red stain) was used to localize cytoskeletal actin protein. No immunostaining is seen when cell lines MMMT 539 (Panel A), MMMT 308 (Panel C) and control endometrial cell line MAD10 (Panel E) were stained with pre-immune sera. However, a distinct cell surface localization was observed with MMMT 539 (Panel B) and MMMT 308 (Panel D) with the post immune sera. No immunostaining was observed with control endometrial cell line MAD10 (Panel F) with the post immune sera. Similar results have been obtained using live staining of lung cancer cell lines (not shown here).

Next, a series of experiments were performed to examine in vitro live MMMT cancer cell lines for SAS1R expression using staining techniques. FIG. 27, comprising FIGS. 27A to 27F (four panels each), represents images of live cell staining with a rabbit polyclonal antibody directed against SAS1R which demonstrate cell surface localization of SAS1R. Panels 27 A, C, and E have been stained with preimmune sera. Panels B, D and F are stained with immune sera to SAS1R. The four rows, left to right, for FIGS. 27A to 27F represent DAPI staining, staining for Actin, SAS1R staining, and MERGE. Cell nuclei were counterstained with DAPI. Phalloidin (red stain) was used to localize cytoskeletal actin protein. No immunostaining is seen when cell lines MMMT 539 (Panel A), MMMT 308 (Panel C) and control endometrial cell line MAD10 (Panel E) were stained with pre-immune sera. However, a distinct cell surface localization was observed with MMMT 539 (Panel B) and MMMT 308 (Panel D) with the post immune sera. No immunostaining was observed with control endometrial cell line MAD10 (Panel F) with the post immune sera.

Figure 28:
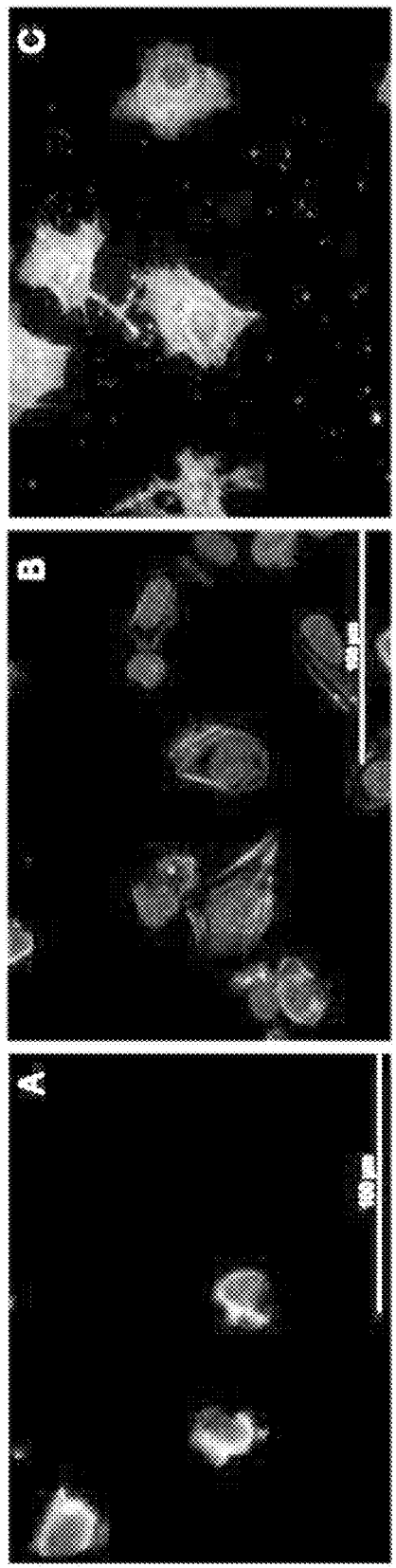
FIG. 28, comprising panels A, B, and C, represents images of three micrographs depicting the results of live staining of MMMT cells in culture for SAS1R, demonstrating not only cell surface expression, but also a change in cell shape. Panel A demonstrates (green in the color figure) cell surface localization of SAS1R using rabbit polyclonal antisera. No staining was observed with pre-immune sera and there was no apparent change in cell shape and actin cytoskeleton distribution (Panel B). When first fixed with paraformaldehyde and then immunostained with immune sera, cells showed cytoplasmic distribution of SAS1R, with concentration of SAS1R at the perinuclear region. It should be noted in the same panel, that cell maintain their polygonal shape and there is no change in the actin cytoskeleton distribution (Panel C).

An unexpected phenomenon was observed in live cells exposed to an anti-SAS1R antibody, namely an alteration in cell shape. FIG. 28, comprising panels A, B, and C, represents images of three micrographs depicting the results of live staining of MMMT cells in culture for SAS1R, demonstrating not only cell surface expression, but also a change in cell shape. Panel A demonstrates (green in the color figure) cell surface localization of SAS1R using rabbit polyclonal antisera. In live cell staining, addition of the immune sera caused a change in cell shape, seen as rounding and actin cytoskeleton redistribution (red in the color photograph). No staining was observed with pre-immune sera and there was no apparent change in cell shape and actin cytoskeleton distribution (Panel B). When first fixed with paraformaldehyde and then immunostained with immune sera, cells showed cytoplasmic distribution of SAS1R, with concentration of SAS1R at the perinuclear region. It should be noted in the same panel, that cell maintain their polygonal shape and there is no change in the actin cytoskeleton distribution (Panel C).

Anti-SAS1R Antibody Killing of Cancer Cells

Figure 29:
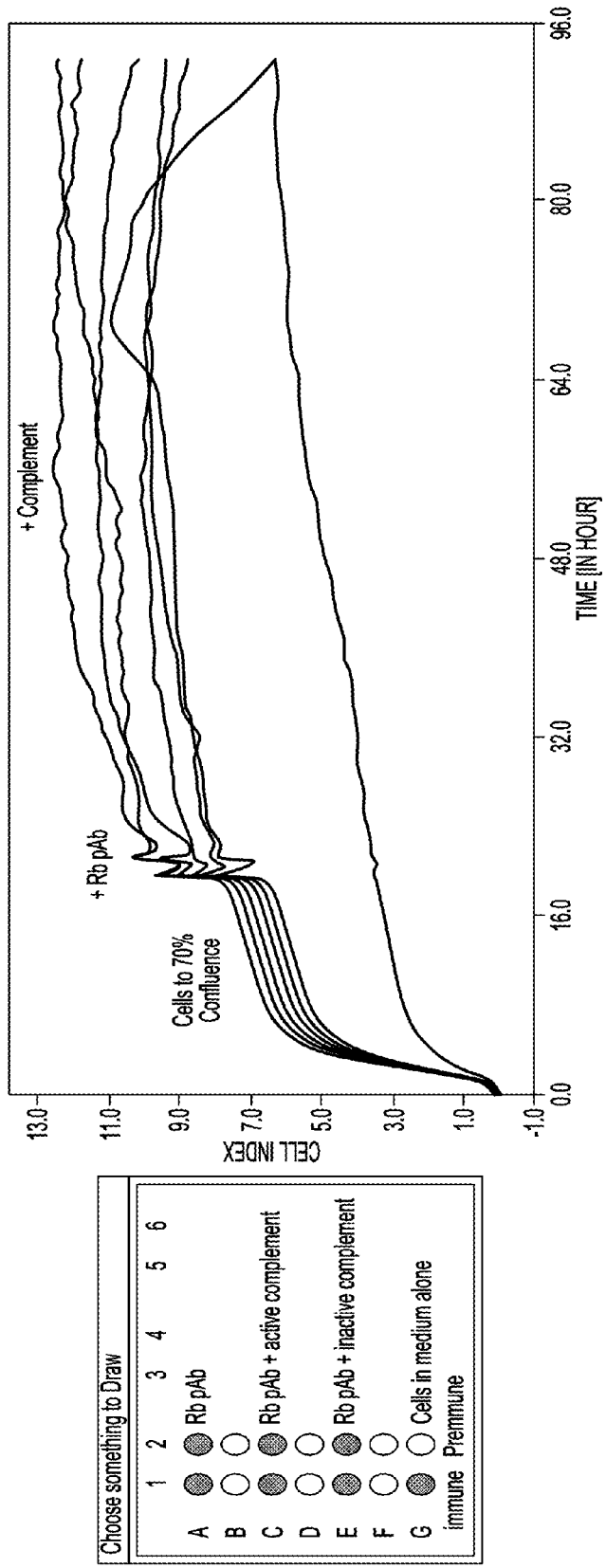
FIG. 29 is a graphic representation of the results of experiments determining whether an anti-SAS1R antibody could be used to induce cell death of cancer cells. MMMT 539 cells at 70% confluency were incubated with heat inactivated immune and preimmune rabbit polyclonal antibodies overnight and then exposed to exogenous inactive or active complement proteins. The ordinate represents cell index, a measure of death and/or apoptosis. The abscissa represents time in hours. Rb—rabbit; Rb pAb—rabbit polyclonal antibody. A control group (orange line on the color graph) represented cell in medium alone.

Without wishing to be bound by any particular theory, it was hypothesized herein, that based on the results described above, the possibility existed that an anti-SAS1R antibody might be useful for killing cells expressing SAS1R, particularly since it is shown herein that SAS1R is found on the cell surface. Experiments were performed on the MMMT 539 cancer cell line to determine if they were susceptible to SAS1R antibody-mediated complement-dependent cell death if exposed to the antibody and complement. MMMT 539 cells at 70% confluency were incubated with heat inactivated immune and preimmune rabbit polyclonal antibodies overnight and then exposed to exogenous inactive or active complement proteins. The results of the experiments are depicted in the graph of FIG. 29. It can be seen in the graph of FIG. 29, that at 72 hours, the line representing the cells exposed to immune rabbit polyclonal sera against SAS1R and active complement had peaked and began to decline. This indicates antibody mediated cell death and apoptosis. There was no change in peak pattern in the other groups. Rb—rabbit; Rb pAb-rabbit polyclonal antibody. A control group (orange line on the color graph) represented cell in medium alone.

Figure 30:
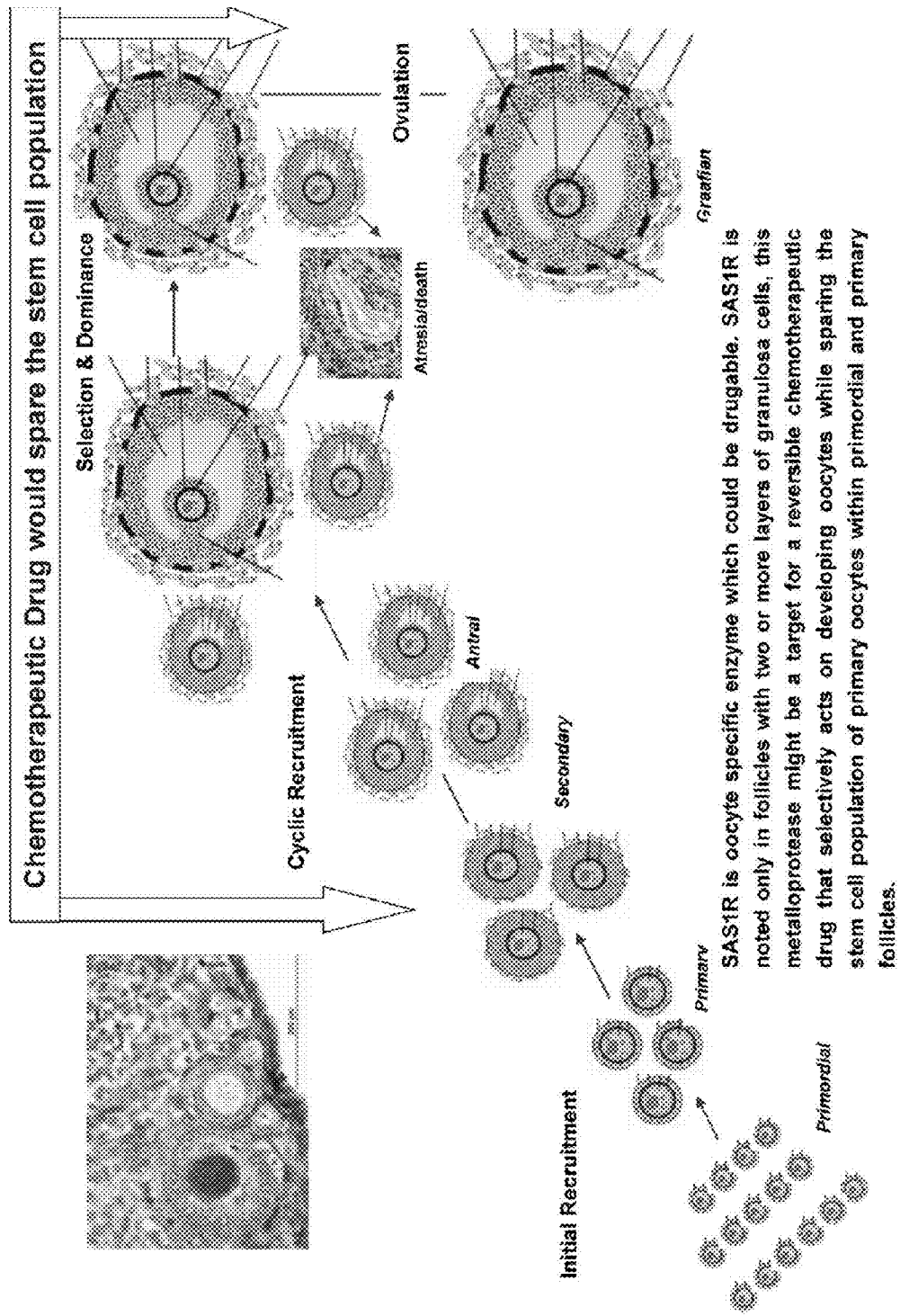
FIG. 30 is a schematic representation illustrating that SAS1R is an oocyte specific enzyme which could be drugable for chemotherapy but spare ovarian stem cells.

Lack of Effect of SAS1R-Targeted Chemotherapy or Immunotherapy on Ovarian Stem Cells As described herein, although SAS1R is expressed in the ovary (the only normal tissue in which it is expressed), therapy of cancers which targets cancer should not impact a woman's ability to have children. FIG. 30 is a schematic representation illustrating that SAS1R is an oocyte specific enzyme which could be drugable. SAS1R is noted only in follicles with two or more layers of granulosa cells, this metalloprotease might be a target for a reversible chemotherapeutic drug that selectively acts on developing oocytes while sparing the stem cell population of primary oocytes within primordial and primary follicles.

Further support for the hypothesis and proposed therapies regimens described and claimed herein is a study performed on ovarian cancer stem cells described below.

SAS1R Expression and Ovarian Cancer Stem Cells

Figure 31:
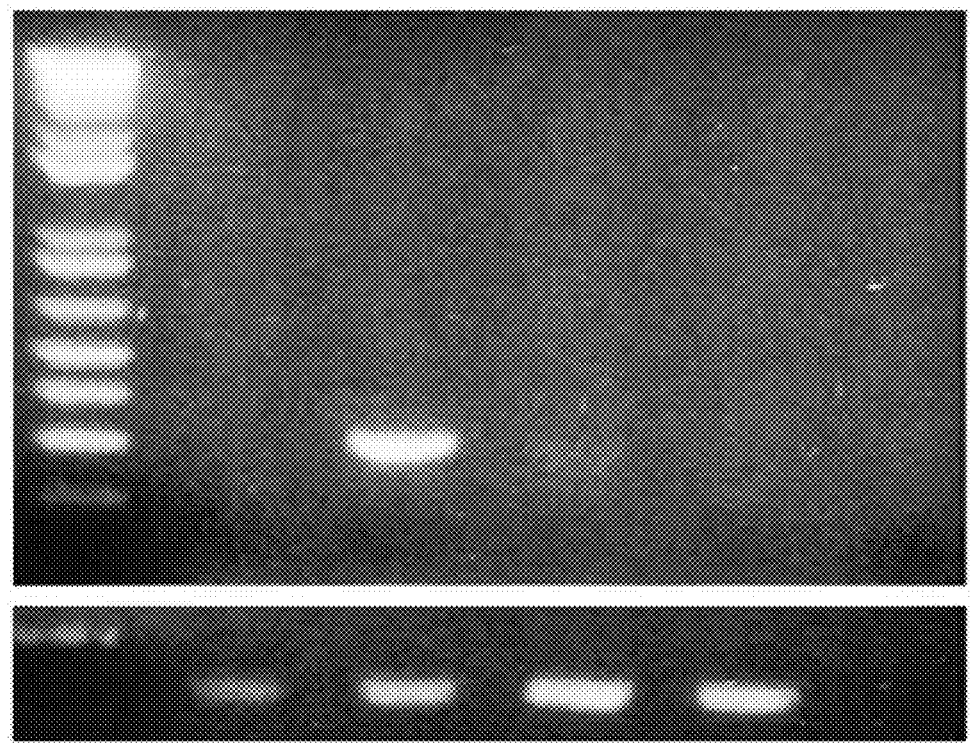
FIG. 31 represents the electrophoretic results of SAS1R expression in ovarian cancer stem cells. R182 is a clone of the human ovarian stem cell population and M/S/T182 are differentiated cell lines of R182. Only lane R182 shows the expected SAS1R amplimer indicating that the other three cell populations have probably lost the property of stemness. Human GAPDH was used to serve as a loading control. D/W is water control to check for primer specificity.

As described above, SAS1R was found to be expressed in all ovarian cancers tested and in a high percentage of other cancers tested. To better determine the role of SAS1R as a diagnostic biomarker for cancer and to understand its function in normal and cancer cells, ovarian cancer stem cells were utilized (Alvero et al., Stem Cells, 2009, 27:2405-2413). These cells can be studied in an undifferentiated and in a differentiated state. To that end, SAS1R expression was examined in both the undifferentiated ovarian cancer stem cell line and in differentiated cells derived from the stem cell line. C-term specific primers were used to amplify hSAS1R from four cDNA preps of ovarian cancer stem cell lines. R182 is a clone of the human ovarian stem cell population and M/S/T182 are differentiated cell lines of R182. Only lane R182 shows the expected SAS1R amplimer indicating that the other three cell populations have probably lost the property of sternness (FIG. 31). This suggests that hSAS1R gene is present in ovarian cancer stem cell populations but not in differentiated cells. Human GAPDH was used to serve as a loading control. D/W is water control to check for primer specificity.

Human SAS1R can be Detected in Human Serum—

Useful assays for diagnosing cancers include those in which biomarkers can be measured in blood, serum, plasma, or other fluids. To that end, commercially available normal serum was spiked with truncated full length human recombinant hSAS1R protein in varying concentrations (nanogram levels). Various techniques are useful for such assays, and two are described here. Others techniques such as enhanced chemiluminescence and terbium release can be used as well.

Human serum was spiked with various concentrations of recombinant human SAS1R, ranging from 0 ng/ml (control) to 200 ng/ml. Rabbit polyclonal antibodies (preimmune and immune) were used to detect the presence of the protein by Western blot analysis and by ELISA.

Figure 32:
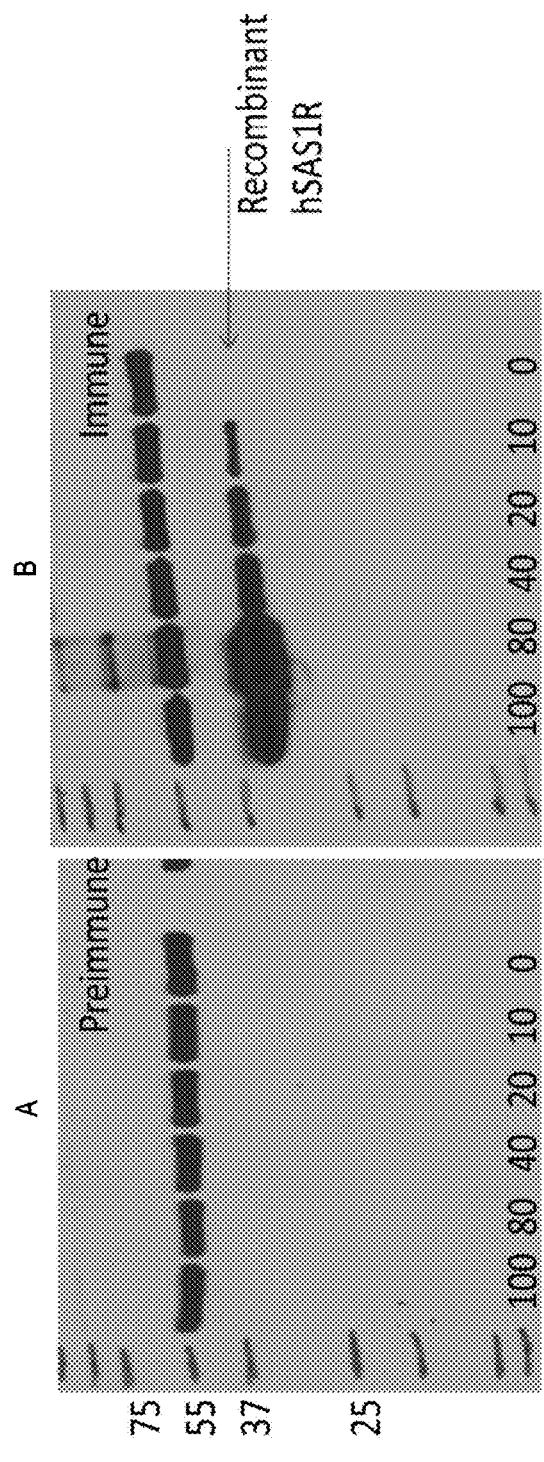
FIG. 32, comprising images 32A, and 32B, represents images of a Western blot analysis detecting human SAS1R in serum. Human serum was spiked with various concentrations of recombinant human SAS1R, ranging from 0 ng/ml (control) to 100 ng/ml. Rabbit polyclonal antibodies (preimmune—FIG. 32A; and immune—FIG. 32B) were used to detect the presence of the protein by Western blot analysis and by ELISA. Molecular weight standards are provided in the left lane of each blot. Specific immunostaining of the immune sera (FIG. 32B) at 36 kDa is present and even at the lowest concentration tested (10 ng/ml) a signal was detected. No signal was detected in the control lane where no SAS1R was added (preimmune—FIG. 32A).

As seen in the Western blot analysis (FIG. 32), specific immunostaining of the immune sera (FIG. 32B) at 36 kDa is present and even at the lowest concentration tested (10 ng/ml) a signal was detected. No signal was detected in the control blot (preimmune-FIG. 32A) and no signal was detected in the serum where no SAS1R was added (FIG. 32B-indicated by "0"). This demonstrates that normal serum has no detectable levels of SAS1R under these conditions. Such blots can be scanned and digitized and levels compared by standard software (left blot—preimmune; right blot—immune).

Figure 33:
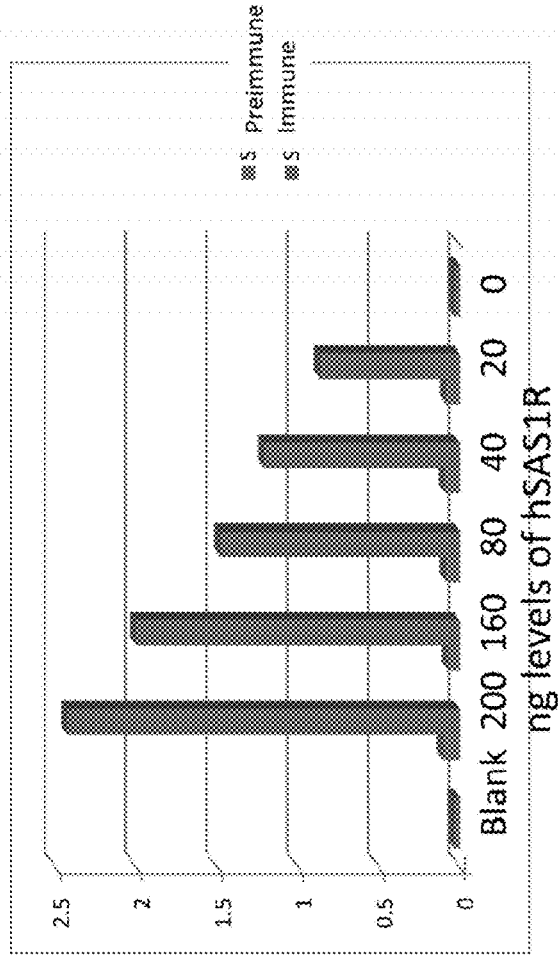
FIG. 33 graphically illustrates the results of an ELISA assay detecting and measuring human SAS1R levels in human serum. Human serum was spiked with various concentrations of recombinant human SAS1R, ranging from 0 ng/ml (control) to 200 ng/ml. A linear relationship can be seen for the signal in all the ranges tested (20-200 ng/ml) and the positive signal to background ratio (immune to preimmune) is quite high even in the lowest level of SAS1R used (20 ng/ml). Absorbance was at 605 nm. The groups, right to left, include Blank, 200 ng/ml SAS1R, 160 ng/ml SAS1R, 80 ng/ml SAS1R, 40 ng/ml SAS1R, 20 ng/ml SAS1R, and 0 ng/ml SAS1R. The left bar of each group represents "Preimmune" and the right bar of each group represents "Immune".

An ELISA analysis was used to demonstrate the same experimental hypothesis as seen in the Western blot analysis. A linear relationship can be seen for the signal in all the ranges tested (20-200 ng/ml) and the positive signal to background ratio (immune to preimmune) is quite high even in the lowest level of SAS1R used (FIG. 33). Absorbance was at 605 nm. These experiments demonstrate that nanogram levels of this protein can be easily detected and measured in sera of individuals and suggest that picogram quantities are detectable. It also demonstrates that normal serum has no detectable SAS1R. Furthermore, other antibodies against SAS1R are described herein, including human and guinea pig monoclonals.

Monoclonal Antibodies Directed Against SAS1R—

Monoclonal antibodies have multiple uses, including use for therapy. To that end, five additional monoclonal were made and tested.

Figure 35:
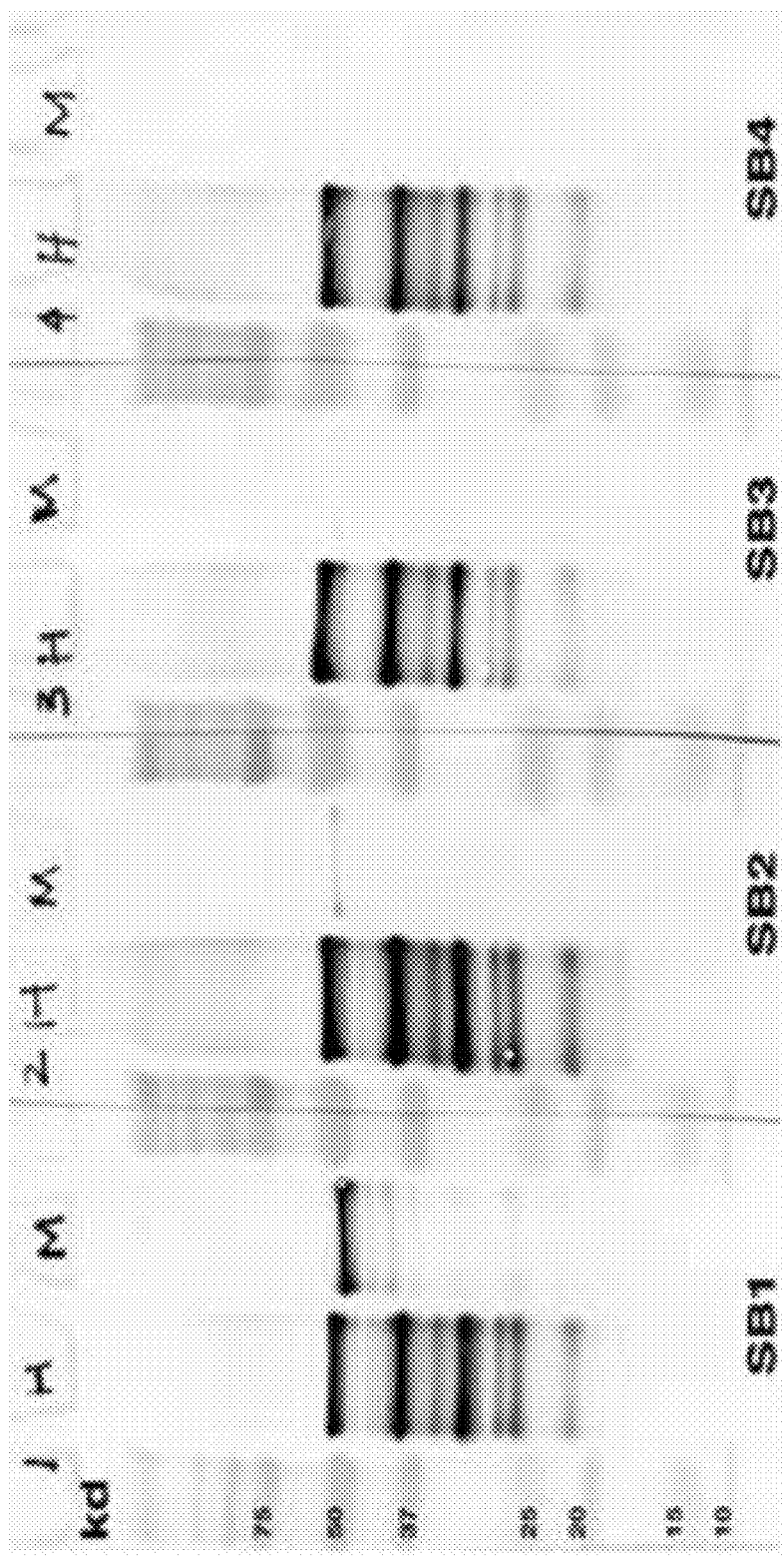
FIG. 35, comprising panels A-D, provides images of a Western blot analysis of the reactivity of mouse monoclonal antibodies made against human SAS1R with either human or mouse SAS1R. Five murine monoclonal antibodies (SB1, SB2, SB3, SB4, and SB5) were raised against recombinant human SAS1R. Four are shown in this figure: SB1 (left/first panel; A); SB2—second panel (B); SB3—third panel (C); SB4—fourth panel (D). The monoclonal antibodies were tested for their activity against human (H) and mouse (M) SAS1R. Molecular weight standards are provided as well. Western blot analyses demonstrated that mAbs SB1 and SB2 recognized both human and mouse SAS1R, while mAbs SB3, SB4, and SB5 react only with human SAS1R. Note that in the blots purified recombinant human SAS1R showed multiple peptides due to autoproteolysis.
Figure 36:
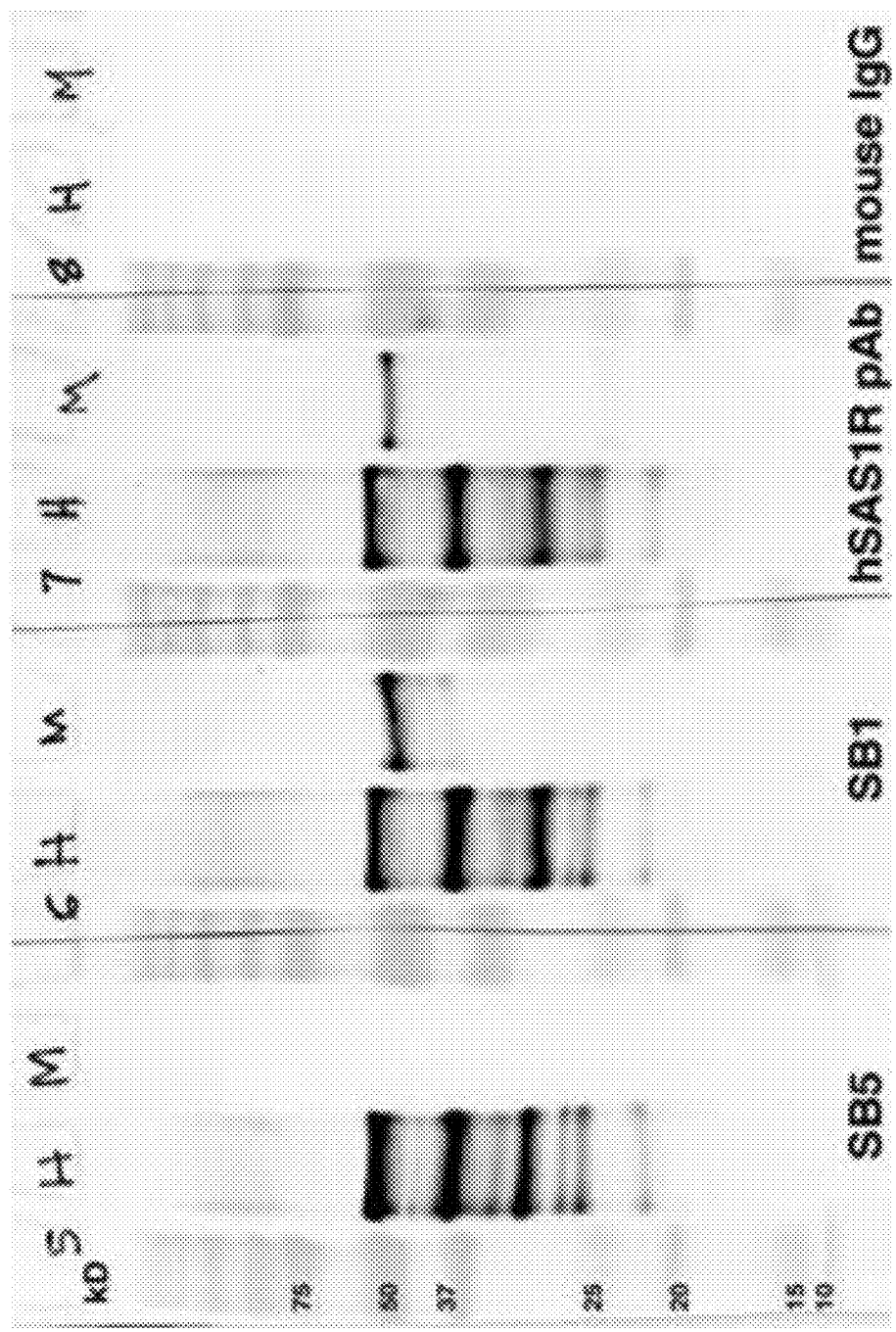
FIG. 36, comprising panels A-D, provides images of a Western blot analysis of the reactivity of mouse monoclonal antibodies made against human SAS1R with either human or mouse SAS1R. Five murine monoclonal antibodies (SB1, SB2, SB3, SB4, and SB5) were raised against recombinant human SAS1R. SB5 (left/first panel; A); SB1—second panel (B); hSASIR polyclonal antibody—third panel (C); Mouse IgG control—fourth panel (D). They were tested for their activity against human (H) and mouse (M) SAS1R. Molecular weight standards are provided. Western blot analyses demonstrated that mAbs SB1 and SB2 recognized both human and mouse SAS1R, while mAbs SB3, SB4, and SB5 react only with human SAS1R.

Five murine monoclonal antibodies (SB1, SB2, SB3, SB4, and SB5) were raised against recombinant human SAS1R. They were tested for their activity against human (H) and mouse (M) SAS1R (FIGS. 35 and 36). Western blot analyses demonstrated that mAbs SB1 and SB2 recognized both human and mouse SAS1R, while mAbs SB3, SB4, and SB5 react only with human SAS1R. Note that in the blots purified recombinant human SAS1R showed multiple peptides due to autoproteolysis. These murine monoclonals to human SAS1R will be coupled with drugs and radionuclides and employed as biological probes in the proposed translational experiments. In one aspect, the monoclonals can be modified, including humanized.

Future Experiments—

These experiments will include using SAS1R as a target in assays to identify drugs, compounds, or other agents that will inhibit SAS1R or be useful in cancer therapy. These assays can be performed with libraries as high throughput screening or with individual agents. New drugs can also be made which target SAS1R expression, levels, and activity. Peptide libraries can be generated and used to determine if peptidomimetics can be found to regulate SAS1R. A Knockout mouse will be prepared by targeted deletion of the SAS1R gene.

Summary—

SAS1R, previously found to be expressed in the ovary, was unexpectedly found in the present studies to be expressed in multiple tumor types and in high percentages of the tumors. SAS1R was found herein to be expressed at the mRNA level and at the protein level, including at the cell surface. By identifying a novel tumor surface protein that is restricted to the egg among normal tissues, the present application encompasses an invention offering a breakthrough in cancer diagnosis, therapeutics, and treatment. Cancer-oocyte biomarkers are proteins that are expressed in various tumors but among normal tissues are selectively expressed only within the ovary in the female germ cells, the oocytes, at precise stages of oogenesis. Our studies in mice indicate the SAS1R protein localized only in the ovary and in the cytoplasm of developing oocytes. Because of this restricted localization in the normal body, cancer-oocyte biomarkers present remarkable opportunities for tumor diagnosis and treatment because they open pathways to selective and specific diagnostics as well as tumor specific therapies. The invention disclosed herein is based on studies exploring the human biology of a SAS1R, as a model cancer-oocyte biomarker, in ovarian and uterine cancers. SAS1R is a zinc metalloprotease which in human ovaries was observed to be first translated at a precise stage of egg development in primary oocytes which are in the transition state between unilaminar primary follicles and bilaminar secondary follicles, a pattern similar to that seen in the mouse ovary. Primary oocytes within primordial follicles and the majority of primary oocytes within primary follicles do not express this metalloprotease and thus will not be affected by therapies which target this enzyme, ensuring preservation of the oocytes that comprise the ovarian reserve, and allowing for immuno- and chemotherapeutic approaches to cancer treatment that preserve fertility.

Using specific reagents, SAS1R transcripts and proteins were identified in human ovarian and uterine tumors. Biopsies in a tissue microarray including Malignant Mixed Mullerian Tumors (MMMT) and Endometrioid carcinomas showed strong immunoreactivity with the polyclonal antibody to SAS1R. Two MMMT derived cell lines were also tested and confirmed the presence of SAS1R transcripts with 99% sequence identity on DNA sequencing. Importantly, SAS1R showed cell surface localization when live cells were studied. Treatment of these human tumor cells with antibodies caused a transformation from a regular polygonal appearance to rounded cells with redistributed actin cytoskeletons. In a real time assay, tumor cells were killed in the presence of specific antibody and complement. PCR of 10 ovarian tumors identified SAS1R in all. Given the lack of definitive diagnostic tests for ovarian and uterine cancers and the poor prognosis for patients with metastasized disease, SAS1R offers a potential diagnostic target for earlier diagnosis of these cancers. Therapies directed against the SAS1R protein may become first line strategies for personalized medicine that selectively target ovarian and uterine tumors while preserving fertility. Cancer-oocyte biomarkers represent a new field of cancer drug targets being developed by the inventors that will provide for a selective mechanism of drug action that targets only the tumor and an expendable population of mature oocytes.

Because SAS1R is 1) an active metalloprotease, 2) is found on the surface of the oocyte and other cells tested, 3) is oocyte specific among normal tissues; and 4) is unexpectedly found in tumors as disclosed herein; SAS1R is an excellent candidate cancer biomarker. SAS1R may have applications as a drug target for selectively targeting uterine cancer while sparing all other tissues in the body [including the stem cell reserve in the ovary because it is absent on primary oocytes within primordial follicles], and as a vaccinogen in a therapeutic vaccine. SAS1R is therefore useful as a diagnostic marker for cancer, particularly uterine and ovarian cancers, and any cancer expressing SAS1R.

The present application shows that SASIR antibody-mediated complement-dependent cell death is observed in MMMT cell lines. Importantly, the data also show that in live cells SAS1R is at the cell surface.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

Mandal A, et al. (2003) SLLP1, a unique, intra-acrosomal, non-bacteriolytic, c lysozyme-like protein of human spermatozoa. Biol Reprod 68, 1525-1537.

Herrero M B, et al. (2005) Mouse SLLP1, a sperm lysozyme-like protein involved in sperm-egg binding and fertilization. Dev Biol 284, 126-142.

Evans J P, Schultz R M, Kopf G S (1995) Mouse sperm-egg plasma membrane interactions: analysis of roles of egg integrins and the mouse sperm homologue of PH-30 (fertilin) beta. J Cell Sci 108, 3267-3278.

Almeida E A, et al. (1995) Mouse egg integrin alpha 6 beta 1 functions as a sperm receptor. Cell 81, 1095-1104.

Yuan R, Primakoff P, Myles, D G (1997) A role for the disintegrin domain of cyritestin, a sperm surface protein belonging to the ADAM family, in mouse sperm-egg plasma membrane adhesion and fusion. J Cell Biol 137, 105-112.

Evans J P, Schultz R M, Kopf G S (1997) Characterization of the binding of recombinant mouse sperm fertilin alpha subunit to mouse eggs: evidence for function as a cell adhesion molecule in sperm-egg binding. Dev Biol 187, 94-106.

Cho C, et al. (1998) Fertilization defects in sperm from mice lacking fertilin beta. Science 281, 1857-1859.

Shamsadin R, et al. (1999) Male mice deficient for germ-cell cyritestin are infertile. Biol Reprod 61, 1445-1451.

Nishimura H, Cho C, Branciforte D R, Myles D G, Primakoff P (2001) Analysis of loss of adhesive function in sperm lacking cyritestin or fertilin beta. Dev Biol 233, 204-213.

Coonrod S A, et al. (1999) Treatment of mouse oocytes with PI-PLC releases 70-kDa (pI 5) and 35- to 45-kDa (pI 5.5) protein clusters from the egg surface and inhibits sperm-oolemma binding and fusion. Dev Biol 207, 334-349.

Miyado K, et al. (2000) Requirement of CD9 on the egg plasma membrane for fertilization. Science 287, 321-324.

Alfieri J A, et al. (2003) Infertility in female mice with an oocyte-specific knockout of GPI-anchored proteins. J Cell Sci 116, 2149-2155.

Kaji K, et al. (2000) The gamete fusion process is defective in eggs of Cd9-deficient mice. Nat Genet. 24, 279-282.

Le Naour F, Rubinstein E, Jasmin C, Prenant M, Boucheix C (2000) Severely reduced female fertility in CD9-deficient mice. Science 287, 319-321.

Rubinstein E, et al. (2006) Reduced fertility of female mice lacking CD81. Dev Biol 290, 351-358.

Cohen D J, Ellerman D A, Cuasnicu P S (2000) Mammalian sperm-egg fusion: evidence that epididymal protein DE plays a role in mouse gamete fusion. Biol Reprod 63, 462-468.

Da Ros V G, et al. (2008) Impaired sperm fertilizing ability in mice lacking Cysteine-RIch Secretory Protein 1 (CRISP1). Dev Biol 320, 12-18.

Inoue N, et al. (2005) The immunoglobulin superfamily protein Izumo is required for sperm to fuse with eggs. Nature 434, 234-238.

Luban J, Goff S P (1995) The yeast two-hybrid system for studying protein-protein interactions. Curr Opin Biotechnol 6, 59-64.

Li X, McDermott B, Yuan B, Goff SP (1996) Homomeric interactions between transmembrane proteins of Moloney murine leukemia virus. J Virol 70, 1266-1270.

Miyado K, et al. (2008) The fusing ability of sperm is bestowed by CD9-containing vesicles released from eggs in mice. Proc Natl Acad Sci USA 105, 12921-12926.

Weigmann A, Corbeil D, Hellwig A, Huttner W B (1997) Prominin, a novel microvilli-specific polytopic membrane protein of the apical surface of epithelial cells, is targeted to plasmalemmal protrusions of non-epithelial cells. Proc Natl Acad Sci USA 94, 12425-12430.

Evans J P, et al. (2000) Effects of perturbation of cell polarity on molecular markers of sperm-egg binding sites on mouse eggs. Biol Reprod 62, 76-84.

Goldman S, Shalev E (2003) The role of the matrix metalloproteinases in human endometrial and ovarian cycles. Eur J Obstet Gynecol Reprod Biol 111, 109-121.

Robinson L L, Sznajder N A, Riley S C, Anderson R A (2001) Matrix metalloproteinases and tissue inhibitors of metalloproteinases in human fetal testis and ovary. Mol Hum Reprod 7, 641-648.

Elia L, Marsh L (1998) A role for a protease in morphogenic responses during yeast cell fusion. J Cell Biol 142, 1473-1485.

Roe J L, Farach H A, Strittmatter W J, Lennarz W J (1988) Evidence for involvement of metalloendoproteases in a step in sea urchin gamete fusion. J Cell Biol 107, 539-544.

Correa L M, Cho C, Myles D G, Primakoff P (2000) A role for a TIMP-3-sensitive, Zn(2+)-dependent metalloprotease in mammalian gamete membrane fusion. Dev Biol 225, 124-134.

Hiroi J, et al. (2004) Structure and developmental expression of hatching enzyme genes of the Japanese eel Anguilla japonica: an aspect of the evolution of fish hatching enzyme gene. Dev Genes Evol 214, 176-184.

Quesada V, Sanchez L M, Alvarez J, Lopez-Otin, C (2004) Identification and characterization of human and mouse ovastacin: a novel metalloproteinase similar to hatching enzymes from arthropods, birds, amphibians, and fish. J Biol Chem 279, 26627-26634.

Bond, J., et al., "The astacin family of metalloendopeptidases", Protein Science (1995), 4: 1247-1261.

Möhrlen, F., et al., "Evolution of astacin-like metalloproteases in animals and their function in development", Evolution and Development, 2008, 8:2, 223-231.

Mandal, A., et al., "Identification of an Oolemmal Receptor for the Sperm Acrosomal Ligand, SLLP1, Biology of Reproduction 78: 69.72 (2008).

Rosmann, S., et al., "Activation of Human Meprin-aα in a Cell Culture Model of Colorectal Cancer is Triggered by the Plasminogen-activating System", The Journal of Biological Chemistry, Vol. 277, No. 43, Issue of Oct. 25, 2002, pp. 40650-40658.

Sterchi, E., et al., "Meprins, membrane-bound and secreted astacin metalloproteinases", Molecular Aspects of Medicine, 29 (2008) 309-328.

Huguenin, M., et al., "The Metalloprotease Meprinβ Processes C-Cadherin and Weakens Intercellular Adhesion", PLos One, May 2008, Vol. 3, Issue 5, e2153, p. 1-11.

Barbara A. Weir, et al 2007 Characterizing the cancer genome in lung adenocarcinoma Nature 450, 893-898.

Martin L. Sos, et al 2009 Predicting drug susceptibility of non-small cell lung cancers based on genetic lesions. J. Clin. Investigation 119, 6 1727-1740.

Rhodes D R. Yu J. Shanker K. Deshpande N. Varambally R. Ghosh D. Barrette T. Pandey A. Chinnaiyan A M. 2004 Large-scale meta-analysis of cancer microarray data identifies common transcriptional profiles of neoplastic transformation and progression. PNAS 101(25), 9309-14. (Jun. 22, 2004).

Rhodes D R, Yu J, Shanker K, Deshpande N, Varambally R, Ghosh D, Barrette T, Pandey A, Chinnaiyan A M. ONCOMINE: a cancer microarray database and integrated data-mining platform. Neoplasia. 2004 January-February; 6(1):1-6.

What is claimed is:

1. A method for treating SAS1R positive cancer comprising administering to a subject in need thereof an effective amount of an antagonist of SAS1R, thereby treating a SAS1R positive cancer,
wherein said cancer is selected from the group consisting of uterine cancer, lung cancer, head and neck cancer, pancreatic cancer, esophageal cancer, colorectal cancer, breast cancer, adenocarcinoma of the lung, squamous carcinoma of the lung, malignant mixed mullerian tumor, leukemia, and lymphoma,
wherein said antagonist of SAS1R activity is an antibody that binds to one or more SAS1R protein fragments selected from the group consisting of amino acids 1-25, 26-50, 51-75, 76-100, 101-125, 126-150, and 151-175 of SAS1R human variant 1 (SEQ ID NO:23).

2. The method of claim 1, wherein said antagonist inhibits SAS1R activity, levels, or expression.

3. The method of claim 1, wherein said antibody is selected from the group consisting of a single chain antibody, a monoclonal antibody, a bi-specific antibody, a chimeric antibody, a synthetic antibody, a polyclonal antibody, a humanized antibody, a fully human antibody, or active fragments or homologs thereof.

4. A method for inhibiting proliferation or killing a SAS1R positive cancer cell comprising contacting said cancer cell with an effective amount of antibody directed against SAS1R or a fragment thereof, wherein said antibody directed against SAS1R or a fragment thereof binds with SAS1R, thereby inhibiting proliferation or killing a cancer cell
wherein said cancer is selected from the group consisting of uterine cancer, lung cancer, head and neck cancer, pancreatic cancer, esophageal cancer, colorectal cancer, breast cancer, adenocarcinoma of the lung, squamous carcinoma of the lung, malignant mixed mullerian tumor, leukemia, and lymphoma,
wherein said antibody binds to one or more SAS1R protein fragments selected from the group consisting of amino acids 1-25, 26-50, 51-75, 76-100, 101-125, 126-150, and 151-175 of SAS1R human variant 1 (SEQ ID NO:23).

5. The method of claim 4, wherein said killing is antibody-mediated complement-dependent cell killing.

6. The method of claim 4, wherein said antibody is conjugated to another molecule or structure.

7. The method of claim 6, wherein said molecule or structure is selected from the group consisting of an antibody, a protein, a pro-drug, a drug, a toxin, a protein toxin, a liposome, a radioactive isotope, and an enzyme.

* * * * *

UNITED STATES PATENT AND TRADEMARK OFFICE
CERTIFICATE OF CORRECTION

| | | |
|---|---|---|
| PATENT NO. | : 9,244,075 B2 | Page 1 of 1 |
| APPLICATION NO. | : 13/813680 | |
| DATED | : January 26, 2016 | |
| INVENTOR(S) | : Herr et al. | |

It is certified that error appears in the above-identified patent and that said Letters Patent is hereby corrected as shown below:

In the specification,

In column 1, lines 20-23, delete "in part with United States Government support under Grant Nos. R03HD055129 awarded by the NIH and D43 TW/HD 00654 from the Fogarty International Center." and insert --with government support under HD055129; TW000654; and HD045783 awarded by the National Institutes of Health.--, therefor.

Signed and Sealed this
Twenty-first Day of June, 2016

Michelle K. Lee
*Director of the United States Patent and Trademark Office*